(12) United States Patent
Neisz et al.

(10) Patent No.: US 7,291,104 B2
(45) Date of Patent: Nov. 6, 2007

(54) SURGICAL ARTICLES AND METHODS

(75) Inventors: Johann J. Neisz, Coon Rapids, MN (US); Robert E. Lund, St. Michael, MN (US); Kimberly A. Anderson, Eagan, MN (US); Vicki R. Vandersloot, Minneapolis, MN (US); Terence M. Moore, Tomkins Cove, NY (US); Mark S. Bouchier, Lakeville, MN (US); Randy L. Morningstar, Brooklyn Park, MN (US); Gary A. Rocheleau, Maple Grove, MN (US)

(73) Assignee: American Medical Systems Inc., Minnetonka, MN (US)

( * ) Notice: Subject to any disclaimer, the term of this patent is extended or adjusted under 35 U.S.C. 154(b) by 0 days.

(21) Appl. No.: 10/675,816

(22) Filed: Sep. 30, 2003

(65) Prior Publication Data

US 2004/0068159 A1 Apr. 8, 2004

Related U.S. Application Data

(63) Continuation of application No. 10/280,945, filed on Oct. 25, 2002, now Pat. No. 7,048,682, which is a continuation of application No. 10/005,837, filed on Nov. 9, 2001, now abandoned, which is a continuation-in-part of application No. 09/917,443, filed on Jul. 27, 2001, now Pat. No. 6,612,977, and a continuation-in-part of application No. 09/917,562, filed on Jul. 27, 2001, now Pat. No. 6,652,450.

(60) Provisional application No. 60/263,472, filed on Jan. 23, 2001, provisional application No. 60/269,829, filed on Feb. 20, 2001, now abandoned, provisional application No. 60/281,350, filed on Apr. 4, 2001, provisional application No. 60/295,068, filed on Jun. 1, 2001, provisional application No. 60/306,915, filed on Jul. 20, 2001.

(51) Int. Cl.
*A61F 2/02* (2006.01)
(52) U.S. Cl. .................................... 600/30
(58) Field of Classification Search ............ 600/29–31; 128/DIG. 25, 897–898
See application file for complete search history.

(56) References Cited

U.S. PATENT DOCUMENTS 2,738,790 A 3/1956 Todt et al.

(Continued)

FOREIGN PATENT DOCUMENTS

DE 2305815 2/1973

(Continued)

OTHER PUBLICATIONS

Access Instrument System with Allosling Fascia, Featuring the Staskin Needle and Dilation Sheath Mar. 29, 1999 5 pages.*

(Continued)

*Primary Examiner*—Samuel Gilbert
(74) *Attorney, Agent, or Firm*—Jose W. Jimenez; Kimberly K. Baxter

(57) ABSTRACT

Surgical instruments, implantable articles and surgical procedures disclosed for treating medical disorders, particularly incontinence. Improved surgical sling procedures are disclosed. Novel surgical instruments and kits for use in sling procedures are also disclosed. The present invention affords options for surgeons with concomitant advantages to the patient and the healthcare provider.

17 Claims, 38 Drawing Sheets

U.S. PATENT DOCUMENTS

| | | |
|---|---|---|
| 3,124,136 A | 3/1964 | Usher |
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,235,238 A | 11/1980 | Ogiu et al. |
| 4,246,660 A | 1/1981 | Wevers |
| 4,441,497 A | 4/1984 | Paudler |
| 4,509,516 A | 4/1985 | Richmond |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,920,986 A | 5/1990 | Biswas |
| 4,932,962 A | 6/1990 | Yoon et al. |
| 4,938,760 A | 7/1990 | Burton et al. |
| 4,969,892 A | 11/1990 | Burton et al. |
| 5,007,894 A | 4/1991 | Enhorning |
| 5,012,822 A | 5/1991 | Schwarz |
| 5,013,292 A | 5/1991 | Lemay |
| 5,019,032 A | 5/1991 | Robertson |
| 5,032,508 A | 7/1991 | Naughton et al. |
| 5,036,867 A | 8/1991 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,188,636 A | 2/1993 | Fedotov |
| 5,209,756 A | 5/1993 | Seedhom et al. |
| 5,250,033 A | 10/1993 | Evans et al. |
| 5,256,133 A | 10/1993 | Spitz |
| 5,281,237 A | 1/1994 | Gimpelson |
| 5,328,077 A | 7/1994 | Lou |
| 5,337,736 A | 8/1994 | Reddy |
| 5,362,294 A | 11/1994 | Seitzinger |
| 5,368,595 A | 11/1994 | Lewis |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,520,700 A | 5/1996 | Beyar et al. |
| 5,544,664 A | 8/1996 | Benderev et al. |
| 5,562,689 A | 10/1996 | Green et al. |
| 5,571,139 A | 11/1996 | Jenkins, Jr. |
| 5,591,163 A | 1/1997 | Thompson |
| 5,611,515 A | 3/1997 | Benderev et al. |
| 5,628,756 A | 5/1997 | Barker, Jr. et al. |
| 5,633,286 A | 5/1997 | Chen |
| 5,669,935 A | 9/1997 | Rosenman et al. |
| 5,683,349 A | 11/1997 | Makower et al. |
| 5,807,403 A | 9/1998 | Beyar et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,934,283 A | 8/1999 | Willem et al. |
| 5,935,122 A | 8/1999 | Fourkas et al. |
| 5,944,732 A | 8/1999 | Raulerson et al. |
| 5,972,000 A | 10/1999 | Beyar et al. |
| 5,988,171 A | 11/1999 | Sohn et al. |
| 5,997,554 A | 12/1999 | Thompson |
| 6,010,447 A | 1/2000 | Kardjian |
| 6,030,393 A | 2/2000 | Corlew |
| 6,031,148 A | 2/2000 | Hayes et al. |
| 6,042,534 A | 3/2000 | Gellman et al. |
| 6,042,536 A | 3/2000 | Tihon et al. |
| 6,050,937 A | 4/2000 | Benderev |
| 6,053,935 A | 4/2000 | Brenneman et al. |
| 6,068,591 A | 5/2000 | Bruckner et al. |
| 6,071,290 A | 6/2000 | Compton |
| 6,106,545 A | 8/2000 | Egan |
| 6,110,101 A | 8/2000 | Tihon et al. |
| 6,117,067 A | 9/2000 | Gil-Vernet |
| 6,168,611 B1 | 1/2001 | Risvl |
| 6,221,005 B1 | 4/2001 | Bruckner et al. |
| 6,273,852 B1 | 8/2001 | Lehe et al. |
| 6,302,840 B1 | 10/2001 | Benderev |
| 6,306,079 B1 | 10/2001 | Trabucco |
| 6,328,744 B1 | 12/2001 | Hararl et al. |
| 6,334,446 B1 | 1/2002 | Beyar |
| 6,352,553 B1 | 3/2002 | van der Burg et al. |
| 6,382,214 B1 | 5/2002 | Raz et al. |
| 6,406,423 B1 | 6/2002 | Scetbon |
| 6,406,480 B1 | 6/2002 | Beyar et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,494,906 B1 | 12/2002 | Owens |
| 6,502,578 B2 | 1/2003 | Raz et al. |
| 6,530,943 B1 | 3/2003 | Hoepffner et al. |
| 6,575,897 B1 | 6/2003 | Ory et al. |
| 6,582,443 B2 | 6/2003 | Cabak et al. |
| 6,592,515 B2 | 7/2003 | Thierfelder et al. |
| 6,596,001 B2 | 7/2003 | Stormby et al. |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin et al. |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau et al. |
| 6,648,921 B2 | 11/2003 | Anderson et al. |
| 6,652,450 B2 | 11/2003 | Neisz et al. |
| 6,685,629 B2 | 2/2004 | Therin |
| 6,689,047 B2 | 2/2004 | Gellman |
| 6,691,711 B2 | 2/2004 | Raz et al. |
| 6,699,175 B2 | 3/2004 | Miller |
| 2001/0049467 A1 | 12/2001 | Lehe et al. |
| 2002/0055748 A1 | 5/2002 | Gellman et al. |
| 2002/0058959 A1* | 5/2002 | Gellman .................. 606/185 |
| 2002/0072694 A1 | 6/2002 | Snitkin et al. |
| 2002/0077526 A1 | 6/2002 | Kammerer et al. |
| 2002/0091298 A1* | 7/2002 | Landgrebe .................. 600/29 |
| 2002/0091373 A1* | 7/2002 | Berger .................. 606/1 |
| 2002/0099259 A1 | 7/2002 | Anderson et al. |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0188169 A1 | 12/2002 | Kammerer et al. |
| 2003/0004581 A1 | 1/2003 | Rousseau |
| 2003/0009181 A1 | 1/2003 | Gellman et al. |
| 2003/0023137 A1 | 1/2003 | Gellman |
| 2003/0023138 A1 | 1/2003 | Luscombe |
| 2003/0036676 A1 | 2/2003 | Scetbon |

| | | | |
|---|---|---|---|
| 2003/0045774 A1 | 3/2003 | Staskin et al. | |
| 2003/0050530 A1 | 3/2003 | Neisz et al. | |
| 2003/0065246 A1 | 4/2003 | Inman et al. | |
| 2003/0114866 A1 | 6/2003 | Ulmsten et al. | |
| 2003/0130670 A1 | 7/2003 | Anderson et al. | |
| 2003/0149440 A1 | 8/2003 | Kammerer et al. | |
| 2003/0171644 A1 | 9/2003 | Anderson et al. | |
| 2003/0176762 A1 | 9/2003 | Kammerer | |

FOREIGN PATENT DOCUMENTS

| | | | | |
|---|---|---|---|---|
| EP | 0 470 308 A1 | 2/1992 | | |
| EP | 0 650 703 A1 | 6/1994 | | |
| EP | 0 643 945 A2 | 7/1994 | | |
| EP | 1 093 758 A1 | 4/2001 | | |
| EP | 1 060 714 A3 | 9/2002 | | |
| IT | 1299162 | 4/1998 | | |
| RU | 1225547 A1 | 4/1986 | | |
| WO | WO93/17635 A1 | 9/1993 | | |
| WO | WO93/19678 A2 | 10/1993 | | |
| WO | WO97/47246 | * 12/1997 | ................. | 600/30 |
| WO | WO98/19606 A1 | 5/1998 | | |
| WO | WO98/35616 A1 | 8/1998 | | |
| WO | WO98/35632 A1 | 8/1998 | | |
| WO | WO99/016381 A1 | 4/1999 | | |
| WO | WO99/52450 A1 | 10/1999 | | |
| WO | WO 00/13601 A1 | 3/2000 | | |
| WO | WO 00/18319 A1 | 4/2000 | | |
| WO | WO 00/027304 A1 | 5/2000 | | |
| WO | WO 00/57812 A1 | 10/2000 | | |
| WO | WO 00/64370 A1 | 11/2000 | | |
| WO | WO 00/74594 A1 | 12/2000 | | |
| WO | WO 00/74613 A1 | 12/2000 | | |
| WO | WO 00/74633 A2 | 12/2000 | | |
| WO | WO 01/06951 A1 | 2/2001 | | |
| WO | WO 01/26581 A1 | 4/2001 | | |
| WO | WO 01/39670 A1 | 6/2001 | | |
| WO | WO 01/45589 A1 | 6/2001 | | |
| WO | WO 01/56499 A1 | 8/2001 | | |
| WO | WO 02/28312 A1 | 4/2002 | | |
| WO | WO 02/32284 A2 | 4/2002 | | |
| WO | WO 02/34124 A2 | 5/2002 | | |
| WO | WO 02/38079 A2 | 5/2002 | | |
| WO | WO 02/39890 A2 | 5/2002 | | |
| WO | WO 02/071953 A2 | 9/2002 | | |
| WO | WO 02/078552 A1 | 10/2002 | | |
| WO | WO 03/017848 A1 | 3/2003 | | |
| WO | WO 03/028585 A2 | 4/2003 | | |
| WO | WO 03/037215 A2 | 5/2003 | | |
| WO | WO 03/041613 A1 | 5/2003 | | |
| WO | WO 03/047435 A1 | 6/2003 | | |
| WO | WO 04/016180 A2 | 2/2004 | | |

OTHER PUBLICATIONS

U.S. Appl. No. 60/356,697, filed Feb. 14, 2002, Kammerer.
Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).
Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).
Araki, Tohru et al., The Loop-Loosening Procedure for Urination Difficulties After Stamey Suspension of the Vesical Neck, The Journal of Urology, vol. 144, pp. 319-323 (Aug. 1990).
Asmussen, M. et al., Simultaneous Urethro-Cystometry With a New Technique, Scand J Urol Nephrol 10, p. 7-11 (1976).
Beck, Peter R. et al., Treatment of Urinary Stress Incontinence With Anterior Colporrhaphy, Obtetrics and Gynecology, vol. 59 (No. 3), pp. 269-274 (Mar. 1982).
Benderev, Theodore V., MD, A Modified Percutaneous Outpatient Bladder Neck Suspension System, Journal of Urology, vol. 152, pp. 2316-2320 (Dec. 1994).

Benderev, Theodore V., MD, Anchor Fixation and Other Modifications of Endoscopic Bladder Neck Suspension, Urology, vol. 40, No. 5, pp. 409-418 (Nov. 1992).
Bergman, Arieh et al., Three Surgical Procedures for Genuine Stress Incontinence: Five-Year Follow-Up of a Prospective Randomized Study, Am J Obstet Gynecol, vol. 173 No. 1, pp. 66-71 (Jul. 1995).
Blaivas, Jerry et al., Pubovaginal Fascial Sling for the Treatment of Complicated Stress Urinary Incontinence, The Journal of Urology, vol. 145, pp. 1214-1218 (Jun. 1991).
Blaivas, Jerry et al., Type III Stress Urinary Incontinence: Importance of Proper Diagnosis and Treatment, Surgical Forum, pp. 473-475, (1984).
Blavis, Jerry, Commentary: Pubovaginal Sling Procedure, Experience with Pubovaginal Slings, pp. 93-101 (1990).
Boyles, Sarah Hamilton et al., Procedures for Urinary Incontinence in the United States, 1979-1997, Am J Obstet Gynecol, vol. 189, n. 1, pp. 70-75 (Jul. 2003).
Bryans, Fred E., Marlex Gauze Hammock Sling Operation With Cooper's Ligament Attachment in the Management of Recurrent Urinary Stress Incontinence, American Journal of Obstetrics and Gynecology, vol. 133, pp. 292-294 (Feb. 1979).
Burch, John C., Urethrovaginal Fixation to Cooper's Ligament for Correction of Stress Incontinence, Cystocele, and Prolapse, Am. J. Obst. & Gyn, vol. 31, pp. 281-290 (1961).
Cervigni, Mauro et al., The Use of Synthetics in the Treatment of Pelvic Organ Prolapse, Voiding Dysfunction and Female Urology, vol. 11, pp. 429-435 (2001).
Choe, Jong M. et al., Gore-Tex Patch Sling: 7 Years Later, Urology, vol. 54, pp. 641-646 (1999).
Cook/Ob Gyn®, Urogynecology, Copyright Cook Urological Inc., pp. 1-36 (1996).
Daher, N. et al, Pre-pubic TVT: An Alternative to Classic TVT in Selected Patients with Urinary Stress Incontinence, European Journal of Obstetrics, Gynecology, and Reproductive Biology, 107, pp. 205-207 (2003).
Dargent, D. et al., Insertion of a Suburethral Sling Through the Obturator Membrane in the Treatment of Female Urinary Incontinence, Gynecol Obstet Fertil, vol. 30, pp. 576-582 (2002).
Das, Sakti et al., Laparoscopic Colpo-Suspension, The Journal of Urology, vol. 154, pp. 1119-1121 (Sep. 1995).
Debodiance, Phillippe et al, Tolerance of Synthetic Tissues in Touch with Vaginal Scars: Review to the Point of 187 Cases, European Journal of Obstetrics, Gynecology, and Reproductive Biology, 87, pp. 23-30 (1999).
Decter, Ross M., Use of the Fascial Sling for Neurogenic Incontinence: Lessons Learned, The Journal of Urology, vol. 150, pp. 683-686 (Aug. 1993).
DeLancey, John, MD, Structural Support of the Urethra as it Relates to Stress Urinary Incontinence: The Hammock Hypothesis, Am J Obstet Gynecol, vol. 170 No. 6, pp. 1713-1723 (Jun. 1994).
Delorme, Emmanuel, Trans-Obturator Sling: A Minimal Invasive Procedure to Treat Female Stress Urinary Incontinence, Progres en Urologie, vol. 11, pp. 1306-1313 (2001). English translation attached.
Diana, et al., Treatment of Vaginal Vault Prolapse With Abdominal Sacral Colpopexy Using Prolene Mesh, American Journal of Surgery, vol. 179, pp. 126-128, (Feb. 2000).
Eglin et al., Transobturator Subvesical Mesh, Tolerance and short-term results of a 103 case continuous series, Gynecologie Obstetrique & Fertilite, vol. 31, Issue 1, pp. 14-19 (Jan. 2003).
Enzelsberger, H. et al., Urodynamic and Radiologic Parameters Before and After Loop Surgery for Recurrent Urinary Stress Incontinence, Acta Obstet Gynecol Scand, 69, pp. 51-54 (1990).
Eriksen, Bjarne C. et al., Long-Term Effectiveness of the Burch Colposuspension in Female Urinary Stress Incontinence, Acta Obstet Gynecol Scand, 69, pp. 45-50 (1990).
Falconer, C. et al., Clinical Outcome and Changes in Connective Tissue Metabolism After Slingplasty in Stress Incontinence Women, International Urogynecology Journal, pp. 133-137 (1966).
Falconer, C. et al., Influence of Different Sling Materials of Connective Tissue Metabolism in Stress Urinary Incontinent Women, International Urogynecology Journal, Supp. 2, pp. S19-S23 (2001).

Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).

Farquhar, Cynthia M. et al., Hysterectomy Rates in the United States 1990-1997, Obstetrics & Gynecology, vol. 99, n. 2, pp. 229-234 (Feb. 2002).

Fidela, Marie R. et al., Pelvic Support Defects and Visceral and Sexual Function in Women Treated with Sacrospinous Ligament Suspension and Pelvic Reconstruction, Am J Obstet Gynecol, vol. 175, n. 6 (Dec. 1996).

Flood, C.G. et al., Anterior Colporrhaphy Reinforce With Marlex Mesh for the Treatment of Cystoceles, International Urogynecology Journal, vol. 9, pp. 200-204 (1998).

Gilja, Ivan et al., A Modified Raz Bladder Neck Suspension Operation (Transvaginal Burch), The Journal of Urology, vol. 153, pp. 1455-1457 (May 1995).

Gittes, Ruben F. et al., No-Incision Pubovaginal Suspension for Stress Incontinence, The Journal of Urology, vol. 138 (Sep. 1987).

Guner, et al., Transvaginal Sacrospinous Colpopexy for Marked Uterovaginal and Vault Prolapse, Inter J of Gynec & Obstetrics, vol. 74, pp. 165-170 (2001).

Handa, Victoria L. et al, Banked Human Fascia Lata for the Suburethral Sling Procedure: A Preliminary Report, Obstetrics & Gynecology, vol. 88 No. 6, 5 pages (Dec. 1996).

Heit, Michael et al., Predicting Treatment Choice for Patients with Pelvic Organ Prolapse, Obstetrics & Gynecology, vol. 101, n. 6, pp. 1279-1284 (Jun. 2003).

Henriksson, L. et al., A Urodynamic Evaluation of the Effects of Abdominal Urethrocystopexy and Vaginal Sling Urethroplasty in Women With Stress Incontinence, Am. J. Obstet. Gynecol. vol. 131, No. 1, pp. 77-82 (Mar. 1, 1978).

Hodgkinson, C. Paul et al., Urinary Stress Incontinence in the Female, Department of Gynecology and Obstetrics, Henry Ford Hospital, vol. 10, No. 5, p. 493-499, (Nov. 1957).

Holschneider, C. H., et al., The Modified Pereyra Procedure in Recurrent Stress Urinary Incontinence: A 15-year Review, Obstetrics & Gynecology, vol. 83, No. 4, pp. 573-578 (Apr. 1994).

Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648-652 (Apr. 1998).

Ingelman-Sunberg, A. et al., Surgical Treatment of Female Urinary Stress Incontinence, Contr. Gynec. Obstet., vol. 10, pp. 51-69 (1983).

Jeffcoate, T.N.A. et al., The Results of the Aldridge Sling Operation for Stress Incontinence, Journal of Obstetrics and Gynaecology, pp. 36-39 (1956).

Jones, N.H.J. Reay et al., Pelvic Connective Tissue Resilience Decreases with Vaginal Delivery, Menopause and Uterine Prolapse, Br J Surg, vol. 90, n. 4, pp. 466-472 (Apr. 2003).

Julian, Thomas, The Efficacy of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).

Karram, Mickey et al., Patch Procedure: Modified Transvaginal Fascia Lata Sling for Recurrent for Severe Stress Urinary Incontinence, vol. 75, pp. 461-463 (Mar. 1990).

Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).

Kersey, J., The Gauze Hammock Sling Operation in the Treatment of Stress Incontintence, British Journal of Obstetrics and Gynaecology, vol. 90, pp. 945-949 (Oct. 1983).

Klutke, Carl et al., The Anatomy of Stress Incontinence: Magnetic Resonance Imaging of the Female Bladder Neck and Urethra, The Journal of Urology, vol. 143, pp. 563-566 (Mar. 1990).

Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).

Klutke, John M.D. et al, The promise of tension-free vaginal tape for female SUI, Contemporary Urology, 7 pages (Oct. 2000).

Korda, A. et al., Experience with Silastic Slings for Female Urinary Incontience, Aust NZ J. Obstet Gynaecol, vol. 29, pp. 150-154 (May 1989).

Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).

Leach, Gary E., et al., Female Stress Urinary Incontinence Clinical Guidelines Panel Report on Surgical Management of Female Stress Urinary Incontinence, American Urological Association, vol. 158, pp. 875-880 (Sep. 1997).

Leach, Gary E., MD, Bone Fixation Technique for Transvaginal Needle Suspension, Urology vol. XXXI, No. 5, pp. 388-390 (May 1988).

Lichtenstein, Irving L. et al, The Tension Free Hernioplasty, The American Journal of Surgery, vol. 157 pp. 188-193 (Feb. 1989).

Loughlin, Kevin R. et al., Review of an 8-Year Experience with Modifications of Endoscopic Suspension of the Bladder Neck for Female Stress Incontinence, The Journal of Uroloyg, vol. 143, pp. 44-45 (1990).

Luber, Karl M. et al., The Demographics of Pelvic Floor Disorders; Current Observations and Future Projections, Am J Obstet Gynecol, vol. 184, n. 7, pp. 1496-1503 (Jun. 2001).

Mage, Technique Chirurgicale, L'Interpostion D'un Treillis Synthetique Dans La Cure Par Voie Vaginale Des Prolapsus Genitaux, J Gynecol Obstet Biol Reprod, vol. 28, pp. 825-829 (1999).

Marchionni, Maruro et al., True Incidence of Vaginal Vault Prolapse—Thirteen Years of Experience, Journal of Reproductive Medicine, vol. 44, n. 8, pp. 679-684 (Aug. 1999).

Marinkovic, Serge Peter et al., Triple Compartment Prolapse: Sacrocolpopexy with Anterior and Posterior Mesh Extensions, Br J Obstet Gynaecol, vol. 110, pp. 323-326 (Mar. 2003).

Marshall, Victor Fray et al. The Correction of Stress Incontinence by Simple Vesicourethral Suspension, Surgery, Gynecology and Obstetrics, vol. 88, pp. 509-518 (1949).

McGuire, Edward J. et al., Pubovaginal Sling Procedure for Stress Incontinence, The Journal of Urology, vol. 119, pp. 82-84 (Jan. 1978).

McGuire, Edward J. et al., Abdominal Procedures for Stress Incontinence, Urologic Clinics of North America, pp. 285-290, vol. 12, No. 2 (May 1985).

McGuire, Edward J. et al., Experience with Pubovaginal Slings for Urinary Incontinence at the University of Michigan, Journal of Urology, vol. 138, pp. 90-93 (1987).

McGuire, Edward J. et al., Abdominal Fascial Slings, Slings, Raz Female Urology, p. 369-375 (1996).

McIndoe, G. A. et al., The Aldridge Sling Procedure in the Treatment of Urinary Stress Incontinence, Aust. N Z Journal of Obstet Gynecology, pp. 238-239 (Aug. 1987).

McKiel, Charles F. Jr., et al, Marshall-Marchetti Procedure Modification, vol. 96, pp. 737-739 (Nov. 1966).

Migliari, Roberto et al., Tension-Free Vaginal Mesh Repair for Anterior Vaginal Wall Prolapse, Eur Urol, vol. 38, pp. 151-155 (Oct. 1999).

Migliari, Roberto et al., Treatment Results Using A Mixed Fiber Mesh in Patients with Grade IV Cystocele, Journal of Urology, vol. 161, pp. 1255-1258 (Apr. 1999).

Moir, J. Chassar et.al., The Gauze-Hammock Operation, The Journal of Obstetrics and Gynaecology of British Commonwealth, vol. 75 No. 1, pp. 1-9 (Jan. 1968).

Morgan, J. E., A Sling Operation, Using Marlex Polypropylene Mesh, for the Treatment of Recurrent Stress Incontinence, Am. J. Obst. & Gynecol, pp. 369-377 (Feb. 1970).

Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).

Morley, George W. et al., Sacrospinous Ligament Fixations for Eversion of the Vagina, Am J Obstet Gyn, vol. 158, No. 4, pp. 872-881 (Apr. 1988).

Narik, G. et al., A Simplified Sling Operation Suitable for Routine Use, Gynecological and Obstetrical Clinic, University of Vienna, vol. 84, No. 3, p. 400-405, (Aug. 1, 1962).

Natale, F. et al., Tension Free Cystocele Repair (TCR): Long-Term Follow-Up, International Urogynecology Journal, vol. 11, supp. 1, p. S51 (Oct. 2000).

Nichols, David H., The Mersilene Mesh Gauze-Hammock for Severe Urinary Stress Incontinence, Obstetrics and Gynecology, vol. 41, pp. 88-93 (Jan. 1973).

Nicita, Giulio, A New Operation for Genitourinary Prolapse, Journal of Urology, vol. 160, pp. 741-745 (Sep. 1998).

Niknejad, Kathleen et al., Autologous and Synthetic Urethral Slings for Female Incontinence, Urol Clin N Am, vol. 29, pp. 597-611 (2002).

Norris, Jeffrey P. et al., Use of Synthetic Material in Sling Surgery: A Minimally Invasive Approach, Journal of Endourology, vol. 10, pp. 227-230 (Jun. 1996).

O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).

Ostergard, Donald R. et al., Urogynecology and Urodynamics Theory and Practice, pp. 569-579 (1996).

Paraiso et al., Laparoscopic Surgery for Enterocele, Vaginal Apex Prolapse and Rectocele, Int. Urogynecol J, vol. 10, pp. 223-229 (1999).

Parra, R. O., et al, Experience with a Simplified Technique for the Treatment of Female Stress Urinary Incontinence, British Journal of Urology, pp. 615-617 (1990).

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45-50 (1999).

Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).

Pereyra, Armand J., M.D., F.S.C.S., A Simplified Surgical Procedure for Correction of Stress Incontinence in Women, West.J.Surg., Obst. & Gynec, p. 223-226, (Jul.-Aug. 1959).

Peter E. Papa Petros et al., Cure of Stress Incontinence by Repair of External Anal Sphincter, Acta Obstet Gynecol Scand, vol. 69, Sup 153, p. 75 (1990).

Peter Petros et al., Anchoring the Midurethra Restores Bladder-Neck Anatomy and Continence, The Lancet, vol. 354, pp. 997-998 (Sep. 18, 1999).

Petros, Peter E. Papa et al., An Anatomical Basis for Success and Failure of Female Incontinence Surgery, Scandinavian Journal of Neurourology and Urodynamics, Sup 153, pp. 55-60 (1993).

Petros, Peter E. Papa et al., An Analysis of Rapid Pad Testing and the History for the Diagnosis of Stress Incontinence, Acta Obstet Gynecol Scand, vol. 71, pp. 529-536 (1992).

Petros, Peter E. Papa et al., An Integral Theory of Female Urinary Incontinence, Acta Obstetricia et Gynecologica Scandinavica, vol. 69 Sup. 153, pp. 7-31 (1990).

Petros, Peter E. Papa et al., Bladder Instability in Women: A Premature Activation of the Micturition Reflex, Scandinavian Journal of Neurourology and Urodynamics, Sup 153, pp. 235-239 (1993).

Petros, Peter E. Papa et al., Cough Transmission Ratio: An Indicator of Suburethral Vaginal Wall Tension Rather than Urethral Closure?, Acta Obstet Gynecol Scand, vol. 69, Sup 153, pp. 37-39 (1990).

Petros, Peter E. Papa et al., Cure of Urge Incontinence by the Combined Intravaginal Sling and Tuck Operation, Acta Obstet Gynecol Scand, vol. 69, Sup 153, pp. 61-62 (1990).

Petros, Peter E. Papa et al., Further Development of the Intravaginal Slingplasty Procedure—IVS III—(with Midline "Tuck"), Scandinavian Journal of Neurourology and Urodynamics, Sup 153, p. 69-71 (1993).

Petros, Peter E. Papa et al., Medium-Term Follow-Up of the Intravaginal Slingplasty Operation Indicates Minimal Deterioration of Urinary Continence with Time, (3 pages) (1999).

Petros, Peter E. Papa et al., Non Stress Non Urge Female Urinary Incontinence-Diagnosis and Cure: A Preliminary Report, Acta Obstet Gynecol Scand, vol. 69, Sup 153, pp. 69-70 (1990).

Petros, Peter E. Papa et al., Part I: Theoretical, Morphological, Radiographical Correlations and Clinical Perspective, Scandinavian Journal of Neurourology and Urodynamics, Sup 153, pp. 5-28 (1993).

Petros, Peter E. Papa et al., Part II: The Biomechanics of Vaginal Tissues and Supporting Ligaments with Special Relevance to the Pathogenesis of Female Urinary Incontinence, Scandinavian Journal of Neurology and Urodynamics, Sup 153, pp. 29-40 plus cover sheet (1993).

Petros, Peter E. Papa et al., Part III: Surgical Principles Deriving from the Theory, Scandinavian Journal of Neurourology and Urodynamics, Sup 153, pp. 41-52 (1993).

Petros, Peter E. Papa et al., Part IV: Surgical Applications of the Theory-Development of the Intravaginal Sling Pklasty (IVS) Procedure, Scandinavian Journal of Neurourology and Urodynamics, Sup 153, pp. 53-54 (1993).

Petros, Peter E. Papa et al., Pelvic Floor Rehabilitation According to the Integrated Theory of Female Incontinence, Chapter 7, pp. 249-258 (book chapter).

Petros, Peter E. Papa et al., Pinch Test for Diagnosis of Stress Urinary Incontinence, Acta Obstet Gynecol Scand, vol. 69, Sup 153, pp. 33-35 (1990).

Petros, Peter E. Papa et al., Pregnancy Effects on the Intravaginal Sling Operation, Acta Obstet Gynecol Scand, vol. 69, Sup 153, pp. 77-79 (1990).

Petros, Peter E. Papa et al., The Autogenic Ligament Procedure: A Technique for Planned Formation of an Artificial Neo-Ligament, Acta Obstet Gynecol Scand, vol. 69, Sup 153, pp. 43-51 (1990).

Petros, Peter E. Papa et al., The Combined Intravaginal Sling and Tuck Operation and Ambulatory Procedure for Cure of Stress and Urge Incontinence, Acta Obstet Gynecol Scand, vol. 69, Sup 153, pp. 53-59 (1990).

Petros, Peter E. Papa et al., The Development of the Intravaginal Slingplasty Procedure: IVS II-(With Bilateral "Tucks"), Scandinavian Journal of Neurourology and Urodynamics, Sup 153, pp. 61-67 (1993).

Petros, Peter E. Papa et al., The Free Graft Procedure for Cure of the Tethered Vagina Syndrome, Scandinavian Journal of Neurology and Urodynamics, Sup 153, pp. 85-87 (1993).

Petros, Peter E. Papa et al., The Further Development of the Intravaginal Slingplasty Procedure—IVS IV—(With "Double Breasted" Unattached Vaginal Flap Repair and "Free" Vaginal Tapes), Scandinavian Journal of Neurourology and Urodynamics, Sup 153, p. 73-75 (1993).

Petros, Peter E. Papa et al., The Further Development of the Intravaginal Slingplasty Procedure—IVS V—(With "Double Breasted" Unattached Vaginal Flap Repair and Permanent Sling)., Scandinavian Journal of Neurourology and Urodynamics, Sup 153, pp. 77-79 (1993).

Petros, Peter E. Papa et al., The Intravaginal Slingplasty Operation, A Minimally Invasive Technique for Cure of Urinary Incontinence in the Female, Aust. NZ J Obstet Gynaecol, vol. 36, n. 4, pp. 453-461 (1996).

Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81-84 (1993).

Petros, Peter E. Papa et al., The Posterior Fornix Syndrome: A Multiple Symptom Complex of Pelvic Pain and Abnormal Urinary Symptoms Deriving from Laxity in the Posterior Fornix of Vagina, Scandinavian Journal of Neurourology and Urodynamics, Sup 153, pp. 89-93 (1993).

Petros, Peter E. Papa et al., The Role of a Lax Posterior Vaginal Fornix in the Causation of Stress and Urgency Symptoms: A Preliminary Report, Acta Obstet Gynecol Scand, vol. 69, Sup 153, pp. 71-73 (1990).

Petros, Peter E. Papa et al., The Tethered Vagina Syndrome, Post Surgical Incontinence and I-Plasty Operation for Cure, Acta Obstet Gynecol Scand, vol. 69, Sup 153, pp. 63-67 (1990).

Petros, Peter E. Papa et al., The Tuck Procedure: A Simplified Vaginal Repair for Treatment of Female Urinary Incontinence, Acta Obstet Gynecol Scand, vol. 69, Sup 153, pp. 41-42 (1990).

Petros, Peter E. Papa et al., Urethral Pressure Increase on Effort Originates From Within the Urethra, and Continence From Musculovaginal Closure, Scandinavian Journal of Neurourology and Urodynamics, pp. 337-350 (1995).

Petros, Peter E. Papa, Development of Generic Models for Ambulatory Vaginal Surgery—Preliminary Report, International Urogynecology Journal, pp. 20-27 (1998).

Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270-278, (1997).

Petros, Peter E. Papa, Vault Prolapse II; Restoration of Dynamic Vaginal Supports by Infracoccygeal Sacropexy, an Axial Day-Case Vaginal Procedure, Int Urogynecol J, vol. 12, pp. 296-303 (2001).

Rackley, Raymond R. et al., Tension-Free Vaginal Tape and Percutaneous Vaginal Tape Sling Procedures, Techniques in Urology, vol. 7, No. 2, pp. 90-100 (2001).

Rackley, Raymond R. M.D., Synthetic Slings: Five Steps for Successful Placement, Urology Times, p. 46,48,49 (Jun. 2000).

Raz, Shlomo, et al., The Raz Bladder Neck Suspension Results in 206 Patients, The Journal of Urology, pp. 845-846 (1992).

Raz, Shlomo, Female Urology, pp. 80-86, 369-398, 435-442 (1996).

Raz, Shlomo, MD, Modified Bladder Neck Suspension for Female Stress Incontinence, Urology, vol. XVII, No. 1, pp. 82-85 (Jan. 1981).

Richardson, David A. et al., Delayed Reaction to the Dacron Buttress Used in Urethropexy, The Journal of Reproductive Medicine, pp. 689-692, vol. 29, No. 9 (Sep. 1984).

Richter, K., Massive Eversion of the Vagina: Pathogenesis, Diagnosis and Therapy of the "True" Prolapse of the Vaginal Stump, Clin obstet gynecol, vol. 25, pp. 897-912 (1982).

Ridley, John H., Appraisal of the Goebell-Frangenheim-Stoeckel Sling Procedure, American Journal Obst & Gynec., vol. 95, No. 5, pp. 741-721 (Jul. 1, 1986).

Roberts, Henry, M.D., Cystourethrography in Women, Deptment of Obstetrics and Gynaecology, University of Liverpool, May 1952, vol. XXXV, No. 293, pp. 253-259.

Sanz, Luis E. et al., Modification of Abdominal Sacrocolpopexy Using a Suture Anchor System, The Journal of Reproductive Medicine, vol. 48, No. 7, pp. 496-500 (Jul. 2003).

Seim, Arnfinn et al., A Study of Female Urinary Incontinence in General Practice—Demography, Medical History, and Clinical Findings, Scand J Urol Nephrol, vol. 30, pp. 465-472 (1996).

Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).

Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).

Spencer, Julia R. et al, A Comparison of Endoscopic Suspension of the Vesical Neck with Suprapubic Vesicourethropexy for Treatment of Stress Urinary Incontinence, The Journal of Urology, vol. 137, pp. 411-415 (Mar. 1987).

Starney, Thomas A., M.D., Endoscopic Suspension of the Vesical Neck for Urinary Incontinence in Females, Ann. Surgery, vol. 192 No. 4, 465-471 (Oct. 1980).

Stanton, Stuart L., Suprapubic Approaches for Stress Incontinence in Women, Journal of American Geriatrics Society, vol. 38, No. 3, pp. 348-351 (Mar. 1990).

Stanton, Stuart, Springer-Veglag, Surgery of Female Incontinence, pp. 105-113 (1986).

Staskin, David R. et al., Synthetic Slings: Pros and Cons, Current Urology Reports 2002 (3), pp. 414-417 (2002).

Staskin, David R. et al., The Gore-Tex Sling Procedure for Female Sphincteric Incontinence: Indications, Technique, and Results, World Journal of Urology, vol. 15, pp. 295-299 (1997).

Studdiford, William E., Transplantation of Abdominal Fascia for the Relief of Urinary Stress Incontinence, American Journal of Obstetrics and Gynecology, pp. 764-775 (1944).

Subak, Leslee L. et al., Cost of Pelvic Organ Prolapse Surgery in the United States, Obstetrics & Gynecology, vol 98, No. 4, pp. 646-651 (Oct. 2001).

Sullivan, Eugene S. et al., Total Pelvic Mesh Repair a Ten-Year Experience, Dis. Colon Rectum, vol. 44, No. 6, pp. 857-863 (Jun. 2001).

Swift, S.E., et al., Case-Control Study of Etiologic Factors in the Development of Server Pelvic Organ Prolapse, Int Urogynecol J, vol. 12, pp. 187-192 (2001).

TVT Tension-free Vaginal Tape, Gynecare, Ethicon, Inc., 23 pages (1999).

Ulmsten, U. et al., A Multicenter Study of Tension-Free Vaginal Tape (TVT) for Surgical Treatment of Stress Urinary Incontinence, International Urogynecology Journal, vol. 9, pp. 210-213 (1998).

Ulmsten, U. et al., An Ambulatory Surgical Procedure Under Local Anesthesia for Treatment of Female Urinary Incontinence, International Urogynecology Journal, vol. 7, pp. 81-86 (May 1996).

Ulmsten, U., Female Urinary Incontinence—A Symptom, Not A Urodynamic Disease. Some Theoretical and Practical Aspects on the Diagnosis a Treatment of Female Urinary Incontinence, International Urogynecology Journal, vol. 6, pp. 2-3 (1995).

Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).

Ulmsten, Ulf et al., Different Biochemical Composition of Connective Tissue in Continent, Acta Obstet Gynecol Scand, pp. 455-457 (1987).

Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).

Ulmsten, Ulf et al. The Unstable Female Urethra, Am. J. Obstet. Gynecol., vol. 144 No. 1, pp. 93-97 (Sep. 1, 1982).

Vesica® Percutaneous Bladder Neck Stabilization Kit, A New Approach to Bladder Neck Suspenison, Microvasive® Boston Scientific Corporation, 4 pages (1995).

Vesica® Sling Kits, Simplifying Sling Procedures, Microvasive® Boston Scientific Corporation, 4 pages (1998).

Villet, R., Réponse De R. Villet Å L'Article De D. Dargent et al., Gynécolgie Obstétrique & Fertilité, vol. 31, p. 96 (2003).

Walters, Mark D., Percutaneous Suburethral Slings: State of the Art, Presented at the conference of the American Urogynecologic Society, Chicago, 29 pages (Oct. 2001).

Waxman, Steve et al., Advanced Urologic Surgery for Urinary Incontinence, The Female Patient, pp. 93-100, vol. 21 (Mar. 1996).

Weber, Anne M. et al., Anterior Vaginal Prolapse: Review of Anatomy and Techniques of Surgical Repair, Obstetrics and Gynecology, vol. 89, n. 2, pp. 311-318 (Feb. 1997).

Webster, George et al., Voiding Dysfunction Following Cystourethropexy: Its Evaluation and Management, The Journal of Urology, vol. 144, pp. 670-673 (Sep. 1990).

Winter, Chester C., Peripubic Urethropexy for Urinary Stress Incontinence in Women, Urology, vol. XX, No. 4, pp. 408-411 (Oct. 1982).

Winters et al., Abdominal Sacral Colpopexy and Adominal Enterocele Repair in the Management of Vaginal Vault Prolapse, Urology, vol. 56, supp. 6A, pp. 55-63 (2000).

Woodside, Jeffrey R. et al., Suprapubic Endoscopic Vesical Neck Suspension for the Management of Urinary Incontinence in Myelodysplastic Girls, The Journal of Urology, vol. 135, pp. 97-99 (Jan. 1986).

Zacharin, Robert et al., Pulsion Enterocele: Long-Term Results of an Abdominoperineal Technique, Obstetrics & Gynecology, vol. 55, No. 2, pp. 141-148 (Feb. 1980).

Zacharin, Robert, The Suspensory Mechanism of the Female Urethra, Journal of Anatomy, vol. 97, Part 3, pp. 423-427 (1963).

Zimmern, Phillippe E. et al., Four-Corner Bladder Neck Suspension, Vaginal Surgery for the Urologist, vol. 2, No. 1, pp. 29-36 (Apr. 1994).

"We're staying ahead of the curve" Introducing the IVS Tunneller Device for Tension Free Procedures, Tyco Healthcare, 3 pages (2002).

Advantage A/T™, Surgical Mesh Sling Kit, Boston Scientific, 6 pages (2002).

Capio™ CL—Transvaginal Suture Capturing Device—Transvaginal Suture Fixation to Cooper's Ligament for Sling Procedures, Boston Scientific, Microvasive®, 8 pages, (2002).

Gynecare TVT Tension-Free Support for Incontinence, The tension-free solution to female Incontinence, Gynecare Worldwide, 6 pages, (2002).

IVS Tunneller—A Universal instrument for anterior and posterior intra-vaginal tape placement, Tyco Healthcare, 4 pages (Aug. 2002).

IVS Tunneller—ein universelles Instrument fur die Intra Vaginal Schlingenplastik, Tyco Healthcare, 4 pages (2001).

McGuire™ Suture Buide, The McGuire™ Suture Guide, a single use instrument designed for the placement of a suburethral sling, Bard, 2 pages (2001).

SABRE™ Bioabsorbable Sling, Generation Now, Mentor, 4 pages (May 2002).

SABRE™ Surgical Procedure, Mentor, 6 pages (Aug. 2002).

Petros, et al., Further Development of the Intravaginal Slingplasty Procedure-IVS III—(with midline "tuck"), Scandinavian Journal of Urology & Nephrology, 1993, pp. 69-71.

IVS Tunneller, AMA, 4 pages (EAU 2001).

Mitek Brochure, Therapy of Urinary Stress Incontinence in Women using Mitek GIII Anchors, by Valenzio Mascio, M.D. (1993).

George D. Webster Female Urinary Incontinence, urologic Surgery by James Glenn, 3$^{rd}$ Edition (1983).

U.S. Appl. No. 11/202,315, filed Aug. 12, 2005, Neisz et al.

* cited by examiner

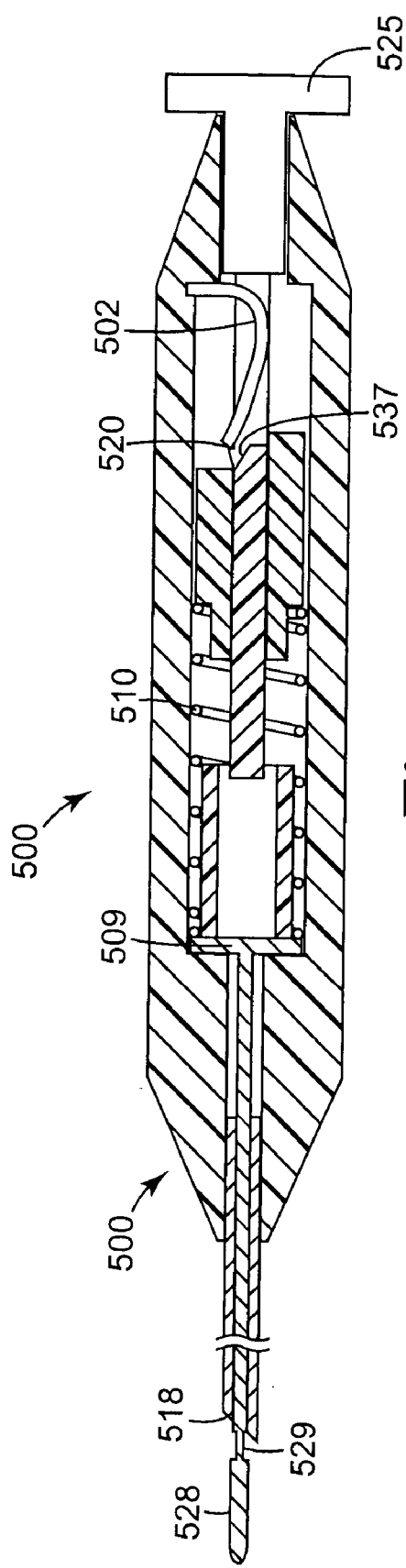
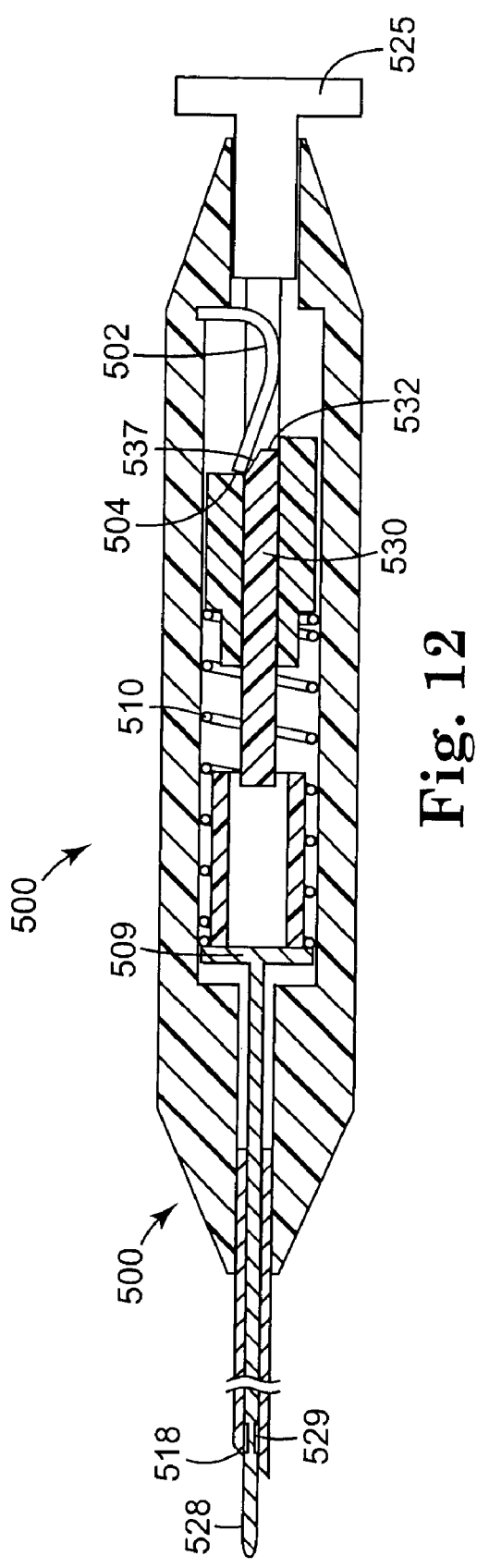
Fig. 11
Fig. 12

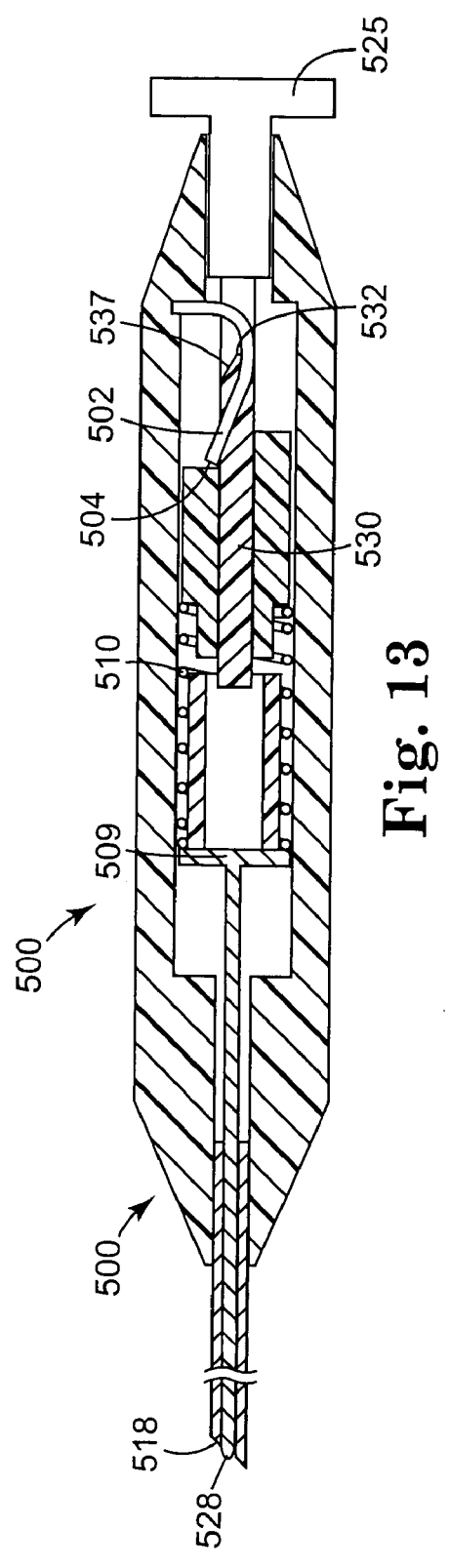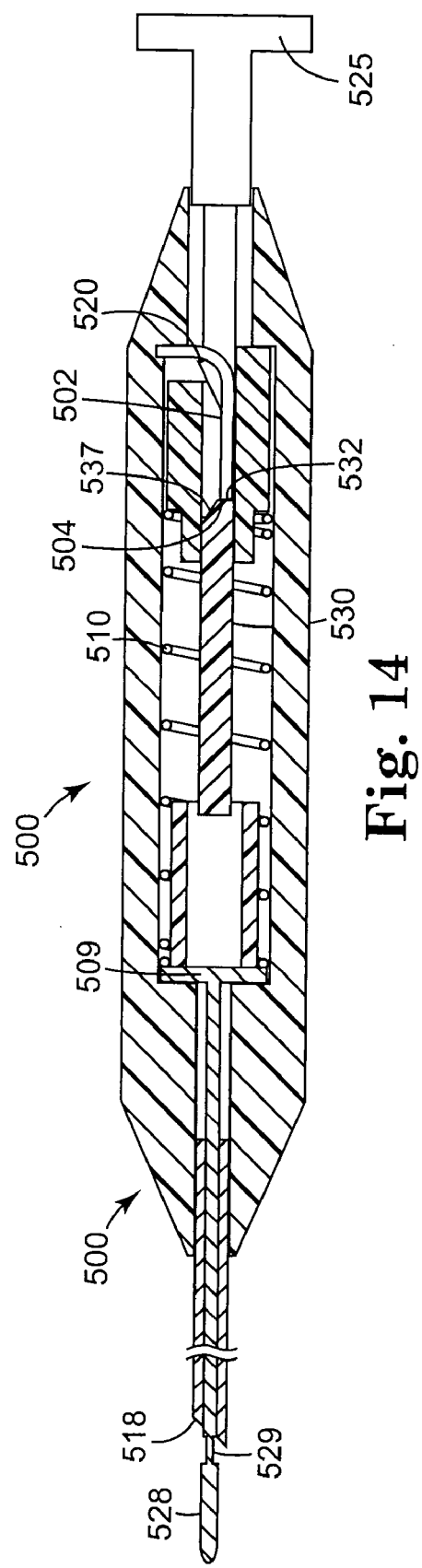

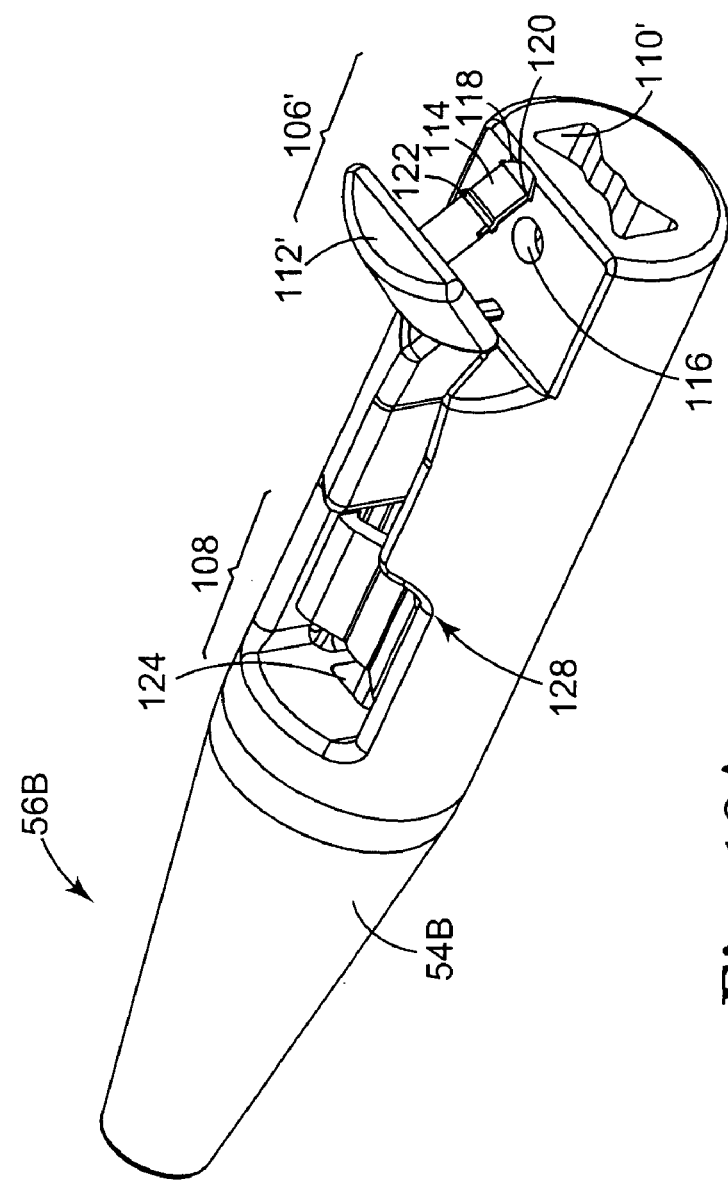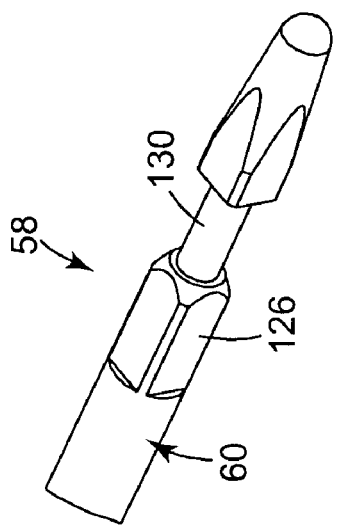
Fig. 18A

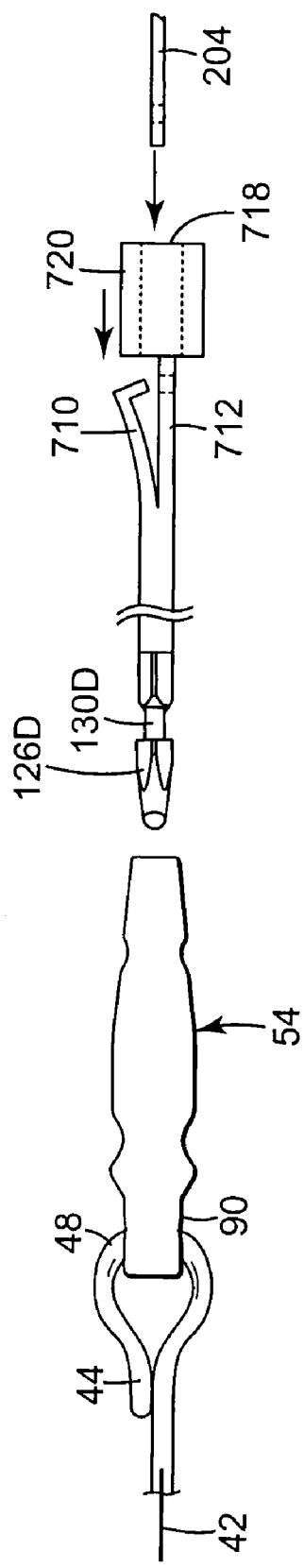
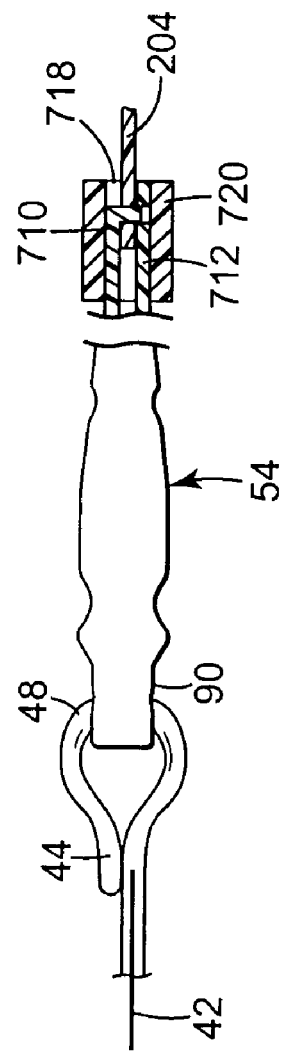
Fig. 27
Fig. 27A

SURGICAL ARTICLES AND METHODS

CROSS REFERENCE TO RELATED APPLICATIONS

This is a continuation of U.S. patent application Ser. No. 10/280,945, filed Oct. 25, 2002, now U.S. Pat. No. 7,048,682 which was a continuation of U.S. patent application Ser. No. 10/005,837 filed on Nov. 9, 2001 now abandoned (the '837 application), which was a continuation-in-part of U.S. patent application Ser. Nos. 09/917,443 filed Jul. 27, 2001, now U.S. Pat. No. 6,612,977 and 09/917,562 filed Jul. 27, 2001 now U.S. Pat. No. 6,652,450 ; the '837 application was a non-provisional of U.S. Provisional Application Ser. No. 60/263,472, filed Jan. 23, 2001; and U.S. Provisional Application Ser. No. 60/269,829, filed Feb. 20, 2001 now abandoned, and U.S. Provisional Application Ser. No. 60/281,350, filed Apr. 4, 2001; and U.S. Provisional Application Ser. No 60/295,068, filed Jun. 1, 2001, and Provisional Application No. 60/306,915, filed Jul. 20, 2001.

BACKGROUND

Urinary incontinence is a significant health concern worldwide. Incontinence may occur when the pelvic floor weakens. There are five basic types of incontinence: stress incontinence, urge incontinence, mixed incontinence, overflow incontinence and functional incontinence. There are a large number of surgical interventions and procedures for addressing incontinence.

Some surgeons are slow to adopt promising new surgical techniques for treating incontinence for a variety of reasons. Some are untrained or lack experience with the new procedure. Others are simply unwilling to try new instrumentation that seems unfamiliar.

Surgical centers and hospitals have an inventory of surgical instruments commonly used in surgery. Surgeons are trained with these stock surgical instruments at an early stage and become familiar with them. In the urology field, needles, suture passers and ligature carriers are commonly available and surgeons often develop significant experience and comfort with procedures that utilize them. Examples of such surgical instruments included Stamey needles, Raz needles, and Pereyra needles. See Stamey, *Endoscopic Suspension of the Vesical Neck for Urinary Incontinence in Females*, Ann. Surgery, pp. 465-471, October 1980; and Pereyra, *A Simplified Surgical Procedure for the Correction of Stress Incontinence in Women*, West. J. Surg., Obstetrics & Gynecology, pp. 243-246, July-August 1959. Some surgeons may reject a new technique simply because the instrumentation associated with the technique is unfamiliar.

A variety of surgical procedure options are currently available to treat incontinence. Depending on age, medical condition, and personal preference, surgical procedures can be used to completely restore continence. One type of procedure, found to be an especially successful treatment option for SUI in both men and women, is a sling procedure.

A sling procedure is a surgical method involving the placement of a sling to stabilize or support the bladder neck or urethra. There are a variety of different sling procedures. Descriptions of different sling procedures are disclosed in U.S. Pat. Nos. 5,112,344; 5,611,515; 5,842,478; 5,860,425; 5,899,909; 6,039,686, 6,042,534 and 6,110,101.

Sling procedures differ in the type of material used for the sling, the method of anchoring the sling material in the body and how the sling material is inserted in the body. The time required for a surgical procedure varies, but is preferably as short as possible. This factor is frequently reported in urology and gynecology literature. See Atherton M. J., et al., *A Comparison of Bladder Neck Movement and Elevation After Tension-free Vaginal Tape and Colposuspension*, British Journal of Obstetrics and Gynaecology, November 2000, Vol. 17, p. 1366-1370, Nilsson et al, *The Tension-free Vaginal Tape Procedure is Successful in the Majority of Women with Indications for Surgical Treatment of Urinary Stress Incontinence*, British Journal of Obstetrics and Gynaecology, April 2001, Vol. 108, P. 414-419; and Ulmsten et al., *An Ambulatory Surgical Procedure Under Local Anesthesia For Treatment of Female Urinary Incontinence*, Int. Urogynecol. J. (1996), v. 7, pps. 81-86.

Although serious complications associated with sling procedures are infrequent, they do occur. Complications include urethral obstruction, development of de novo urge incontinence, hemorrhage, prolonged urinary retention, infection, and damage to surrounding tissue and sling erosion.

The Tension-free Vaginal Tape (TVT) procedure (available from Ethicon, of N.J.) utilizes a Prolene™ nonabsorbable, polypropylene mesh. The mesh is a substantially flat, rectangular knitted article. The mesh includes a plurality of holes that are sized to allow tissue ingrowth to help avoid infection. A plastic sheath surrounds the mesh and is used to insert the mesh. During the sling procedure, incisions are made in the abdominal (i.e. suprapubic) area and in the vaginal wall. Two curved, relatively large (5 mm or larger) needle-like elements are each connected to an end of the vaginal sling mesh. A sling-free, sharp tip end of one of the needle-like elements is initially pushed through the vaginal incision and into the paraurethral space. Using a handle attached to the needle, the needle is angulated laterally (for example, to the right) to perforate the endopelvic fascia, guided through the retropubic space and passed through the abdominal incision. The handle is disconnected and the needle is then withdrawn through the abdominal wall, thereby threading a portion of the sling through the tissue of the patient. The handle is then connected to the other needle and the technique is repeated on the contralateral side, so that the mesh is looped beneath the bladder neck or urethra. The sling is positioned to provide appropriate support to the bladder neck or urethra. At the end of the procedure, the sling ends are cut at the abdominal wall, the sheath is removed and all incisions are closed.

Complications associated with the TVT procedure and other known sling procedures include injury to blood vessels of the pelvic sidewall and abdominal wall, hematomas, urinary retention, and bladder and bowel injury due to passage of large needles. Further, a separate cystoscopy procedure is usually required in order to confirm bladder integrity or recognize a bladder perforation after each insertion of the needle-like element. One serious disadvantage of the TVT procedure, particularly for surgeons unfamiliar with the surgical method, is the lack of information concerning the precise location of the needle tip relative to adjacent pelvic anatomy. A cadaver study indicated that the TVT needle is placed in close proximity to sensitive tissue such as superficial epigastric vessels, inferior epigastric vessels, the external iliac vessel and the obturator. See, Walters, Mark D., *Percutaneous Suburethral Slings: State of the Art*, presented at the conference of the American Urogynecologic Society, Chicago (October 2001).

If the TVT needle tip is allowed to accidentally pass across the surface of any blood vessel, lymphatic duct, nerve, nerve bundle or organ, serious complications can arise. These shortcomings, attempts to address these shortcomings and other problems associated with the TVT procedure are disclosed in PCT publication nos. PCT WO 00/74613 and PCT WO 00/74594.

Additional problems are associated with the TVT and other sling procedures. Removal and reuse of the handle of the TVT product is a cumbersome, time consuming process, requiring the surgeon to manually rotate the handle until the handle is unscrewed from the needle. Reusing the handle presents a contamination risk, particularly if the handle and screw threads are not properly cleaned and sterilized after use on the patient.

BRIEF SUMMARY

The present invention includes surgical instruments and implantable articles for urological applications, particularly incontinence surgical procedures.

The present invention is also directed to surgical kits for use in surgical procedures for treating incontinence, and improved surgical procedures for treating incontinence. The present invention can afford increased convenience for surgeons with the attendant advantages for the patient. The present invention can also exploit existing surgeon training and preferences to contribute to better surgical outcomes. Surgical procedures utilizing the present invention have the capacity to be shorter with concomitant advantages enjoyed by patients and the healthcare system.

In one aspect, the present invention comprises a surgical kit or assembly of surgical instruments for treating incontinence comprising an implantable material (e.g. a sling), at least one of a first type of needle, and at least one of a second type of needle. The first type of needle is different than the second type of needle. For example, one needle could be straight and the other curved, or one needle may be larger or longer than the other needle or shaped differently. A variety of different types of needles are described herein. Providing different types of needles can afford the surgeon options that are unavailable with existing surgical kits.

The needles in the kit need not serve the same purpose. For example, one needle may comprise a relatively small profile (e.g. less than about 3.5 mm diameter in cross section) guide needle, and the other needle may comprise a larger sling transport needle. The guide needle may be initially inserted suprapubically (e.g. through an abdominal incision) and then guided through a vaginal incision. The larger sling transport needle can then be associated with the guide needle (e.g. with an optional adapter or dilator) and then guided upward through the body of a patient (first through the vaginal incision and then through the suprapubic incision) by the guide needle.

In another aspect, the invention comprises a kit with a first type of sling material, a second type of sling material, and at least one needle for inserting a sling material. The sling materials can comprise synthetic or non-synthetic sling materials. In one embodiment, the sling materials can be both synthetic materials, but different types of synthetic materials (e.g. a polypropylene mesh material and a silicone coated material). There are also many different types of non-synthetic materials contemplated herein. Optionally, instead of having a non-synthetic sling material that has short term shelf life relative to the rest of the elements in the kit, the kit may include an accessory to afford construction of a sling from two different materials. This enables the surgeon to customize a hybrid or composite sling from different materials (e.g. from different packages) to exploit the different properties of the materials and to coordinate them with the intended physiological environment.

Another kit according to the present invention includes an implantable material (e.g. a sling), a needle for inserting the sling, and a first and second type of handle for use in the surgical procedure. A variety of different types of handles are contemplated herein.

The present invention also includes articles useful in urological surgical procedures. The present invention includes an adapter comprising a body portion having first and second opposite end portions. The first end portion has surfaces for associating the article with a needle. The second end portion has a sling associator for associating the article with a sling. The sling associator can comprise a universal adapter for connecting a surgical needle with different types of sling materials (e.g. synthetic or non-synthetic). The adapter allows the surgeon to select one of the many options of sling materials available so that the remaining components of the surgical kit may be utilized to implant any sling material.

The present invention also includes a needle converter for use with a sling assembly having an adapter or dilator. The adapter or dilator has surfaces for associating with a first type of needle (e.g. a specialized needle in a kit). The needle converter comprises a first end portion having surfaces that are sized and shaped to engage complementary surfaces in the passageway of the dilator to associate the needle converter with the dilator. The needle converter has a second end portion that is generally opposite the first end portion. The second end portion has a means for attaching the needle converter to a second type of needle that is different than the first type of needle. The needle converter allows the dilator of a sling assembly to be attached with a needle that is commonly used in surgical procedures for treating urological disorders (e.g. a Stamey needle). Thus, the needle converter allows a surgeon to connect a sling assembly with a preferred, standard needle.

The present invention also includes novel slings and sling assemblies. The slings may be conveniently implanted without the use of bone anchors. A sling according to the present invention comprises a synthetic surgical mesh (e.g. polypropylene) having first and second ends and a plurality of holes that are sized and shaped to afford tissue ingrowth. The assembly includes a removable synthetic insertion sheath situated about the surgical mesh. At least one suture is operatively associated with the surgical mesh and extends beyond the first end of the surgical mesh. At least one other suture is operatively associated with the surgical mesh and extends beyond the second end of the surgical mesh. The sutures are adapted to be associated with a surgical needle. For example, the sutures may be tied to a needle that has a hole in it or placed in a suture passageway of a ligature carrier.

Another sling according to the present invention comprises a synthetic surgical mesh (e.g. polypropylene) having a plurality of holes that are sized and shaped to afford tissue ingrowth. The assembly has a removable synthetic insertion sheath situated about the surgical mesh. The sheath has first and second ends. At least one suture is operatively associated with the insertion sheath and extends beyond the first end of the insertion sheath. At least one other suture is operatively associated with the insertion sheath and extends beyond the second end of the insertion sheath. The sutures in this embodiment are also adapted to be associated with surgical needles.

The novel slings may be used in novel surgical procedures according to the present invention. The novel surgical procedures comprise the steps of i) providing a novel sling according to the present invention, ii) creating at least one vaginal incision, ii) creating at least one suprapubic incision, iii) passing a leading end of a needle initially through a suprapubic incision and then through the vaginal incision on one side of the patient's urethra, iv) passing a leading end of a needle initially through a suprapubic incision and then through the vaginal incision on the other side of the patient's urethra, v) attaching the first suture to the leading end of a needle, vi) attaching the second suture to the leading end of a needle, vii) implanting the sling by moving the leading end of a needle from the vaginal incision toward a suprapubic incision, and viii) then removing the synthetic insertion sheath.

Another surgical procedure according to the present invention includes the use of a plurality of needles with different purposes. A novel surgical procedure includes the steps of i) providing a surgical kit comprising at least one guide needle, and at least one sling transport needle with a tip, a sling attached to the sling transport needle, and an adapter having tip receiving surfaces for receiving the tip of the sling transport needle, ii) creating at least one vaginal incision, iii) creating at least one suprapubic incision, iv) initially passing the guide needle through the suprapubic incision and then through the vaginal incision, v) attaching the adapter to the needle, vi) placing the tip of the sling transport needle in the tip receiving surfaces of the adapter, and vii) guiding the sling transport needle from the vaginal incision to the suprapubic incision with the guide needle to implant the sling. This procedure allow the surgeon to exploit the control provided by the smaller guide needle to avoid sensitive anatomical structures while retaining the benefit of the sling transport needle.

The present invention also includes kits having the novel surgical instruments, accessories, articles and slings described herein, and surgical procedures that utilize the novel structures.

BRIEF DESCRIPTION OF THE DRAWINGS

Other features and advantages of the present invention will be seen as the following description of particular embodiments progresses in conjunction with the drawings, in which:

FIGS. 11-14 are side views of another embodiment of needle for optional use in a kit according to the present invention, wherein FIG. 11 shows the needle with a blunt member in an unlocked, extended position that is extended beyond a sharp surface, FIG. 12 shows the sharp surface and blunt member as the blunt member is initially deflected by tissue;

FIG. 13 illustrates the blunt member deflected to substantially the level of the sharp surface, such as when the needle encounters significant resistance from tissue; and FIG. 14 shows the blunt member in a locked, extended position after the resistance associated with the tissue ends and a spring has returned the blunt member to the extended position;

FIG. 18A is a perspective view showing another embodiment of an adapter for associating a needle with a sling according to an aspect of the present invention, and an end portion of a needle;

FIG. 21A is a perspective view showing a sling constructed from a material different than the material shown in FIG. 21;

FIG. 21B is a side view of a suture anchor for use in an optional sling according to the present invention;

FIG. 27 is a side view of a sling assembly, needle converter and needle in a disassembled condition;

FIG. 27A shows the elements of FIG. 27 in an assembled condition;

FIGS. 30 through 33 are perspective views sequentially showing the insertion of a needle suprapubically in accordance with one aspect of the present invention, wherein:

FIG. 30 shows the needle just passing an abdominal incision;

FIG. 31 illustrates the needle as the surgeon seeks to identify the tactile feel of the resistance provided in part by the posterior portion of the pubic bone;

FIG. 32 shows the needle as it passes along the posterior surface of the pubic bone which may be used as an anatomical guide for a surgeon as the needle approaches a vaginal incision;

FIG. 33 illustrates the needle as it passes out of a vaginal incision;

DETAILED DESCRIPTION

Figure 1:
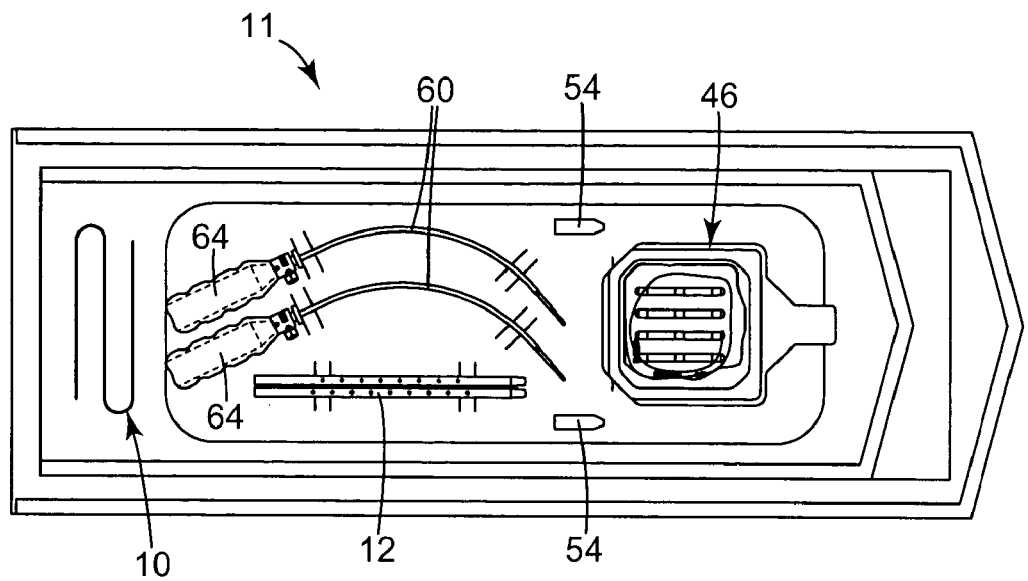
FIG. 1 is a top view of a surgical kit according to one aspect of the present invention.

The following description is meant to be illustrative only and not limiting. Other embodiments of this invention will be apparent to those of ordinary skill in the art in view of this description.

The present invention is directed to surgical instruments, and implantable articles for treating medical disorders such as incontinence or stress urinary incontinence (SUI) in both men and women. The present invention is also directed to improved surgical procedures that utilize the surgical articles. Although the invention as disclosed herein generally refers to SUI, treatment of other urological disorders, such as urge incontinence, fecal incontinence, mixed incontinence, overflow incontinence, functional incontinence, prolapse (e.g. vaginal and uterine), enteroceles (e.g. of the uterus or small bowel), rectoceles, cystoceles and other disorders are also included within the scope of the present invention. It is contemplated that the present invention may also be utilized in conjunction with concomitant procedures, such as, but not limited to, procedures for addressing cystocele, rectocele, vaginal prolapse and anatomic corrections.

In one aspect, the present invention comprises a surgical kit. FIG. 1A illustrates an example of such a kit 15. The kit 15 comprises an implantable material (e.g. a sling mesh provided as part of a sling assembly 46), at least one (preferably two) samples of a first type of needle 60, and at least one (preferably two) of a second type of needle 60A. The first type of needle 60 is preferably different than the second type of needle 60A.

As used herein, the term "needle" is used generally to describe a variety of surgical instruments including suture passers, ligature carriers, needles and the like. Typically, the needle will have an elongate body and a pair of ends. The needle facilitates passage through tissue, preferably from an abdominal incision to a vaginal incision or, alternatively from the vaginal incision to an abdominal incision. As used in this application, when it is said that one needle is of a different type than another needle, it is meant that the needles substantially differ in a feature that can potentially affect a surgical procedure for treating a urological disorder. Features that can be different according to the present invention include, but are not limited to the size of the needles, the length of the needles, the shape of the needles, the characteristics of an end of the needles (e.g. sharp or blunt surfaces, closed or open lumen), the capacity of the needle to operate with a bladder perforation detector or a means for avoiding perforations of the bladder, the material of the needles, whether the needles have the capacity to be tied to a suture, the strength of the needles, the cross sectional size (e.g. diameter) or shape of the needle, the presence of an integral handle, the presence of a bladder perforation detection feature, the degree that the needles are malleable, whether the needles are reusable or only provided for use on a single patient, the capacity of the needles to be sterilized by a particular sterilization procedure, whether the needles have surfaces that are sized and shaped to engage complementary surfaces on another surgical article, the capacity of the needle to deliver a medicament such as an anaesthetic, the capacity of the needle to include a lighting feature, whether the needles have a portion that is movable relative to remaining portions of the needle, and other features.

Figure 4:
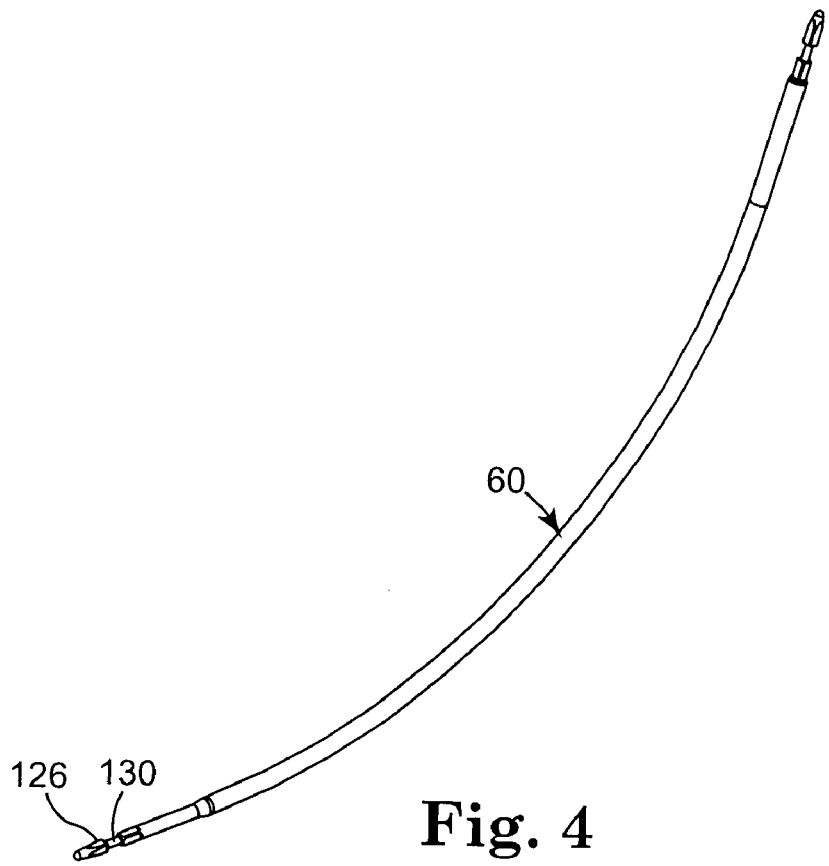
FIG. 4 is a perspective view of a needle with a curved portion for optional use in a kit according to the present invention.

FIG. 4 illustrates a curved needle 60. The needle 60 is preferably arc-shaped and includes end 58 and end 62. The ends or tip of the needle 60 are preferably not sharp, but may be tapered to afford easy passage through tissue while providing a blunt surface that avoids cutting sensitive tissue such as the bladder or urethra. In a preferred embodiment, the length of the needle 60 is approximately within the range of 16.5 cm to 24.1 cm (6.5 inches to 9.5 inches) and has a preferred external diameter of approximately 3.175 mm (0.125 inch). Preferably, the diameter of the needle 60 is small relative to the prior art to reduce tissue trauma.

The needle 60 is preferably made of a malleable, yet durable, biocompatible surgical instrument material such as, but not limited to, stainless steel (e.g. 316 stainless steel or 17-4 stainless steel), titanium, Nitinol, polymers, plastics and other materials, including combinations of materials. The needle 60 should have sufficient structural integrity to withstand the various forces (e.g. forces caused by dilator attachment, and penetration/passage of the needle 60 through the various tissues) without undergoing any significant structural deformation. Optionally, the needles 60 could be sufficiently malleable to allow a practitioner or user of the device to modify the needle 60 to a desired shape and, thereby, optimize the procedural approach.

Figure 3:
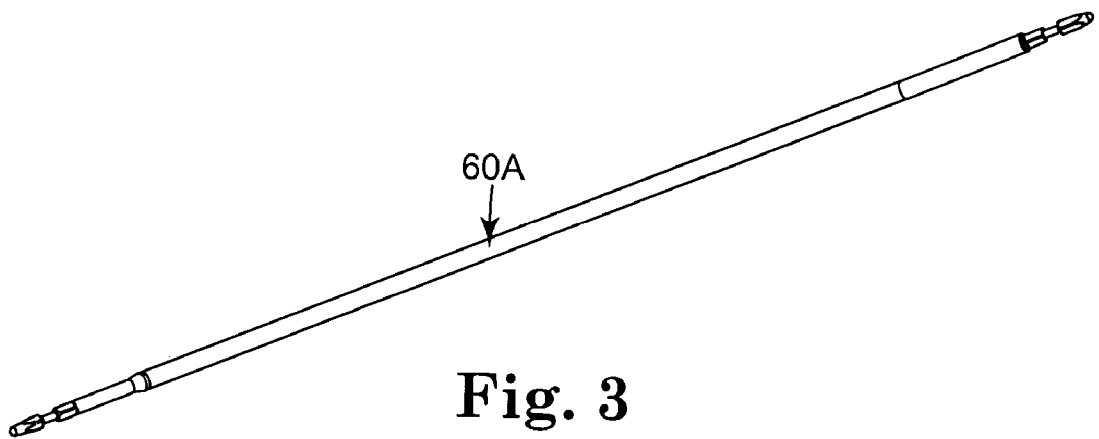
FIG. 3 is a perspective view of a substantially straight needle for optional use in a kit according to the present invention.

FIG. 3 illustrates a substantially straight needle 60A. Some surgeons prefer a curved needle to a straight needle for some urological procedures. Others prefer straight needles to curved needles. Providing the surgeon the option to use either needle from a surgical kit can increase the convenience for the surgeon and can match the skills possessed by a particular surgeon with the surgical instrumentation provided in the surgical kit.

Figure 6:
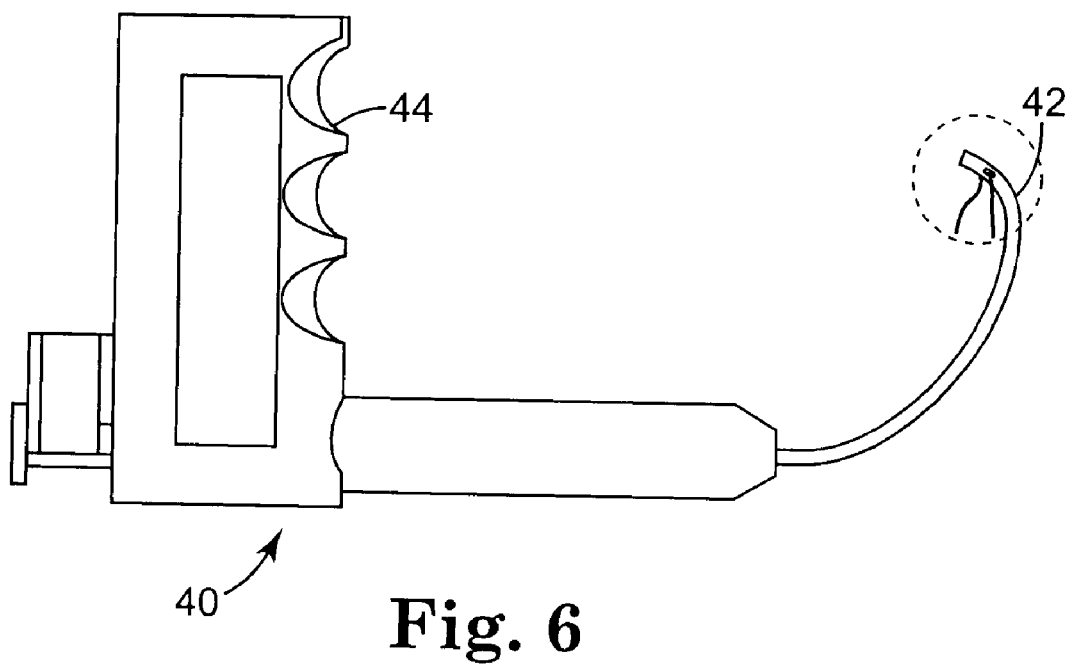
FIG. 6 is a side view of another embodiment of needle for optional use in a kit according to the present invention.
Figure 6A:
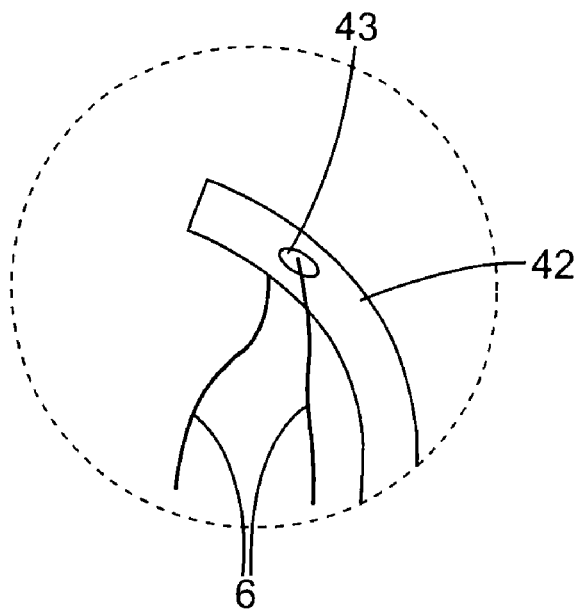
FIG. 6a is an enlarged side view of a portion of FIG. 6.
Figure 7:
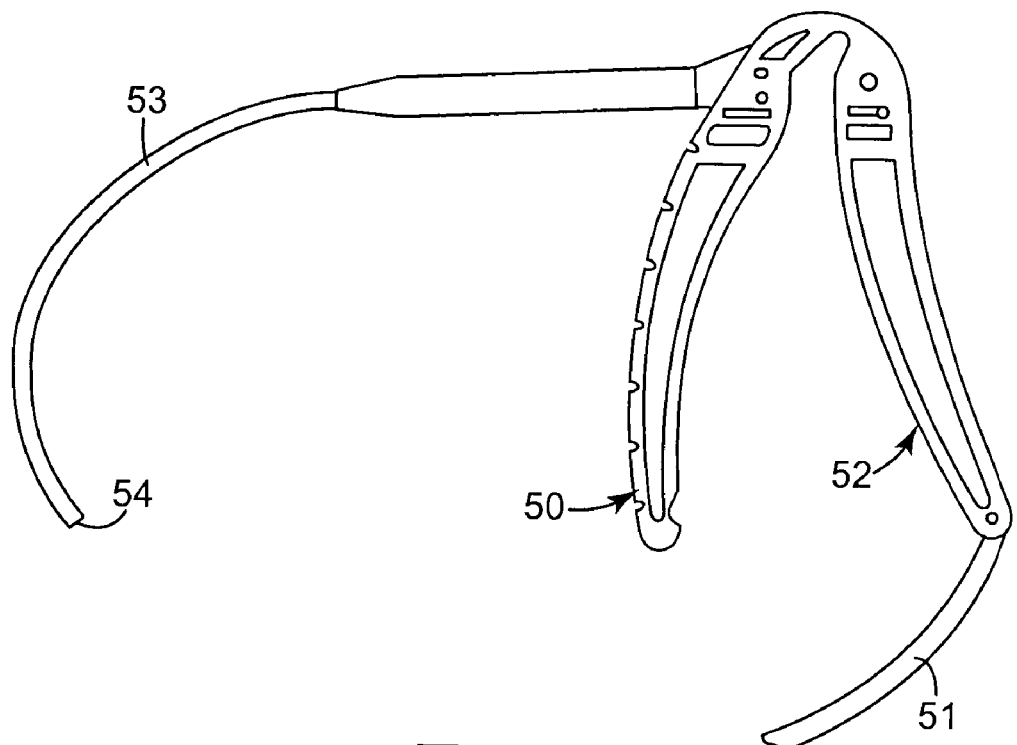
FIG. 7 is a side view of another embodiment of needle for optional use in a kit according to the present invention.
Figure 8:
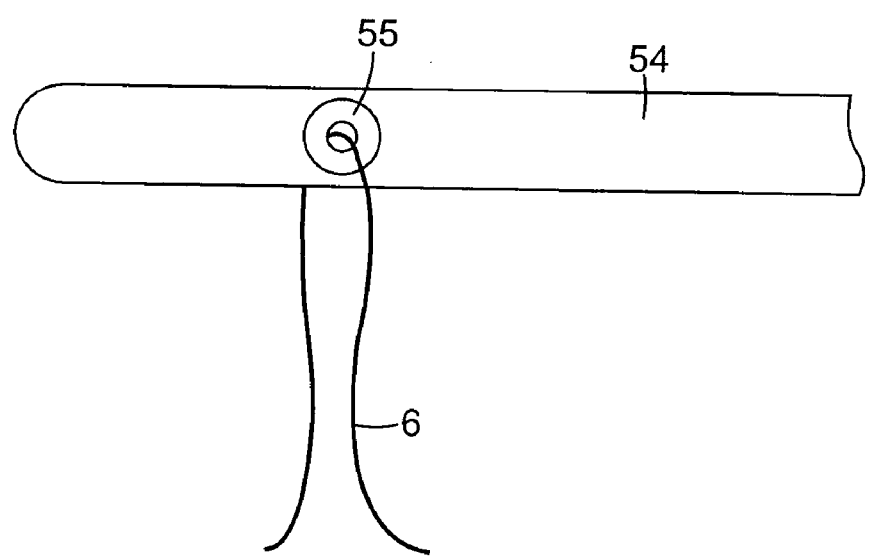
FIG. 8 is a side view of an end portion of a needle for optional use in a kit according to the present invention.

FIG. 6 illustrates a different type of curved needle 40 with integral handle 44. The leading end portion 42 of the needle 40 includes a passageway (hole 42) for receiving a suture 6 used during the surgical procedure. FIGS. 7 and 8 illustrate a curved needle assembly 50 with a curved portion 53, an end 54, a movable handle 52 and a handle lock or stabilizer 51.

Figure 9:
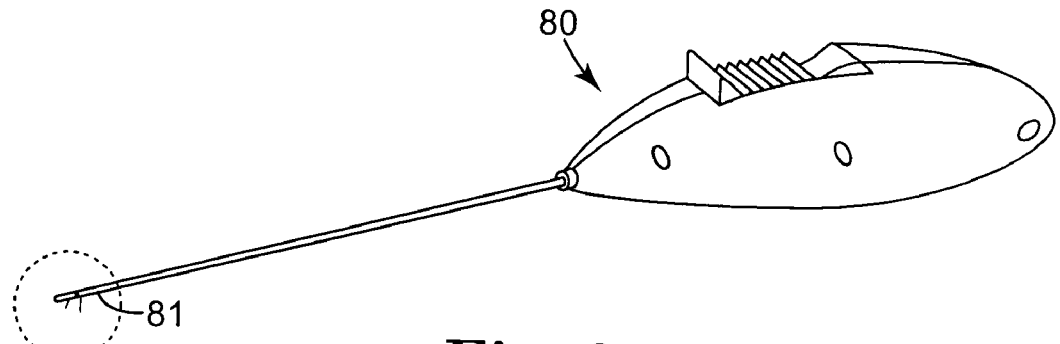
FIG. 9 is a side view of another embodiment of needle for optional use in a kit according to the present invention.
Figure 9A:
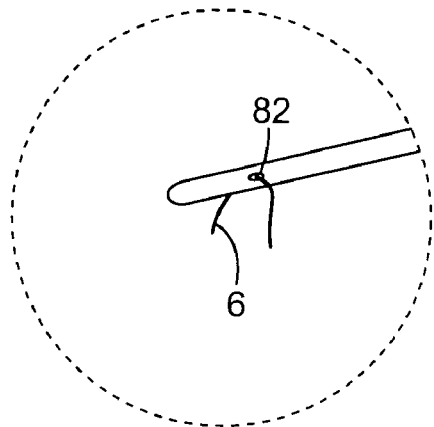
FIG. 9A is an enlarged view of a portion of FIG. 9.
Figure 10:
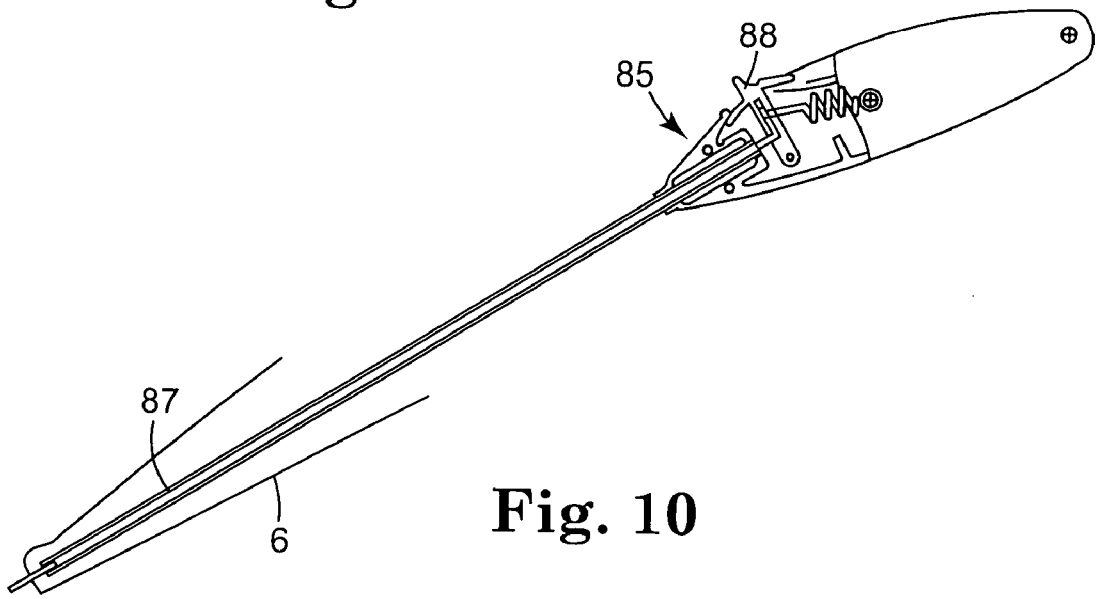
FIG. 10 is a side view of another embodiment of needle for optional use in a kit according to the present invention.

FIGS. 9, 9A and 10 show a different type of needle assembly 80 comprising an end portion 81 with a passageway 82 for receiving a suture 6. The passageway 82 for receiving a suture 6 is illustrated as a hole. Alternatively, the passageway could include a slot, slit or other shape for receiving and securely grasping the suture 6.

The needle assembly 80 includes shaft 87. The end portion 81 and passageway 82 are placeable within the sheath 87. Preferably the end portion 81 is blunt and free of any sharp surfaces. The needle 80 also includes a mechanism 85 that is capable of moving the blunt end portion 81 between i) an extended position with the suture passageway 82 extending beyond the end of the outer sheath member 87 so that the suture passageway can conveniently receive a suture 6, and ii) a retracted position with the blunt end portion spaced closer to the end of the outer sheath member 87 than in the extended position and for securely holding a suture placed within suture passageway 82. Preferably, in the retracted position, the passageway 82 is completely within the sheath member 87 to securely hold the suture 6 to the needle 80 and to resist separation of the suture 6 and needle 80. A button 88 is used to conveniently move the elements between the extended and retracted positions. Preferably, a spring is utilized to bias the elements toward the retracted position.

FIGS. 11-14 illustrate another embodiment of needle 500 for optional use in a kit according to the present invention. The needle 500 includes a handle and a sheath that remain relatively stationary. The sheath includes a relatively sharp surface 518 for cutting tissue. The needle 500 also includes an inner member that is movable relative to the handle. The inner member has a blunt end 528. Preferably, the movable member also includes a suture passageway 529. Alternatively, the inner member could include a means for snapping onto a dilator as described more fully below.

FIG. 11 shows the needle 500 with a blunt member 528 in an unlocked, extended position that is extended beyond sharp surface 518. In this position, the blunt member 528 protects tissue from the sharp surface 518 but the blunt member 528 is free to deflect inwardly when the needle is pressed against tough tissue (e.g. abdominal fascia). FIG. 12 shows the sharp surface 518 and blunt member 528 as the blunt member 528 is initially deflected by tissue.

FIG. 13 illustrates the blunt member 528 deflected to substantially the level of the sharp surface 518, such as when the needle encounters significant resistance from tissue. In this condition, the sharp surface may now be exploited to cut through the tough tissue to avoid the sudden needle lurch associated with a blunt ended, prior art needle. FIG. 14 shows the blunt member 528 in a locked, extended position after the resistance associated with the tissue ends and spring 510 has returned the blunt member 528 to the extended position.

Preferably, the needle 500 has a locking means for locking the blunt end portion 528 in the extended position to avoid injuring tissue once the needle passes through the tough tissue. The locking means preferably comprises a locking leaf spring 502. One end of the leaf spring 502 is preferably attached to the handle and the other end of the leaf spring 502 is movable between a locking position (FIG. 14) and a release position (FIGS. 11-13).

The inner movable member with blunt end 528 includes a spring shoulder 509, and extension arm 530 with leaf spring cam surface 537 and blocking surface 532. When the needle 500 is initially pressed against the tissue to be cut, the leaf spring cam surface 537 cams the end of the leaf spring 502 off of a retaining lip 520 (described in more detail below). The blocking surface 532 is adapted to engage the end of the locking leaf spring 502 to lock the movable member in the extended position. Spring 510 biases the inner member toward the extended position. A floating spring attachment member is operatively associated with one end of the spring 510 and the other end engages spring shoulder 509 of the inner movable member.

The needle 500 also preferably includes a release mechanism for releasing the inner member with blunt end 528 from the locked position. The release mechanism includes a slidable button 525 assembly with a leaf spring retaining lip 520. The leaf spring retaining lip 520 is sized and shaped to retain the leaf spring in the release position shown in FIG. 11. The release mechanism also includes a deflection surface Oust adjacent retaining lip 520) to move the leaf spring from the locked position (FIG. 14) to the release position (FIG. 11) when the button 525 is pressed.

Figure 15:
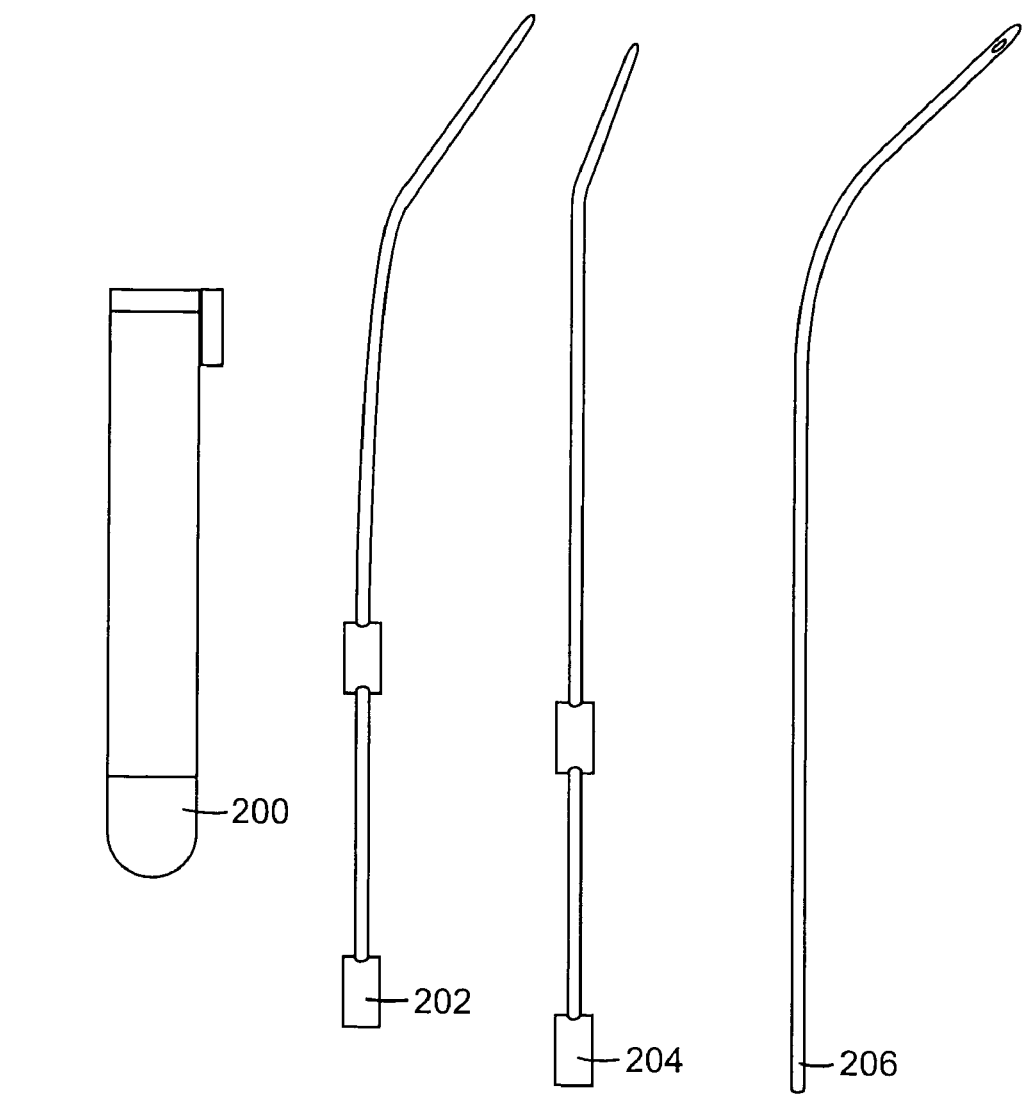
FIG. 15 is a side view of a handle and several different embodiments of needles adapted for use in the present invention.
Figure 16:
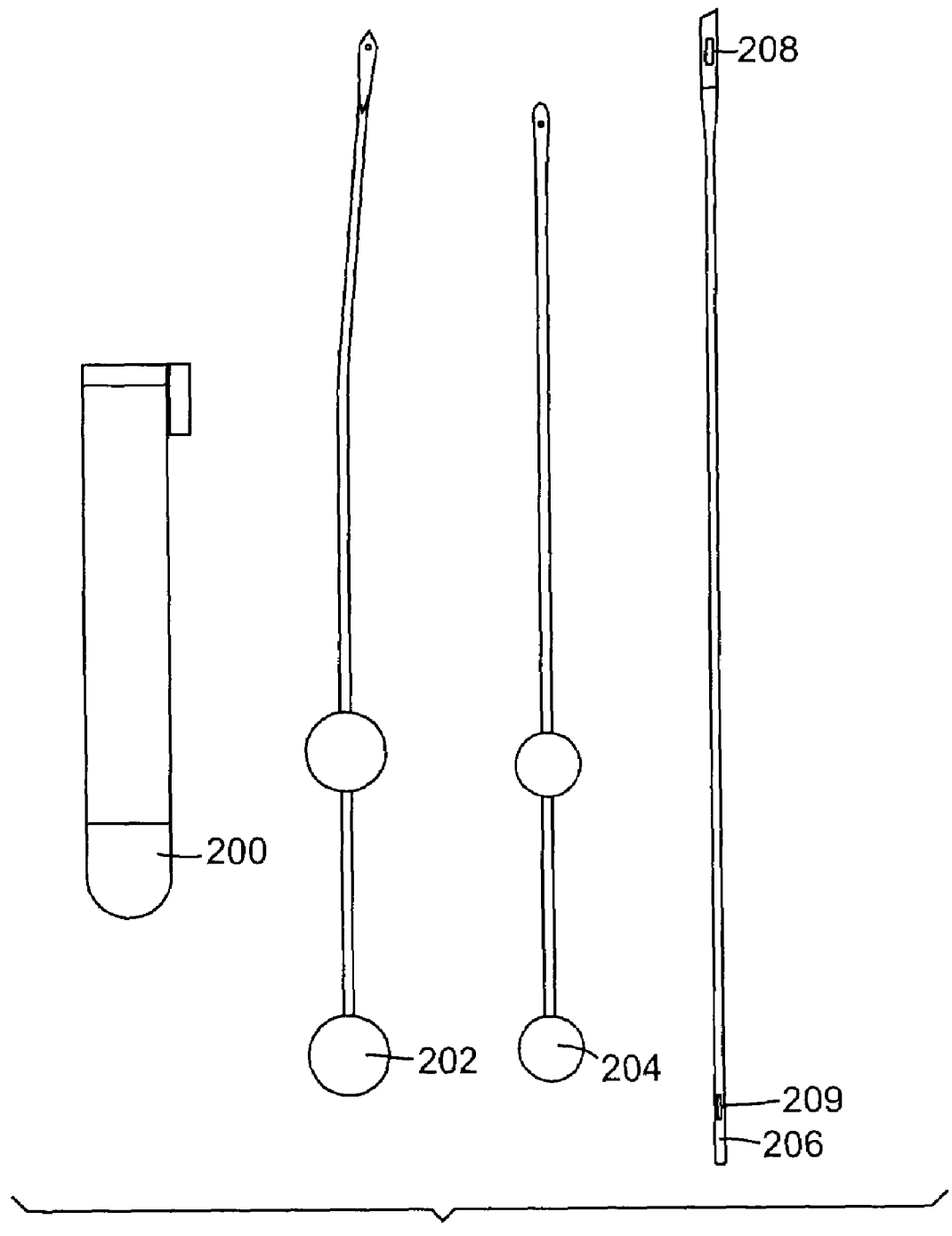
FIG. 16 is a top view of the handle and the needles of FIG. 15.
Figure 17:
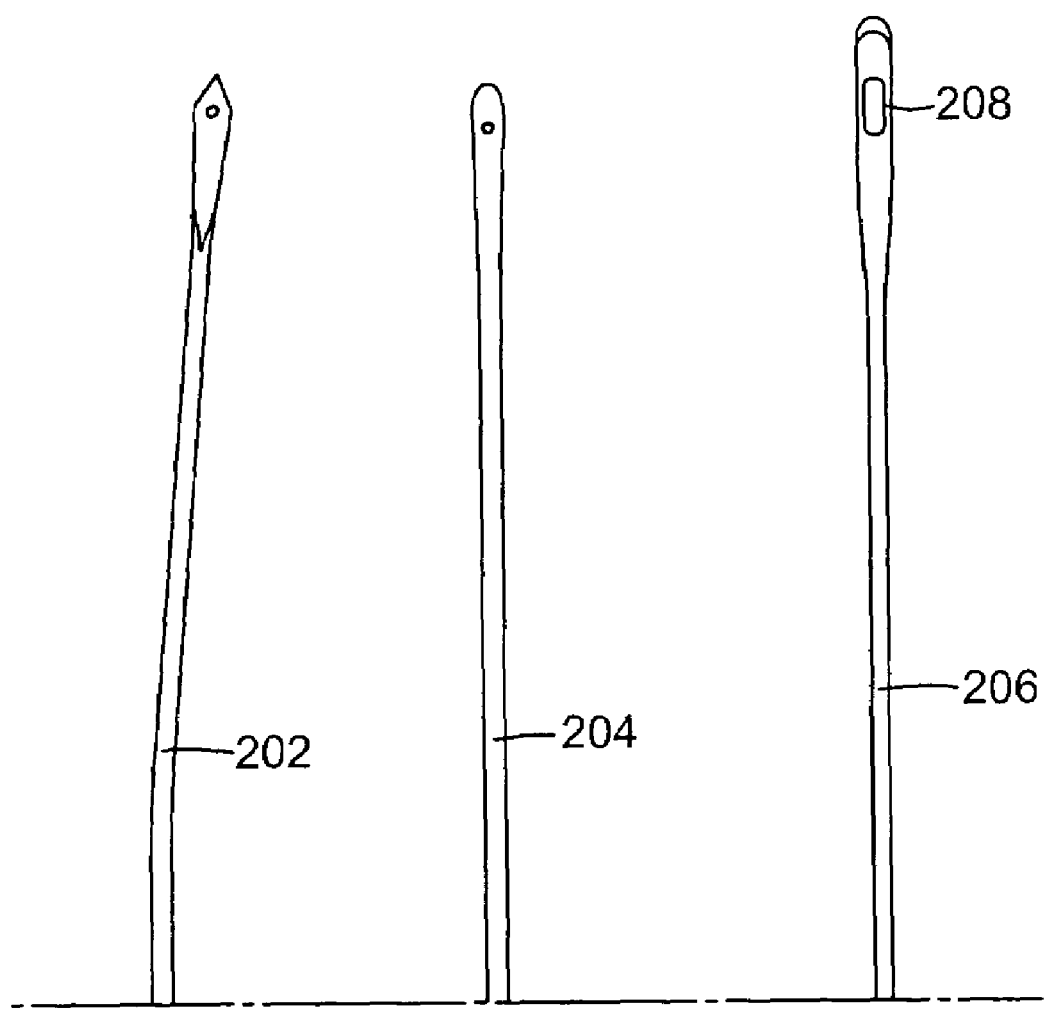
FIG. 17 is an enlarged view of the ends of the needles shown in FIG. 16.

FIGS. 15 through 17 illustrate additional examples of different types of needles for use in a kit according to the present invention. Needle 202 includes two substantially straight portions situated at a predetermined angle. The needle 202 has two substantially disc shaped integral handles, and a diamond-shaped, substantially flat end portion. The end portion includes a passageway. Needle 204 has two substantially straight portions at a predetermined angle that is different than the angle of needle 202. Needle 204 is also longer than needle 202 and has a different shaped end portion. Needle 206 has a straight and a curved portion. Needle 206 includes a substantially flat end portion with a passageway 208. A handle 200 with a set screw may be attached to the needle 206 (e.g. at complementary surface 209).

Needles 202, 204 and 206 are sized and shaped to be suitable for use in surgical procedures. The needles are particularly useful for treating urological disorders. Preferably, the needles are constructed from a strong biocompatible material such as stainless steel. They may be reusable and can be sterilized by steam sterilization procedures, including flash sterilization procedures commonly located close to the surgical location.

The different sizes and shapes of the needles provide a surgeon with the option to use a different needle depending upon the needs of a particular surgical procedure (e.g. size of the patient, previous surgical procedures, scarring, concomitant procedures, condition of the patient, and the anatomy of the patient, etc.).

Figure 38:
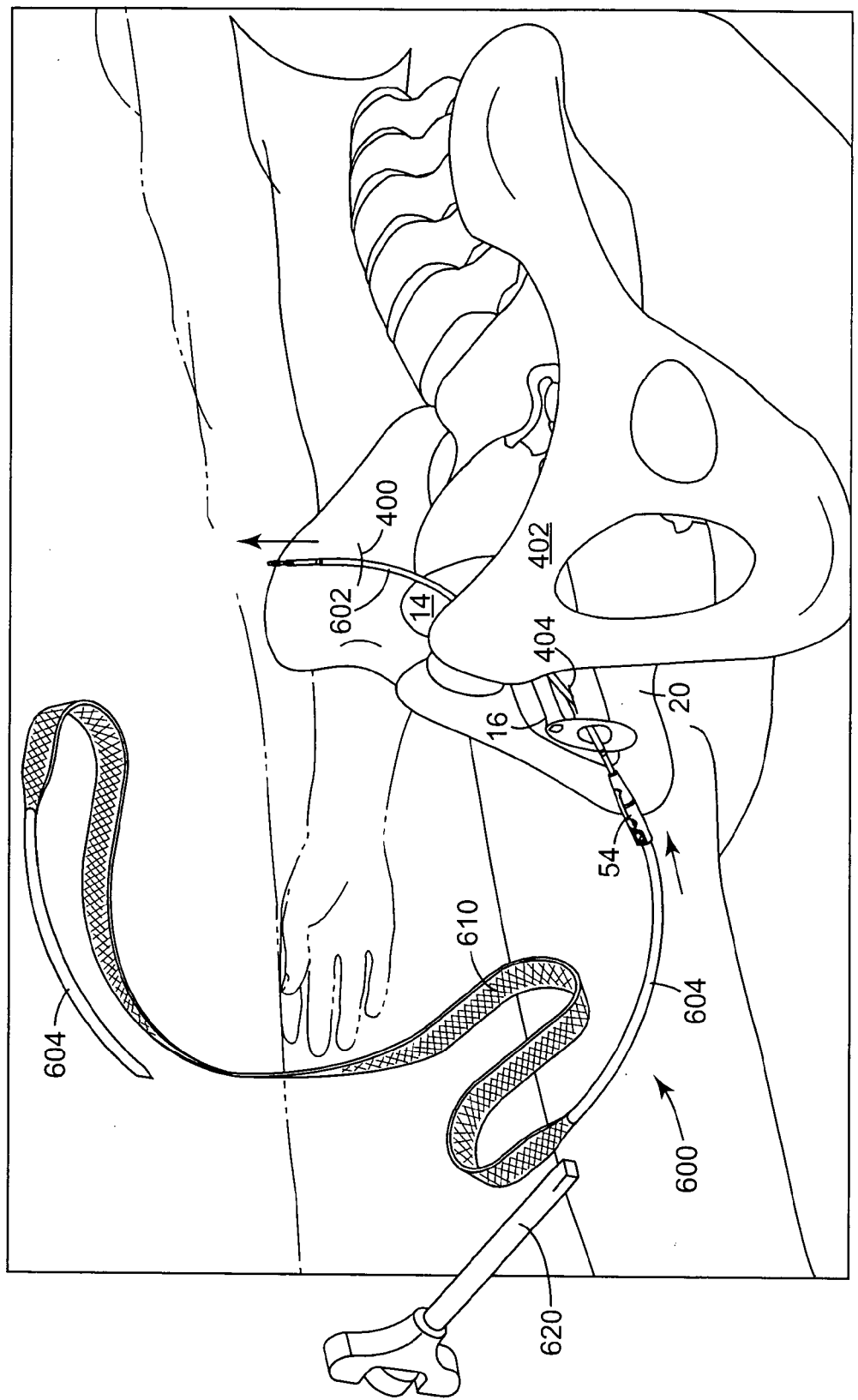
FIG. 38 is a perspective view of a small guide needle after it has been inserted suprapubically, an adapter connected to the small guide needle after the needle has been inserted suprapubically, and another large needle for implanting a sling that is inserted in an open end of the adapter in preparation for being guided through the patient by the small needle.

In another aspect of the present invention, the different types of needles need not serve the same purpose in a surgical procedure, but could serve a different purpose. FIG. 38 illustrates a surgical guide needle 602 (e.g. with a diameter of about 4 mm, or less, preferably about 3 mm) and a relatively larger sling transport needle 604 (e.g. with a diameter of 5 mm). Preferably, the sling transport member has a sling assembly 610 (e.g. a sling mesh and insertion sheath) attached thereto.

The guide needle 602 serves a different purpose than the surgical transport needle 604. The surgical guide needle 602 is preferably small and has a blunt tip. The blunt tip is initially inserted through an abdominal or suprapubic incision 400 and then through a vaginal incision 404. Inserting a small, blunt needle in this fashion provides the surgeon with addition control in maneuvering through the anatomy of a patent and in avoiding sensitive tissue.

A surgical kit according to an aspect of the present invention may include an adapter 54 on the end of needle 602. The sling transport needle 604 may optionally include a sharp tip. The adapter receives the tip of the needle 604. Pushing upward on the sling transport needle 604 with one hand while steering the tip of the needle 604 by holding guide needle 602 with the other hand is believed to provide better control over insertion of a prior art large needle that is initially inserted through the vaginal incision 404 and then through the suprapubic incision.

Alternatively, the adapter can include surfaces for firmly engaging and attaching to needle 604. Those surfaces can include mechanical interlocking structures, grasping structures or interlocking structures. Optionally, a biocompatible adhesive may be used to adhere the tip of sling transport needle 604 to the adapter.

Figure 40:
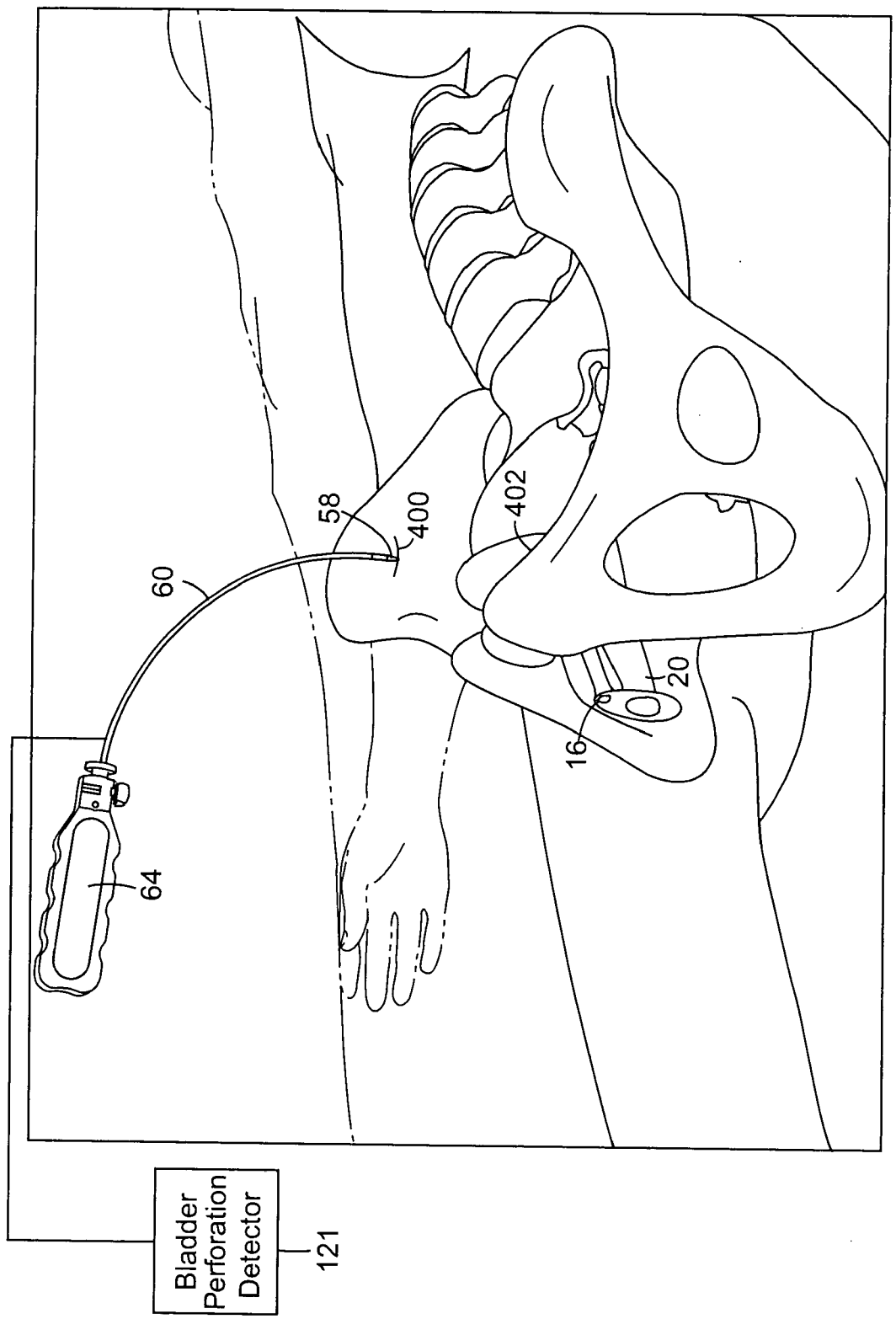
FIG. 40 is a perspective view of another needle according to the present invention that includes a schematic depiction of a feature of the needle.

FIG. 40 illustrates a needle 60 with a bladder perforation detector 121. A variety of means may be used as the bladder perforation detector. The needle perforation detector can include a ph sensor for determining whether the ph encountered by the needle is outside anticipated limits. For example, if the bladder has been perforated, fluid associated with such a perforation is likely to encounter the end 58 of the needle and change the ph encountered by the needle. The change in ph can be used to signal that the bladder has been perforated.

The bladder perforation detector 121 preferably signals an impending bladder perforation prior to its occurrence so that it prevents bladder perforations. For example, an object may be placed in the bladder 14 of the patient. The needle 60 and object can have complementary light source and detection means (e.g. a photoelectric sensor) for avoiding bladder perforations by the end 58 of the needle 60. For example, the object can include a light source and a light emitter. The needle 60 can include a light detector tuned to receive light emitted from the object. Preferably, the object emits light through the bladder 14 so that the needle 60 detects the light prior to perforating the bladder 14.

Alternatively, needle 60 may be associated with a light source and can emit light. In this embodiment, the object placed in the bladder includes a photosensitive detector/receptor and can be associated with an alarm and controller. The controller can set a threshold of light intensity detected. Above that threshold, an alarm may be used to warn a surgeon that the needle is in proximity to the bladder and that a bladder perforation may be impending. Optionally, the bladder may be filled with a photoconductive medium to enhance bladder perforation detection.

In another embodiment, the needle can have a resistance or capacitance detector capable of detecting the change in resistance encountered after the bladder is perforated. In another embodiment, an object can be placed in the bladder through the urethra. The needle can include a proximity sensor for detecting the proximity of the needle to the object. This type of needle can be constructed to be operatively associated with an alarm mechanism (e.g. audible, visual or tactile) that informs the surgeon that the needle is in proximity to the object that is placed in the bladder. Such a device is believed to avoid bladder perforations as, upon sensing the alarm, the surgeon may change the path of the needle to a path that is away from a close proximity to the bladder. Alternatively, the proximity of the needle and an object in the bladder can close a circuit and actuate an alarm. The alarm may be audible, visual or tactile to the user by an integral part of the needle or a separate device integrated into the system.

In another aspect of the present invention, a needle may optionally include the capacity to deliver a medicament (e.g. anesthesia) during the surgical procedure. For example, the needle may be hollow with an open end. The needle may have a connector for associating with a medicament reservoir and delivery mechanism (e.g. a syringe). As another alternative, the needle may comprise a means for connecting to a light source to enhance visibility or for being monitored by a light detector placed in the bladder (e.g. to avoid bladder perforations).

Figure 1A:
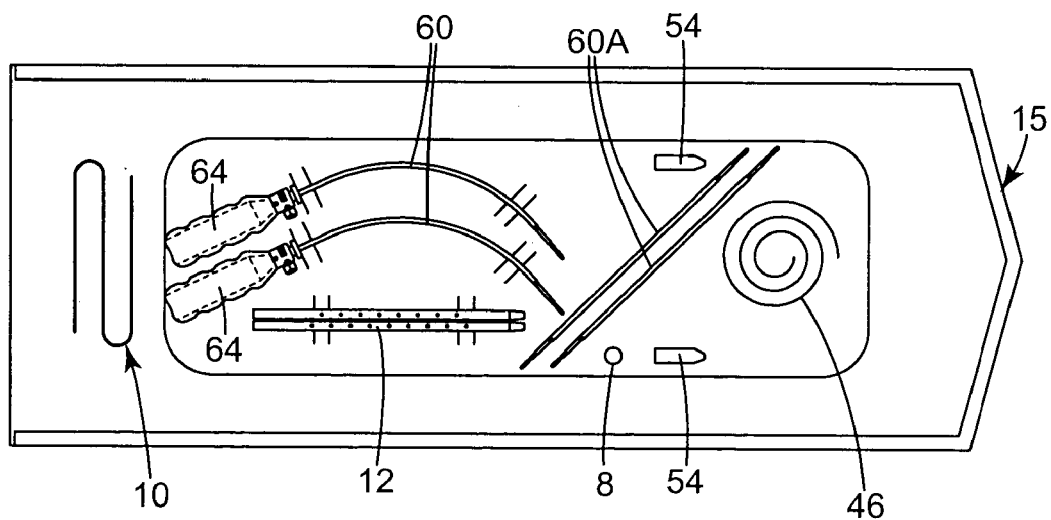
FIG. 1A is a top view of a surgical kit according to another aspect of the present invention.

Referring to FIG. 1, in another aspect the present invention comprises a surgical kit 11 comprising a first type of sling material (e.g. as part of the sling assembly 46), a second type of sling material 10, and at least one needle (e.g. 60). As used herein, the terms "sling" or "article" or "mesh" or the phrases "implantable material" or "implantable article" or "sling mesh" (or combinations thereof) are used generally to describe a variety of materials including synthetic and non-synthetic materials. Typically, the implantable article will be elongate and substantially flat. It can be used as a hammock, sling, strip or support member. As used in this application, when it is said that one sling material is of a different type than another sling material, it is meant that the materials substantially differ in a feature that can potentially affect a surgical procedure for treating a urological disorder. Features that can be different according to the present invention include, but are not limited to the ability of the sling to avoid infections or tissue erosion, the shelf life of the product, the type of material, the shape of the material, the presence of a sling tensioning member (e.g. as disclosed in U.S. patent application Ser. No. 09/917,562, filed Jul. 27, 2001), the present of a sling adjustment feature as described in U.S. patent application Ser. No. 10/004,185 filed Oct. 30, 2001 which claims priority to U.S. Provisional Application No. 60/327,075 filed Oct. 3, 2001, sling material treatment, the porosity of the sling material, the shape of the sling material, the sling length, the strength of the material, the elastic property of the material, the potential for tissue ingrowth, the biocompatibility of the material, and the presence or absence of an insertion sheath.

While the slings are preferably rectangular for treating SUI in females, other shapes are also contemplated. Depending on the treatment addressed (e.g. to provide hammock support for the bladder or bladder neck, or to address a rectocele, enterocele or prolapse) the slings may be any of a wide variety of shapes. As an example, the sling may be of the general shape of the slings described and shown in Moir et al., *The Gauze-Hammock Operation*, Journal of Obstetrics and Gynaecology of the British Commonwealth, Volume 75, No. 1, Pps. 1-9 (1968).

Suitable non-synthetic materials include allografts, homografts, heterografts, autologous tissues, cadaveric fascia and fascia lata. Some surgeons believe that non-synthetic materials are i) more consistent from lot to lot in terms of material characteristics, as opposed to some synthetic slings whose characteristics may be believed to vary, ii) less likely to cause tissue erosion or are less likely to elicit an adverse reaction from the patient's foreign body response mechanism as the body is less likely to recognize a non-synthetic material as a foreign material, and iii) are less likely to be rejected by the body long term.

Suitably synthetic materials for a sling include polymerics, and plastics and any combination of such materials may also be used in a kit of the present invention. Commercial examples of such materials include Marlex™, Prolene™, and Vaskutek™. Other examples of suitable materials include those disclosed in U.S. patent application Ser. No. 09/939,098 filed Aug. 24, 2001 (the entire contents of which are herein incorporated by reference). Specific examples of synthetic sling materials include, but are not limited to polypropylene, polyethylene, nylon, PLLA and PGA. For example, some surgeons prefer synthetic materials because they believe such materials: i) are stronger and/or more durable than many non-synthetic materials (e.g. less likely to experience suture detachment failure), ii) have different elastic properties, iii) are more likely to afford desirable tissue ingrowth, iv) can be readily and effectively incorporated with desirable features such as antimicrobial agents, v) many non-synthetic sling materials are difficult to acquire, and vi) present no issues of cross contamination between species.

The sling material may be resorbable, absorbable or non-absorbable. Optionally portions may be absorbable and other portions may be non-absorbable.

In one aspect of the invention, the sling may comprise a mesh material. The mesh material comprises one or more woven, knitted or inter-linked filaments or fibers that form multiple fiber junctions throughout the mesh. The fiber junctions may be formed via weaving, knitting, braiding, bonding, ultrasonic welding or other junction forming techniques, including combinations thereof. In addition, the size of the resultant openings or pores of the mesh may be sufficient to allow tissue in-growth and fixation within surrounding tissue. As an example, not intended to be limiting, the holes may comprise polygonal shaped holes with diagonals of 0.132 inches and 0.076 inches. Holes much smaller than this are not preferred as they may facilitate bacterial colonization.

The quantity and type of fiber junctions, fiber weave, pattern, and material type influence various sling properties or characteristics. Non-mesh sling configurations are also included within the scope of the invention. As another example, not intended to be limiting, the mesh may be woven polypropylene monofilament, knitted with a warp tricot. The stitch count may be 27.5 courses/inch (+or −2 courses) and 13 wales/inch (+or −2 wales). The thickness of this example is 0.024 inches.

In another embodiment the sling material may have one or more substances associated therewith through a process such as coating. Examples of appropriate substances include, without limitation, drugs, hormones, antibiotics, antimicrobial substances, dyes, silicone elastomers, polyurethanes, radiopaque filaments or substances, anti-bacterial substances, chemicals or agents, including any combinations thereof. The substances may be used to enhance treatment effects, reduce potential sling rejection by the body, reduce the chances of tissue erosion, enhance visualization, indicate proper sling orientation, resist infection or other effects. For example, the sling may be coated by the process described in U.S. Pat. Nos. 5,624,704; 5,756,145; 5,853,745; 5,902,283 and 6,162,487 (the entire contents of which are hereby incorporated by reference).

Figures 2, 2A:
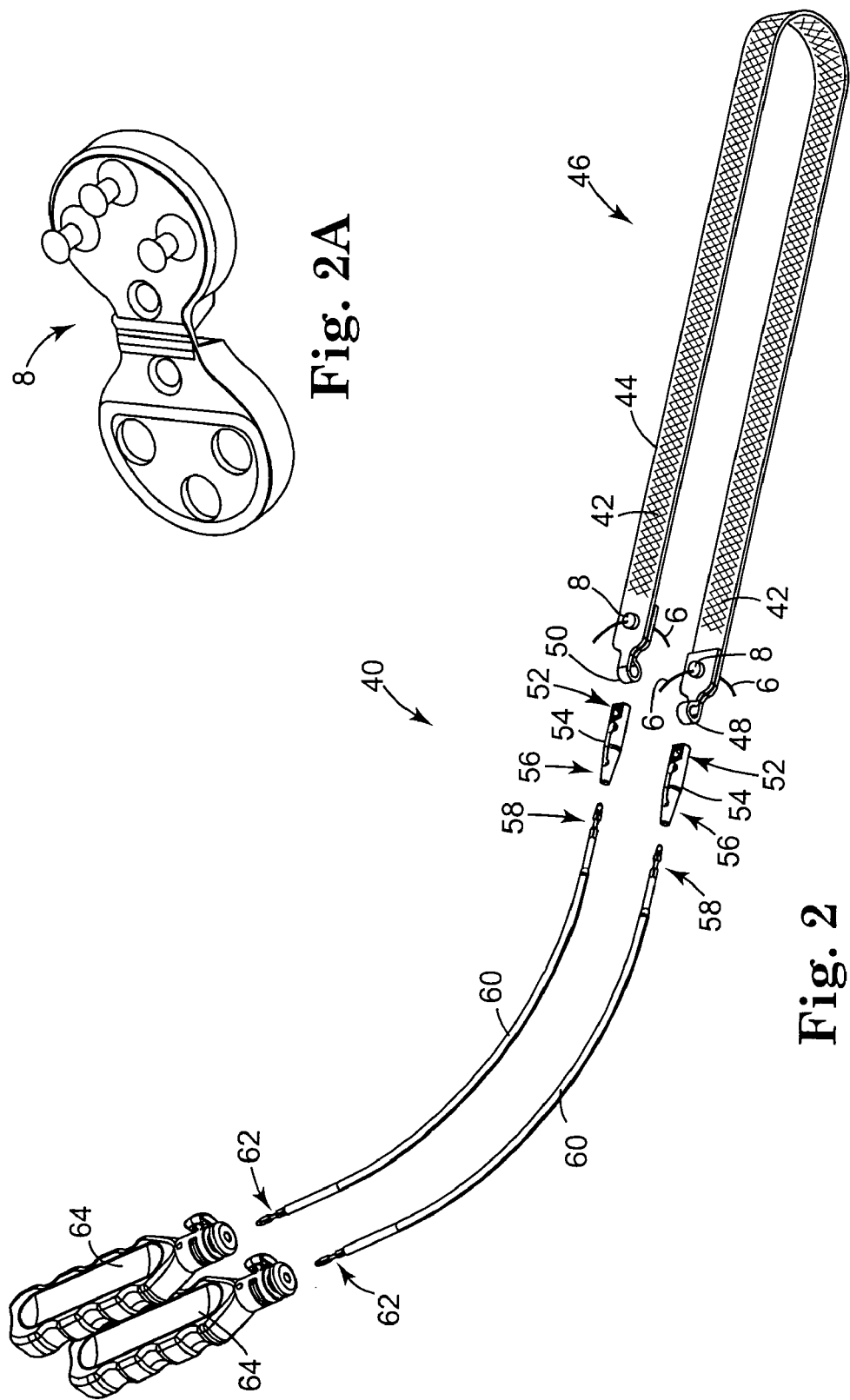
FIG. 2 is a perspective view of one embodiment of sling delivery system of the present invention, showing the sling delivery system disassembled.
FIG. 2A is an enlarged perspective view of an optional connector for use in the kit of FIG. 2.

FIG. 2 illustrates a sling assembly comprising sling 42 and sheath 44 that are made of biocompatible materials having sufficient strength and structural integrity to withstand the various forces exerted upon these components during an implant procedure and/or following implantation within a patient.

Preferably, the overall dimensions of the sling assembly 46, including insertion sheath 44 and sling 42 are sufficient to extend from an abdominal incision, to an undersurface of the urethra and back to another abdominal incision with additional size to account for the imprecision associated with the range of human anatomy sizes. In a preferred embodiment, the sheath length of the assembly of the present invention is approximately within the range of 52.0 cm to 58.5 cm (20.5 inches to 23.0 inches), sheath width is approximately within the range of 1.0 cm to 1.63 cm (0.482 inch to 0.642 inch) and sheath material thickness is approximately within the range of 0.127 mm to 0.203 mm (0.005 inch to 0.008 inch), respectively. The associated sling 42 has a length, width and thickness approximately within the range of 40 cm to 51 cm (15.7 inches to 20.1 inches), 1.0 cm to 1.2 cm (0.394 inch to 0.472 inch) and 0.508 mm to 0.711 mm (0.020 inch to 0.028 inch), respectively.

The sling 42 of the present invention can be implanted without the need for bone screws. Upon implantation, a portion of the sling 42 is passed and/or woven through various layers of abdominal/pelvic tissue.

The sling 42 is designed to remain within the body of a patient as an implant for a predetermined therapeutically effective amount of time. The sling may be non-absorbable, absorbable or resorbable, including any combinations of these material properties, depending on the desired treatment. The general characteristics of the sling material and design should be such as to withstand the various forces exerted upon it during implantation (for example, frictional forces associated with tissue resistance) and after implantation (for example, increased abdominal or bladder pressure caused by a stress event).

The precise, final location of the sling 42 will depend on a variety of factors including the particular surgical procedure(s) performed, and any preconditions of the patient such as scar tissue or previous surgeries. For example, it may be preferred to place the sling 42 in close proximity to, but not in contact with, a mid portion of the urethra to treat incontinence.

Figure 2B:
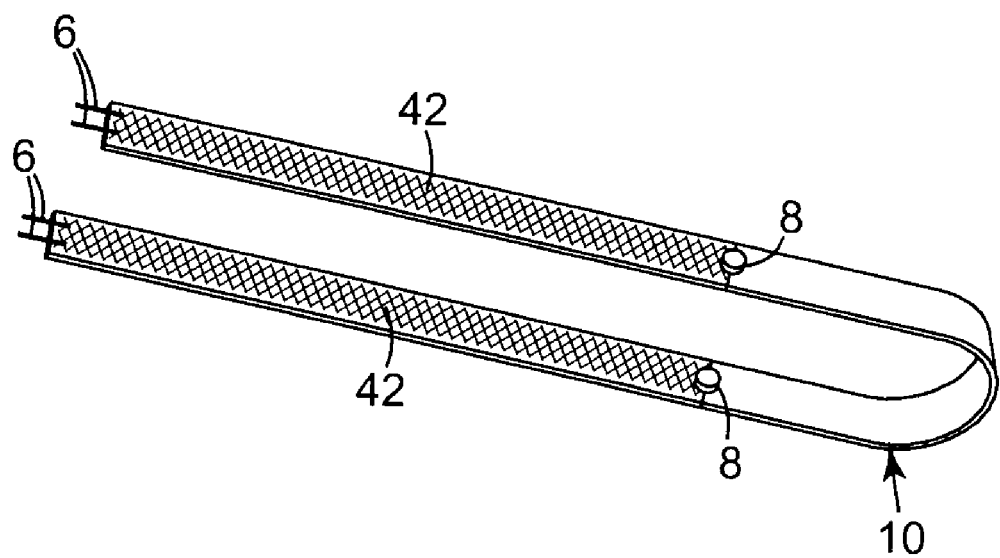
FIG. 2B is a perspective view of a sling constructed from two different sling materials according to the present invention.
Figure 2C:
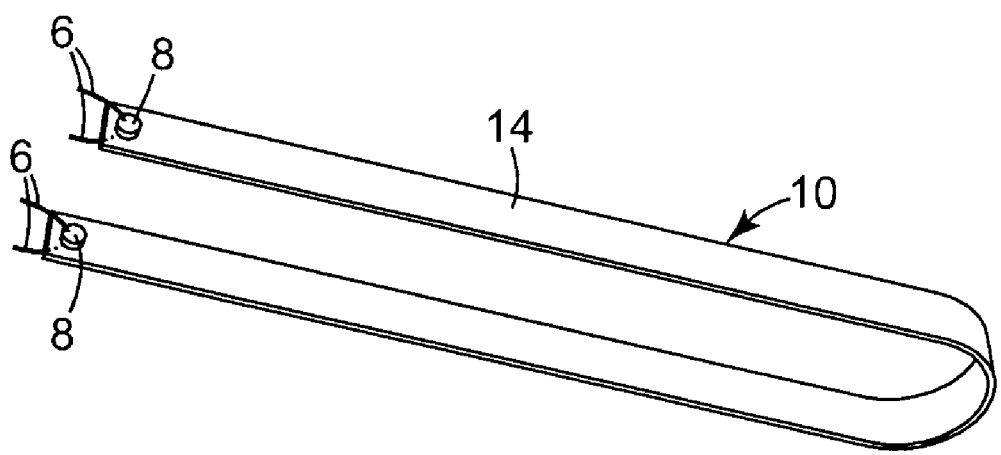
FIG. 2C is a perspective view of a sling having a suture associated therewith by means of a suture anchor.

In another aspect, the present invention includes an element that affords construction of a hybrid sling from different types of sling materials. FIG. 2 shows a sling constructed from a synthetic material 42. FIG. 2B illustrates a sling constructed from a synthetic material 42 and a non-synthetic material 10. FIG. 2C shows a sling assembly constructed from a non-synthetic material 10. The connector 8 shown in FIG. 2A may be used to connect one type of sling material 10 to another type of sling material 42 or to connect a sling with a needle. Any suitable biocompatible structure may be used as the connector 8. For example, one or more of the connectors described in U.S. patent application Ser. No. 09/749,301, filed Dec. 27, 2000, entitled "Apparatus and Methods For Enhancing the Functional Longevity and For Facilitating the Implantation of Medical Devices" (the entire contents incorporated herein by reference) may be used.

Referring to FIG. 2, the connector 8 may be used to attach a loop 48 of sheath 44 to a dilator 54 (described more fully below) or the connector 8 may be used to operatively associate a suture 6 with the sling assembly 46. The suture 6 may then be used to attach the sling assembly 46 to needle 60 or another type of needle.

In use, a particular surgeon may prefer to place non-synthetic material (e.g. 10) in the mid portion of the sling, believing that such a sling is less likely to erode the urethra of a patient. That surgeon may also desire to have synthetic materials along the end portions of the sling, believing that such synthetic end portions are more likely to anchor in tissue and promote tissue ingrowth. In another alternative, a surgeon may construct a silicone coated synthetic sling material in the mid portion of the sling to avoid tissue erosion and a polypropylene mesh material along the end portions of the sling.

The connector 8 allows the hybrid sling to be constructed just prior to the surgical procedure so that it may be customized for a particular surgical procedure. A customized sling can account for factors such as pre-existing scarring, patient anatomy size and the intended use for the sling (e.g. to raise the bladder neck or to merely support it). It can also be constructed to be complementary to concomitant procedures (e.g. for addressing a prolapse). The connector 8 can be made of Delrin, ABS, nylon, polycarbonate, acetal, polyetherimide, polysulfone or other sterilizable materials.

Other elements may be used as a means for constructing a hybrid sling from a first type of sling material and a second type of sling material. For example, a biocompatible adhesive or sealant (e.g. a tissue adhesive or sealant) may be used. The biocompatible adhesive may comprise any of the adhesives, sealants and implantable materials disclosed or referenced in U.S. Provisional Patent Application No. 60/302,929 filed Jul. 3, 2001, and No. 60/307,836 filed Jul. 25, 2001, and No. 60/325,870 filed Sep. 28, 2001 (the entire contents of which are herein incorporated by reference). Additional commercial examples of such adhesives, sealants and implantable materials include Tissuebond and Tissuepatch available from Tissuemed, RapiSeal from Fusion, CoStasis from Cohesion and FocalSeal from Focal.

According to one embodiment, the sling may include a protective sheath 44 (see FIG. 2). The sheath 44 is used during insertion of the strip 42. After the sling 42 is implanted, the sheath 44 is removed and discarded. Preferably, the protective sheath 44 is constructed of a material that affords visual examination of the implantable sling material 42 and that affords convenient passage of the assembly 46 through tissue of the patient.

In a preferred embodiment, the sheath 44 is made of polyethylene. Other materials including, without limitation, polypropylene, nylon, polyester or Teflon may also be used to construct the sheath 44. The sheath material should be flexible and provide sufficient structural integrity to withstand the various forces exerted on the sheath 44 throughout the sling delivery procedure. In general, the sheath 44 is configured to have sufficient flexibility to facilitate user manipulation and adequate structural strength to withstand the various forces applied to the sheath 44 during delivery and/or positioning of the sling assembly 46. It should also conveniently separate from the sling material 42 after the sling 42 is implanted without materially changing the position of the sling 42.

The sheath 44 may comprise two elongate, separable sections. Optionally, portions of the sheath 44 may detachably and telescopically overlap near the middle portion of the sling. In addition to resisting sling exposure and contamination, the overlapping section may also be used as a visual indicator for the practitioner or user of the device. Additionally, orientation indicia (not shown) may be placed on the overlapping portion to indicate proper orientation of the sling relative to the urethra. Alternatively, other configurations of the sheath 44 are within the scope of the present invention. In particular, the sheath may be unitary as opposed to telescoping with perforations, slits, holes, scores or tear lines designed to allow separation and removal of the sheath 44.

During sheath removal, the first section and the second section of the sheath are slid off the sling 42 by pulling each end of the sheath 44 away from the middle portion of the sling assembly 46. Removal of the sheath 44 causes separation of the overlapping sheath sections, thereby exposing the sling 42. In addition, the smooth outer surface of the sheath 44 provides a relatively frictionless surface to facilitate passage of the sheath 44 through the various tissues. The relatively frictionless motion also avoids disturbing the position of the sling 42 relative to the anatomy of the patient.

In another embodiment of the invention, the sheath 44, or a portion thereof, is associated with one or more substances including those substances identified with respect to sling 42. The substances may be used to enhance sheath removal, identify twists along the sheath 44 (and thereby indicate proper sling orientation), indicate cutting/separation points, indicate center-point, resist infection or provide other desirable effects. For example, a first surface of the sheath 44 may include indicia that should lie opposite the urethra or bladder neck to ensure proper sling orientation. Thus, the indicia provide the practitioner/surgeon with a visual indicator to aid in properly orienting the sling assembly 46, and ultimately the sling 42, within the patient.

In another aspect, the present invention comprises an article (e.g. 54, FIG. 2) for use in a surgical sling procedure. The article 54 comprises a body portion having first end portion 56 and second end portion 52 opposite the first end portion 56. The first end portion 56 has surfaces for associating the article 54 with a needle (e.g. end 58 of needle 60). The second end portion 52 has sling association means for associating the article with a sling. The sling association means may comprise a hole 90.

Preferably, the article 54 comprises a dilator that dilates a needle track for ease of sling introduction and positioning within the patient. End 58 of the needle 60 is preferably keyed to allow for convenient, secure attachment of the needle 60 relative to the dilator 54. In a preferred embodiment, the key feature prevents rotation of the dilator 54 relative to the needle 60.

The kits shown in FIGS. 1, 1A and 2 include two dilators. The dilator 54 atraumatically creates and/or expands the passageway through the tissues for sling assembly delivery. The dilator 54 is preferably short relative to a needle 60 for ease of passage of the assembly and to reduce the overall amount of tissue that is deflected at one time. Preferably, the dilator is less than 2.5 inches in length, and more preferably, it is less than one inch in length. The maximum radius of a dilator 54 is preferably less than 10 mm, more preferably less than 7.5 mm, even more preferably less than 5 mm. The tip of the dilator 54 is preferably blunt, as, in preferred embodiments, the leading tip of the dilator 54 will pass through tissue that has already been pierced by a needle 60.

The dilator 54 may be made from a variety of biocompatible and sterilizable materials including, without limitation, acetal, Delrin®, Acrylonitrile-Butadiene-Styrene (ABS), polyethylene, nylon and any combination of biocompatible materials.

The dilator 54 preferably includes means for associating with a surgical needle 60. In a preferred embodiment, the association means affords a permanent affixation between the dilator 54 and the needle 60. By "permanent affixation", it is meant that it would be very difficult to manually separate the dilator from the needle after they have become permanently affixed. After implantation of the sling 42, to separate the sling 42 from the dilator 54/needle 60, the surgeon cuts an end of the sling 42 as described more fully below. The association means preferably affords quick and convenient attachment of the dilator 54 to the needle 60 to avoid wasting time in the midst of a surgical procedure. The attachment should also be secure to avoid separation of the needle 60 and dilator 54 while the combination is passed through tissue.

As seen in FIGS. 4 and 18A, the first and second ends 58 and 62 of the needle 60 may include a keying feature affording secure association between the needle and dilator 54 and/or sheath assembly 46. In one embodiment, the keying feature comprises a recess 130 and/or square-shaped portion 126. As previously described, the recess 130 and square-shaped portion 126 are designed for complementary engagement to the appropriate end of a dilator 54. Alternatively, a suture 6 may simply be tied to the recessed portion of the end of the needle 60.

The dilator 54 also includes a universal sling association means (e.g. hole 90) for associating with the surgeon's choice of sling. Optionally, the dilator 54 may be preattached to the sling 42 and/or sheath 44, particularly if the sling is a synthetic material. Alternatively, the synthetic sling 42 can be cut and removed from dilator 54, and the dilator may be attached to a non-synthetic sling material (e.g. cadaveric or autologous sling material) just prior to sling placement.

Referring to the embodiment of dilator shown in FIGS. 23-26, the dilator 54 may be approximately 3.1 cm (1.2 inches) in length. The dilator 54 preferably includes a gentle taper 88 near its first end 56. The dilator is sized and shaped to provide atraumatic passage through body tissue. The taper 88 and relatively smooth outer surface of the dilator 54 facilitate atraumatic passage of the dilator 54 and attached sling assembly 46 through the various tissues of the patient. The presence of the dilator 54 allows a gentle transition between the diameter of the needle, to the shape of the dilator, and finally to the sling assembly 46, as opposed to prior art assemblies, where the structure of the sling assembly abruptly increases the profile of the needle and thereby the size of the structure that must pass through tissue.

Preferably, the second end 52 of the dilator 54 associates the dilator with one end of a sling 42, or sheath 44 or sling assembly 46. The sheath 44 or sling 42 is preferably attached to the dilator 54 via a first opening or through-hole 90 located near the second end of the dilator 54. In this embodiment, the opening 90 operates as a universal sling material or assembly attachment point which can receive a variety of materials, such as fascia, autologous materials, synthetics, biologic tissues and any other similar tissues, including any combinations.

Figure 21:
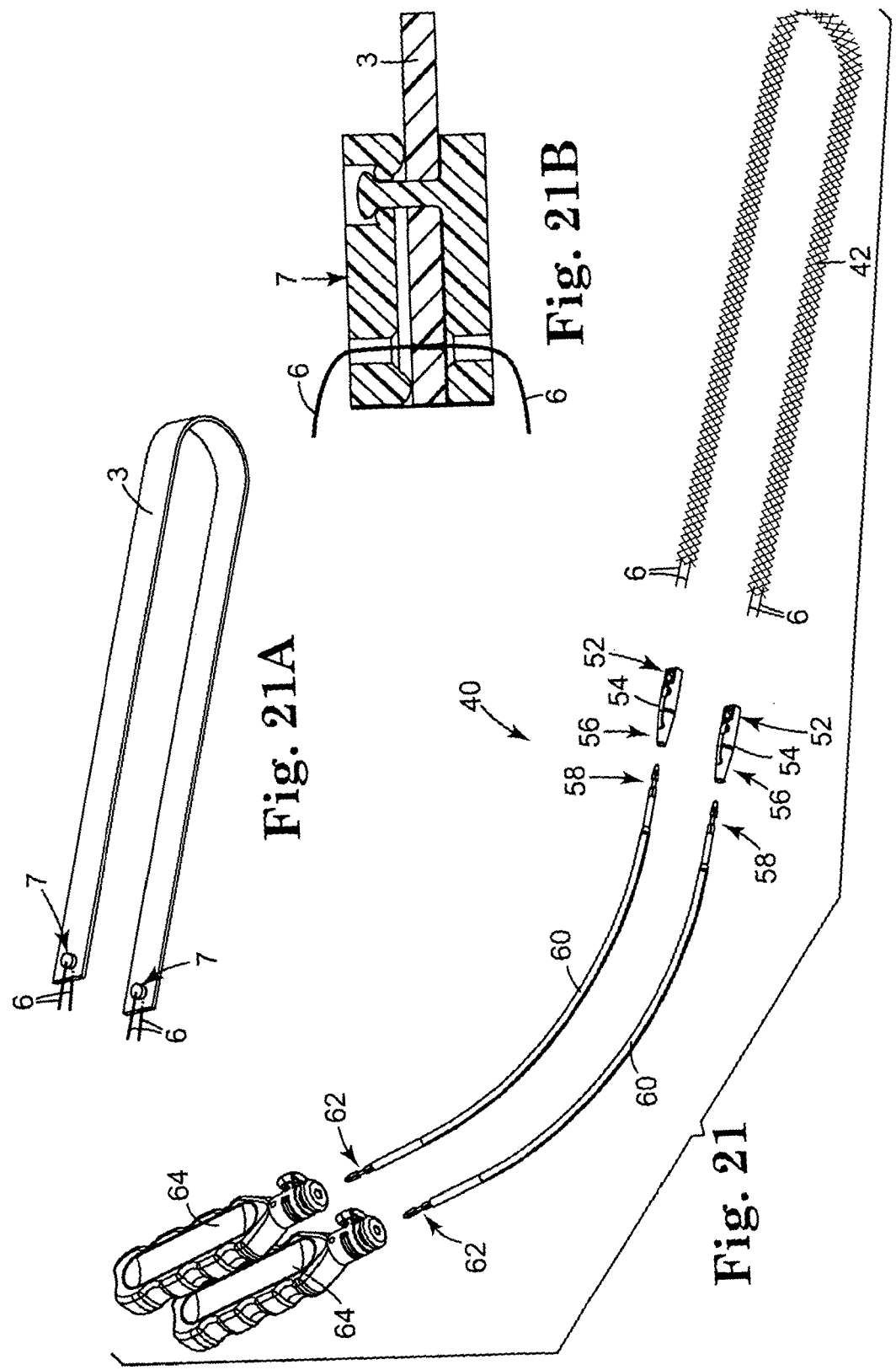
FIG. 21 is a perspective view of another embodiment of sling delivery system of the present invention, showing the sling delivery system disassembled.

FIG. 21 illustrates a first sling 42 constructed of synthetic material with a plurality of through holes and a suture 6 threaded through a hole in synthetic material 42 that is spaced from the end of the synthetic material 42. FIG. 21A shows a non-synthetic sling material 3 with a suture anchor 7 attached thereto. The suture anchor 7 firmly associates the sling 3 with the suture 6 and resists separation of the sling 3 and the suture 6. Either sling material 3 or 42 can be conveniently associated with dilator 54 by threading suture 6 through hole 90 and tying the suture. In this fashion the dilator/adapter 54 can universally connect to either a synthetic (e.g. polypropylene) mesh 42 or a non-synthetic sling (e.g. cadaveric fascia 10).

Figure 23:
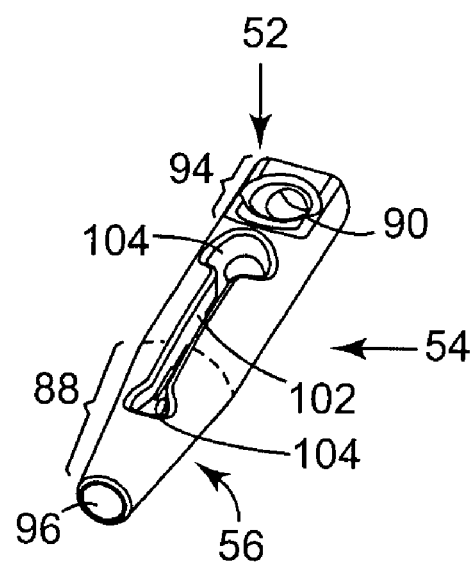
FIG. 23 is a perspective view of one embodiment of an adapter for associating a needle with a sling according to an aspect of the present invention.

In the embodiment shown in FIG. 2, the end portion 48 or 50 of one end of the sheath 44 is threaded through the opening 90 of the dilator 54 and secured to the sheath 44, thereby forming a loop. Optionally, a connector 8 may be used to secure the loop. The edge portion 48 or 50 alternatively may be fastened onto the sheath 44 via ultrasonic welding, bonding, melting, suturing, sealing or other attachment techniques. Further, as shown in FIG. 23, the end 52 of the dilator 54 preferably includes a cut-away section 94 to provide room to receive sling assembly material to reduce the overall profile of the sling assembly experienced by tissue during sling passage. Therefore, when the sheath is attached to the cut-away section, the additional sheath material is not apt to significantly increase the relative thickness, diameter or profile of the dilator 54.

Figure 24:
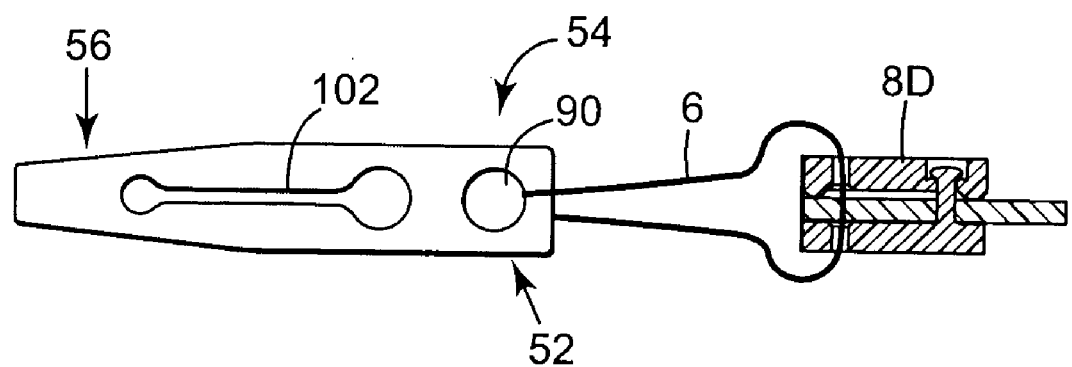
FIG. 24 is a top view of the adapter of FIG. 23 shown sutured to a sling assembly.
Figure 25:
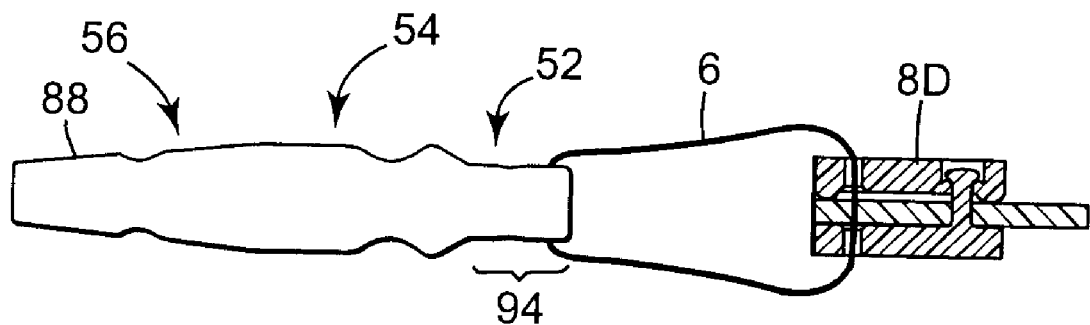
FIG. 25 is a side view of the adapter of FIG. 23 and a suture threaded through a passageway in the adapter and through a sling anchor on a non-synthetic sling.
Figure 26:
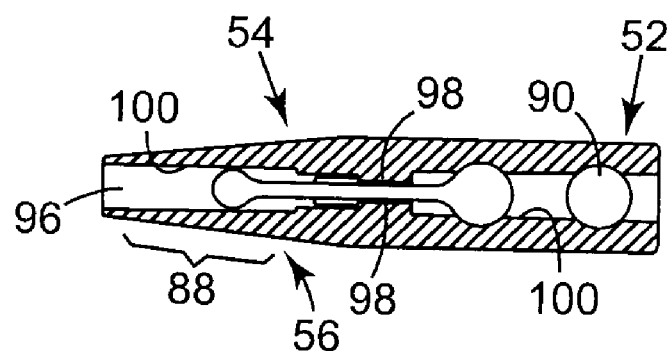
FIG. 26 is a sectional view of the adapter of FIG. 23.

As shown in FIGS. 24 and 25, one or more sutures 6 may be threaded through hole 90 and used to connect a sling to the dilator. This gives the surgeon the option to associate the dilator with a particular sling material just prior to implantation. Optionally, a suture anchor article 8D (FIG. 24) may be used to enhance the attachment of the suture 6 to the sling material, particularly if the sling material is sensitive to suture pull through (e.g. such as some cadaveric fascia).

Alternatively, for dilators 54 manufactured via molding techniques, the end of the sheath 44 may be encased within and secured to the second end 52 of the dilator 54 during the molding process. In yet another embodiment, the end of the sheath 44 may be fixedly attached within a longitudinal slot located near the first end 52 of the dilator 44 using an adhesive, ultrasonic welding or other attachment techniques.

Referring to FIGS. 23-26, the first end 56 of the dilator 54 includes a second opening or through-hole or lumen 96 that extends substantially internally along the longitudinal axis of the dilator 54. The hole 96 preferably extends the length of the dilator 54.

The lumen 96 has an internal diameter generally configured for convenient attachment to a needle 60 or similar sling-delivery device. In one embodiment, the internal diameter of the second opening 96 of the dilator 54 is approximately within the range of 0.239 cm to 0.318 cm (0.094 inch to 0.125 inch). A shoulder 98 located on the surface 100 of the second opening 96 of the dilator 54 and a complementary mating recess located on the surface of the first end of the needle 60 securely and permanently attach or lock the dilator 54 and needle 60 together. Once the needle 60 is inserted into the dilator 54, they are preferably not separated thereafter. After the sling 42 is implanted, the connected needle 60 and dilator 54 are removed from the sling by cutting an end of the sling as described in greater detail below. Preferable, the needle 60 and dilator 54 are discarded after the surgical procedure.

One or more longitudinal slots 102 located on the outer surface of the dilator 54 and in communication with the second opening 96 allow the wall of the dilator 54 to expand in a radially outward direction when the first end of the needle 60 is inserted into the second opening 96 of the dilator 54. When the shoulder 98 of the dilator 54 passes the recess of the needle 60, the wall of the dilator 54 collapses around the needle 60 as the shoulder 98 seats into the recess, thereby securing the dilator 54 on the needle 60 and blocking separation of the dilator 54 and needle 60.

Although the invention has been described in terms of a shoulder 98 and mating recess, alternative dilator-needle attachment mechanisms such as bumps, grooves, slots, wedges, detents and other mechanisms are also included within the scope of the claimed invention. The dilator 54 preferably includes one or more relief ports 104 to facilitate convenient needle connection. The relief ports 104 may be formed at the ends of the longitudinal slots 102 or at various high-resistance locations along the dilator 54. The relief ports 104 decrease the rigidity or resistance of radially outward expansion of the dilator wall and, reduce the amount of force required to insert or securely attach the needle 60 to the dilator 54. In yet another embodiment, superficial bands or rings, arc-shaped slots, superficial grooves or other mechanisms may provide improved expansion or attachment characteristics.

A portion of the dilator 54 includes a taper 88 having a decreasing profile toward the second end 56 of the dilator 54. The taper 88 preferably gently cams tissue out of the path of the sling assembly 46 as the sling assembly is inserted in the body. The taper 88 is also sized and shaped to reduce the amount of friction or resistance as the device is drawn through the tissues of the patient. The amount of force required to manipulate the device through the tissues is thereby reduced. This in turn provides the user of the assembly with additional control over device insertion and maneuverability through tissue and within the patient. In addition to tapered profiles, other dilator profiles such as conical, flared, frusto-conical, pyramid-shaped, elliptical or other applicable profiles may also be used. Overall, the profile of the dilator 54 is preferably configured to provide easy dilation of the tissue to accommodate smooth passage of the sling 42/sling assembly 46 and subsequent collapse of the surrounding tissue to securely anchor the sling 42 into the tissue (after sheath removal).

Figure 18:
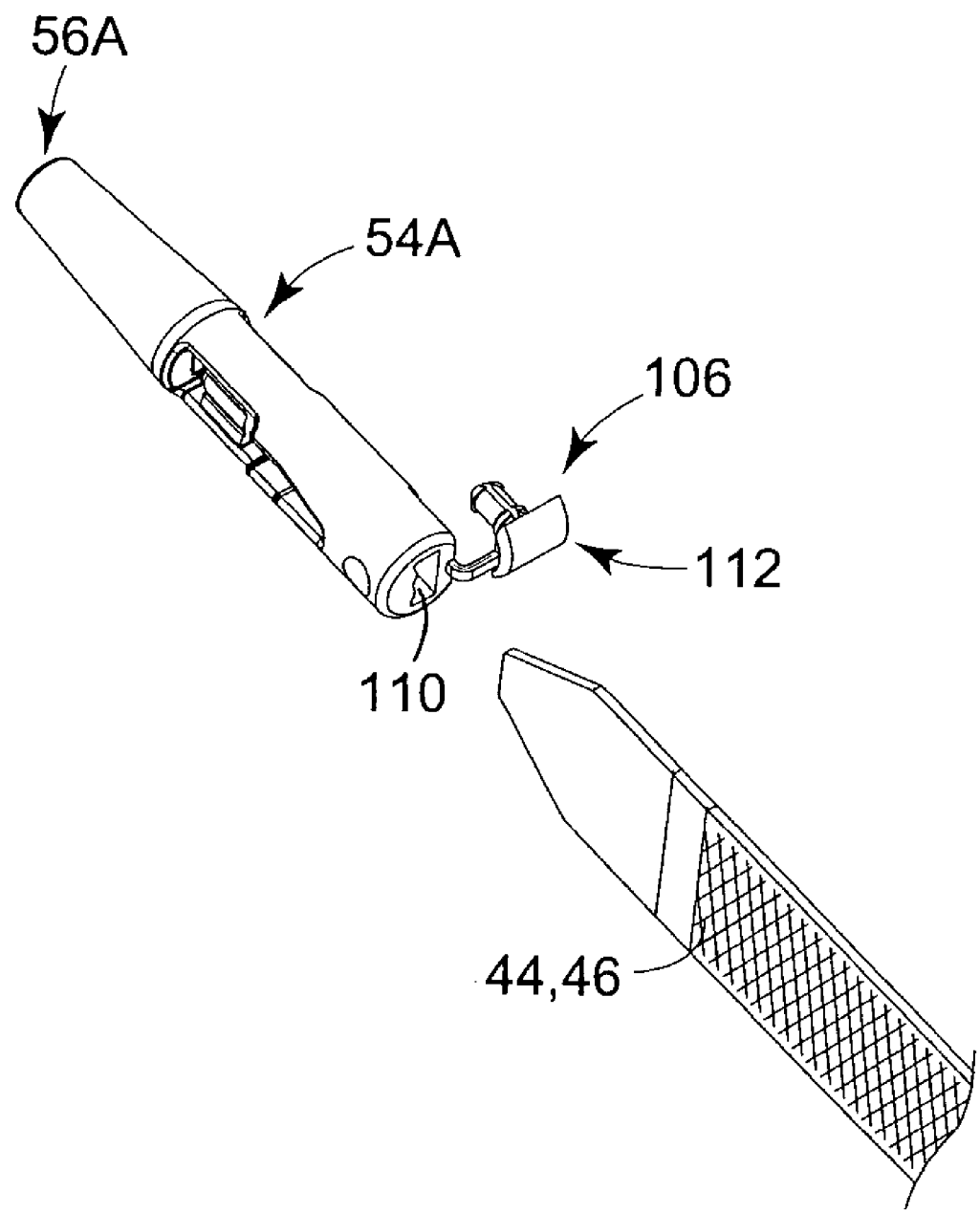
FIG. 18 is a perspective view of an embodiment of an adapter for associating a needle with a sling according to an aspect of the present invention, and portions of a sling assembly or sling.

In other embodiments of the invention, shown in FIGS. 18 and 18A, a dilator 54A or 54B includes a sling fastening snap mechanism 106 or 106' on one end of the dilator. The embodiment disclosed in FIG. 18A includes a keyed/locking mechanism on its other end. Referring to FIG. 18, the end of the dilator 54a includes a slot or slot-shaped opening 110 configured for convenient insertion of one end of a sling 42 (such as one made from non-synthetic tissue) or sling assembly 46 (e.g. of synthetic materials) either at the surgical site (e.g. by the operating room nurse or surgeon) or other location (such as manufacturing location). Additional shapes for the dilator opening 110 include, without limitation, oval, circular, square, rectangular and other shapes. The slot-shaped opening 110 is located along a portion of the longitudinal axis of the dilator 54A.

Referring to FIG. 18A, snap-like element 112' is located on an outer surface near the first end of the dilator 54B. The snap-like element 112' includes a barb or spike 114 that fits within an opening 116 situated near the first end of the dilator 54B. The opening 116 for the barb 114, preferably configured perpendicular to the slot-shaped opening 110', is sized and shaped to match or mate with the barb 114 of the snap-like element 112'. When the barb 114 is fully seated within the opening 116 of the dilator 54B, the tip 118 of the barb 114 extends into the slot-shaped opening 110' of the dilator 54B. A first ridge 120 and a second ridge 122 located along the length of the barb 114 further secure and/or fasten the barb 114 within the opening 116 of the dilator 54B. Other fastening configurations including, but not limited to, bumps, shoulders, tabs, detents, tongue in grooves, snaps and any combinations of fastening means may also be used with the present invention.

During use, one end of the sling (e.g. 10 or 42, in FIG. 1), sheath 44 or sling assembly 46 is inserted into the slot 110' of the dilator 54B. With the end of the sling 42/sling assembly 46 properly positioned within the slot 110', the barb 114 of the snap-like element 112' is inserted into the opening 116 of the dilator 54B. The barb 114 is fully seated within the opening 116 when both ridges 120, 122 pass through the opening 116 of the dilator 54B. This causes the tip 118 of the barb 114 to bear down on or penetrate a portion of the sling 42/sling assembly 46 extending within the slot 110' of the dilator 54B, thereby securely fastening the sling 42/sling assembly 46 to the dilator 54B.

A keyed/locking mechanism 108 is located near the second end 56B of the dilator 54B. As shown in FIG. 18A, a square-shaped opening 124 extends along a portion of the longitudinal axis near the second end 56B of the dilator 54B. The shape of the dilator opening 124 matches the square-shaped perimeter of the keying-segment 126 located near the first end 58 of the needle 60 and allows keyed-rotation of the dilator 54B at ninety-degree intervals. Other appropriate shapes for the dilator opening 124 may also be used provided that the shape of the opening 124 complements the corresponding keying-segment shape located near the first end 58 of the needle 60. When the first end 58 of the needle 60 is positioned within the dilator 54B, the square-shaped opening 124 of the dilator 54B together with the keying-segment 126 of the needle 60 prevents axial rotation of the dilator 54B relative to the needle 60 and, thus, twisting of the sling 42/sling assembly 46. This optional feature provides the practitioner or user of the assembly with control and maneuverability of the assembly before and during the insertion procedure.

The dilator 54B also includes a locking mechanism 128. Referring to FIG. 18A, the locking mechanism 128 comprises one or more tension-loaded ribs located within the longitudinal opening of the dilator 54B. The configuration of the ribs generally matches and corresponds to a complementary recess 130 located near the first end 58 of the needle 60. Thus, the first end 58 of the needle 60 is inserted through the longitudinal opening 124 of the dilator 54B until the ribs of the dilator 54B seat within the recess 130 of the needle 60. The dilator 54B is securely attached or locked onto the needle 60 when the dilator ribs are fully seated within the needle recess 130.

Figure 18B:
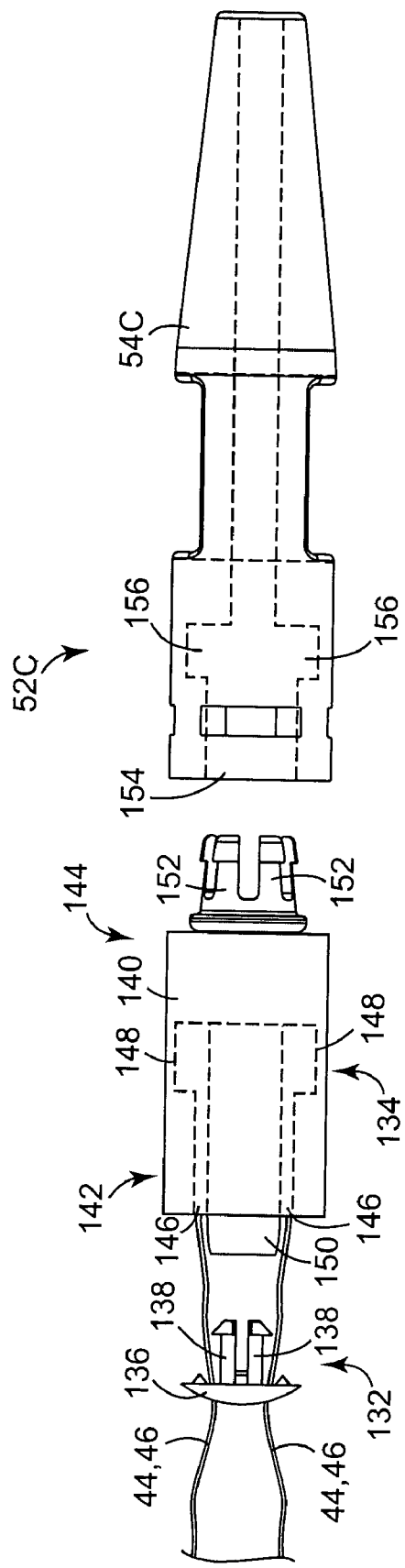
FIG. 18B is a side view of another embodiment of an adapter for associating a needle with a sling according to an aspect of the present invention, and portions of a sling or sling assembly.

Referring to FIG. 18B, in an alternate embodiment of the invention, the sheath 44 (or sling 42 or 10 or assembly 46) is attached to the dilator 54C via a locking (or compression) collet 132 and adapter connector 134. The compression collet 132 comprises a ring-shaped portion 136 having one or more barbed snap tongs 138. The complementary adapter 134 comprises a cylindrical element 140 having a first end 142 and a second end 144. The internal profile near the first end 144 of the adapter connector 134 includes a tubular lumen or channel 146, having one or more recesses, shoulders, grooves or similar indentations 148, surrounding an internal prong 150. The second end 144 of the adapter connector 134 includes one or more barbed snap tongs 152, similar to the tongs 138 of the compression collet 132. In addition, the first end 52C of the dilator 54C includes a longitudinal opening 154 having one or more recesses, grooves, slots or related types of indentations 156 configured to engage the tongs 152 of the adapter connector 134.

In use, one end of the sling (e.g. 10 or 42/sling assembly 46) of the present invention is configured into a tubular or appropriate shape that enables a sufficient portion of the end of the sling 42/sling assembly 46 to be inserted through the compression collet 132. The tongs 138 of the compression collet 132 are then inserted into the first end 142 of the adapter connector 134, causing the tongs 138 to snap into engagement with the adapter connector 134. The end portion of the sling 42/sling assembly 46 is compressed between the tongs 138 of the compression collet 132 and the internal prong 150 of the adapter connector 134, thereby securely fixing the sling 42/sling assembly 46 to the collet/adapter assembly. In a similar fashion, the tongs 152 of the adapter 134 are then inserted and snap-locked into the first end 52C of the dilator 54C, creating a secure fixation between the collet/adapter assembly and dilator 54C. Alternatively, a non-synthetic sling 10 could replace sling 42 in this embodiment of the present invention.

Figure 22:
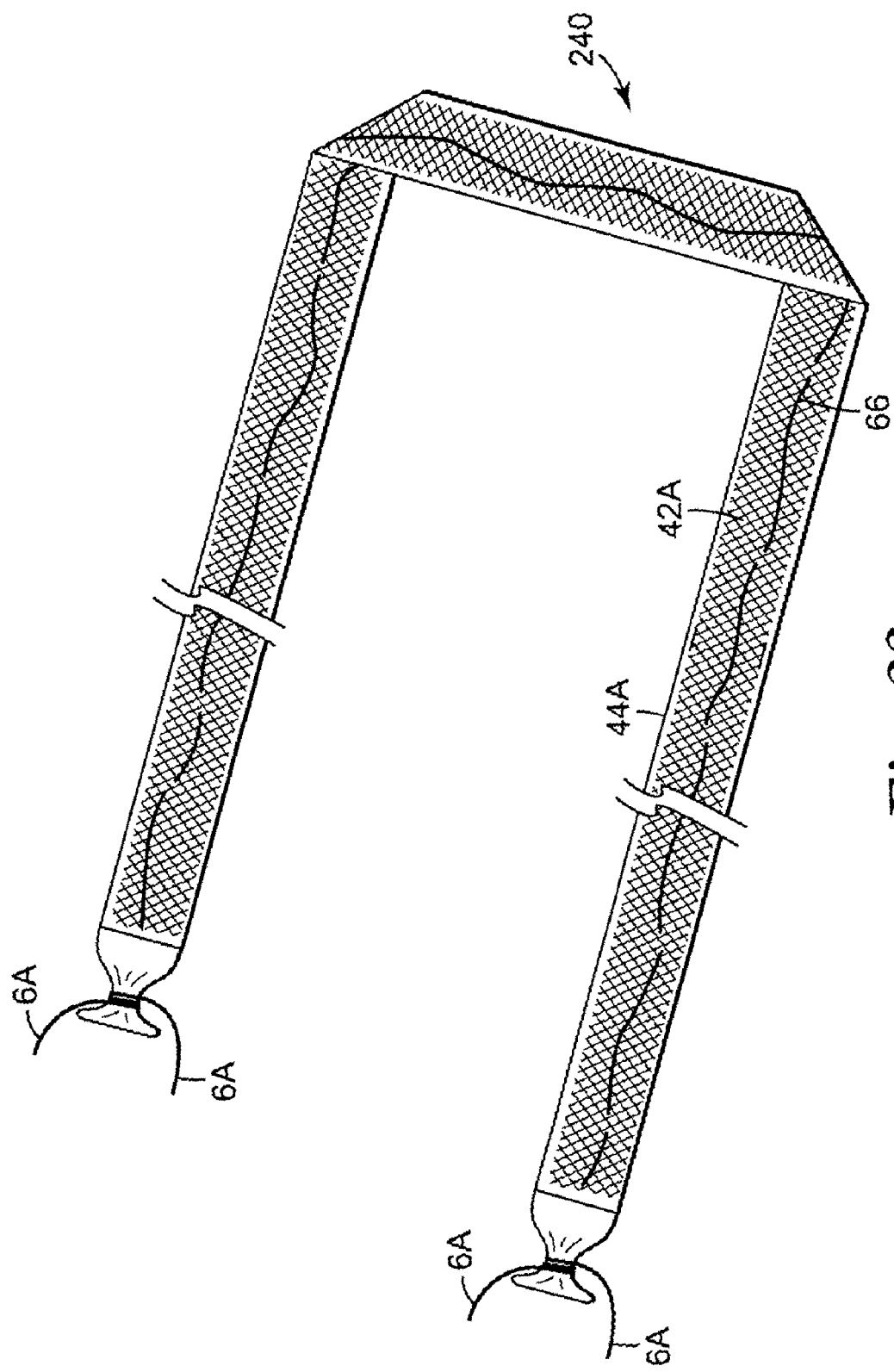
FIG. 22 is a top view of a sling assembly according to an aspect of the present invention.
Figure 22A:
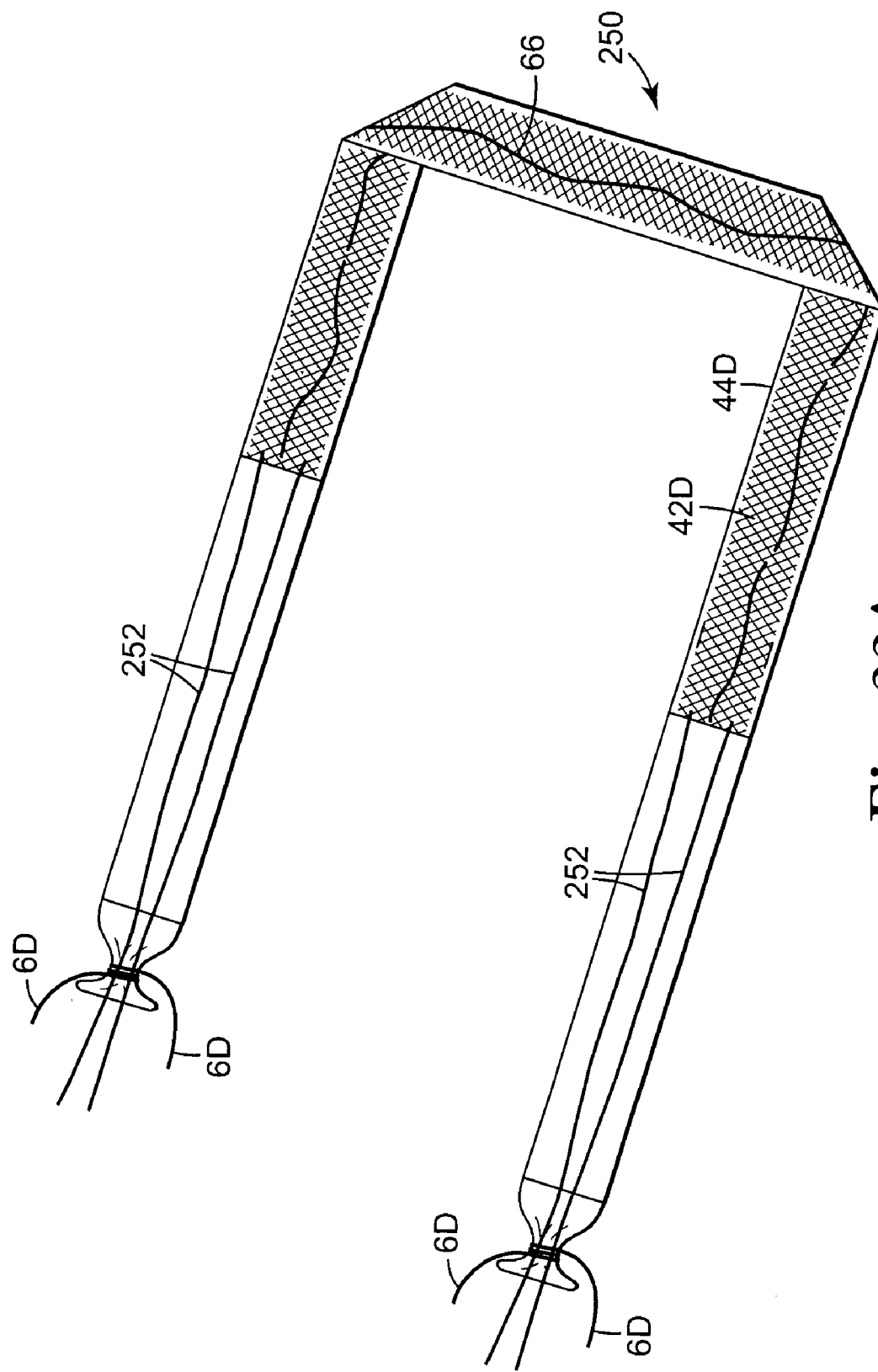
FIG. 22A is a top view of a sling assembly according to another aspect of the present invention.

In another aspect of the present invention, a dilator or adapter need not be present. Referring to FIGS. 22 and 22A, there are shown sling assemblies that may optionally be free of adapters or dilators according to additional embodiments of the present invention.

FIG. 22 illustrates a sling assembly 240 for implantation without the need to use bone anchors or screws. The sling assembly 240 comprises a synthetic surgical mesh 42A (e.g. a polypropylene surgical mesh) having a plurality of holes. The holes are preferably sized and shaped to afford tissue ingrowth. The synthetic surgical mesh is sized and shaped to be implanted during a surgical sling procedure.

Some synthetic mesh used for slings are relatively extensible. Unlike cadaveric fascia and other non-synthetic materials which tend to be relatively slippery, an extensible sling mesh may be difficult to thread through tissue alone. Also, even if such slings could be inserted alone, some synthetic slings could be damaged during insertion, or could damage tissue. A removable synthetic insertion sheath 44A (e.g. polyethylene) is situated about the surgical mesh to assist in inserting the sling mesh 42A.

The insertion sheath has first and second ends. In the embodiment shown in FIG. 22, at least one suture 6A is associated with the insertion sheath 44A and extends beyond the first end of the insertion sheath 44A a length sufficient to afford attachment of the sling assembly to a needle. At least one other suture 6A is associated with the insertion sheath 44 and extends beyond the second end of the insertion sheath 44A a length sufficient to afford association of the sling assembly with a needle. Sutures 6A may be associated with sheath 44A via knotting, suture anchor, tying, weaving, bonding, ultrasonic welding or other attachment techniques, including combinations thereof, to prevent suture 6A detachment during and/or following sling implantation. The sling 42A may optionally be associated with the sheath 44A through such techniques.

The suture 6A can be attached to the needle by a multitude of approaches, such as being tied, knotted, or placed in a suture passageway and retracted into the needle as described above. For example, the straight needle shown in FIGS. 9, 9A and 10 could be, used to implant the sling assembly 240. In use, the needle 80 is inserted suprapubically and emerges from the body through a vaginal incision. The button 88 can then be extended to expose the suture accept hole 82 and the suture 6A can be passed through hole 82 and tied. The tied suture could then be retracted within the sheath 87 by manipulating button 88. The needle 80 could then be pulled up through the body to implant the sling 240. Alternatively, a stock ligature carrier could be used instead of needle 80.

Figure 34:
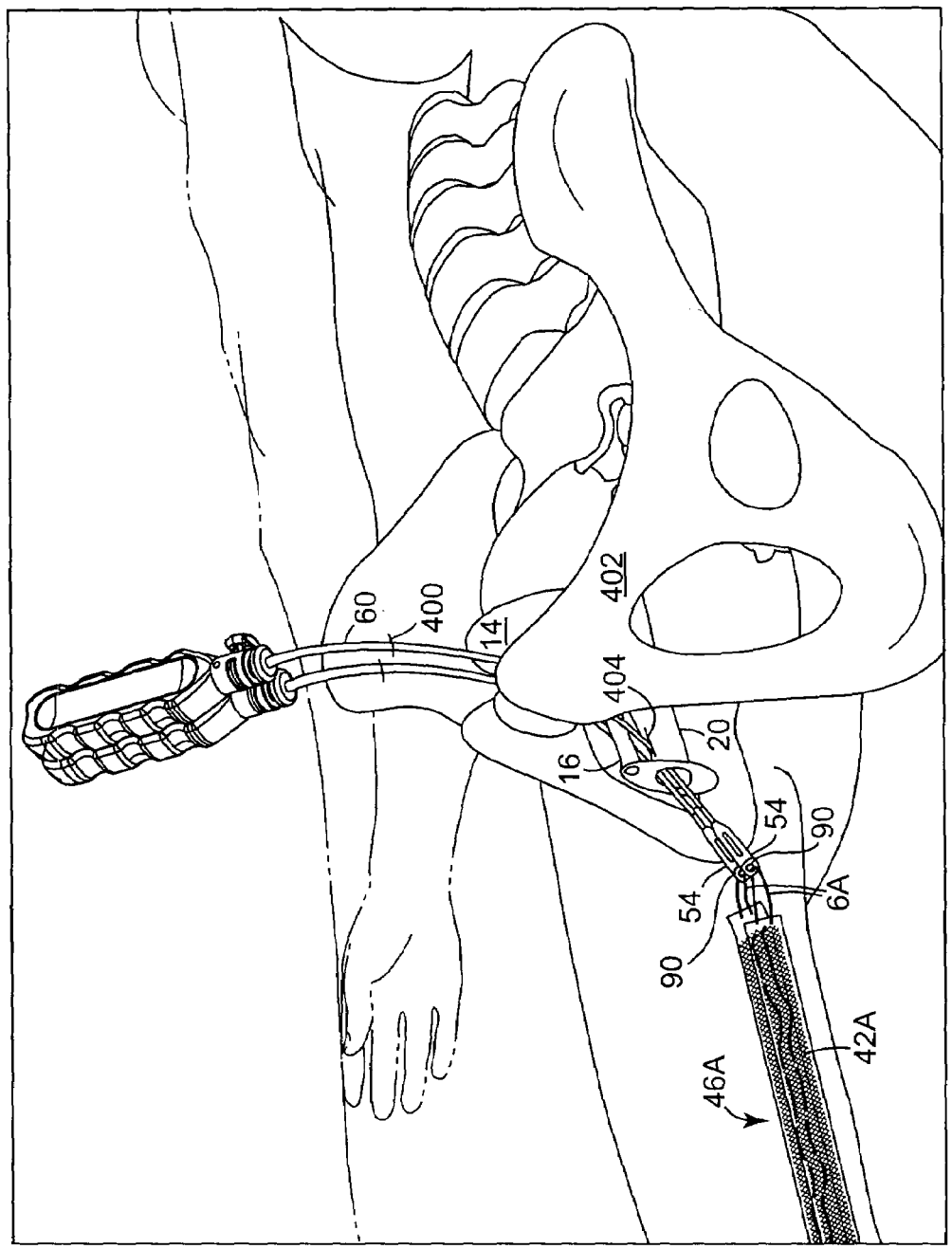
FIG. 34 is a perspective view of a sling system attached to two needles according to an embodiment of the present invention.

Optionally, the suture 6A could be tied to a dilator or other component of a needle assembly as shown in FIG. 34. Preferably, the insertion sheath 44A defines an interior portion that includes the surgical mesh, and an exterior portion, and the sutures 6A that extend beyond the first and second ends of the insertion sheath 44A are completely situated on the exterior portion of the sheath. Also preferably, the insertion sheath 44A is securely attached to the sling 42A, by a means such as ultrasonic welding, suturing or adhesive. A tensioning member 66 may optionally be provided.

FIG. 22A illustrates another embodiment of a sling assembly 250 for use in an incontinence procedure. The sling assembly 250 is particularly suitable for implantation without bone anchors and need not include a dilator or adapter. The sling assembly comprises a synthetic surgical mesh 42D having first and second ends and a plurality of holes that are sized and shaped to afford tissue ingrowth. The synthetic surgical mesh 42D is preferably sized and shaped to be implanted during a surgical sling procedure designed to treat incontinence in females. It may be sized and shaped to be placed mid-urethra in a tension free fashion to treat SUI. It may be long enough to extend from the patient's abdominal fascia to the patient's urethra and back again or it may be shorter and utilize sutures 252 for anchoring in the abdominal fascia.

The sling assembly 250 includes a removable synthetic insertion sheath 44D situated about the surgical mesh 42D. At least one suture 252 is associated with the surgical mesh 42D and extends beyond the first end of the surgical mesh 42D. Preferably the suture 252 has a length sufficient to afford attachment of the sling mesh 42D to a needle. Another suture 252 is operatively associated with the surgical mesh and extends beyond the second end of the surgical mesh a length sufficient to afford attachment of the mesh to a needle. Sutures 252 may be operatively associated with the mesh 42D in a variety of fashions (e.g. by tying, knotting, weaving, adhering, or welding). Alternatively, a suture anchor or pledget may be used to anchor the sutures 252 to the mesh 42D.

Preferably, the insertion sheath 44D defines an interior portion that includes the surgical mesh 42D, and an exterior portion. Suture 252 preferably extends beyond the first end of the surgical mesh and extends from the interior portion of the sheath 44D to an exterior portion of the sheath 44D.

Optionally, sutures 6D may be tied to the end of the sheath 44D. Preferably, sutures 6D are provided in a different color than sutures 252. Alternatively, sutures 6D can be omitted and sutures 252 can be tied to external portions of the sheath 44D.

The sutures 252 may optionally be anchored to tissue in the body (e.g. the abdominal rectus fascia) to help secure the sling. In this embodiment, it is preferred that the sutures 252 are of a different color than sutures 6D.

Figure 19:
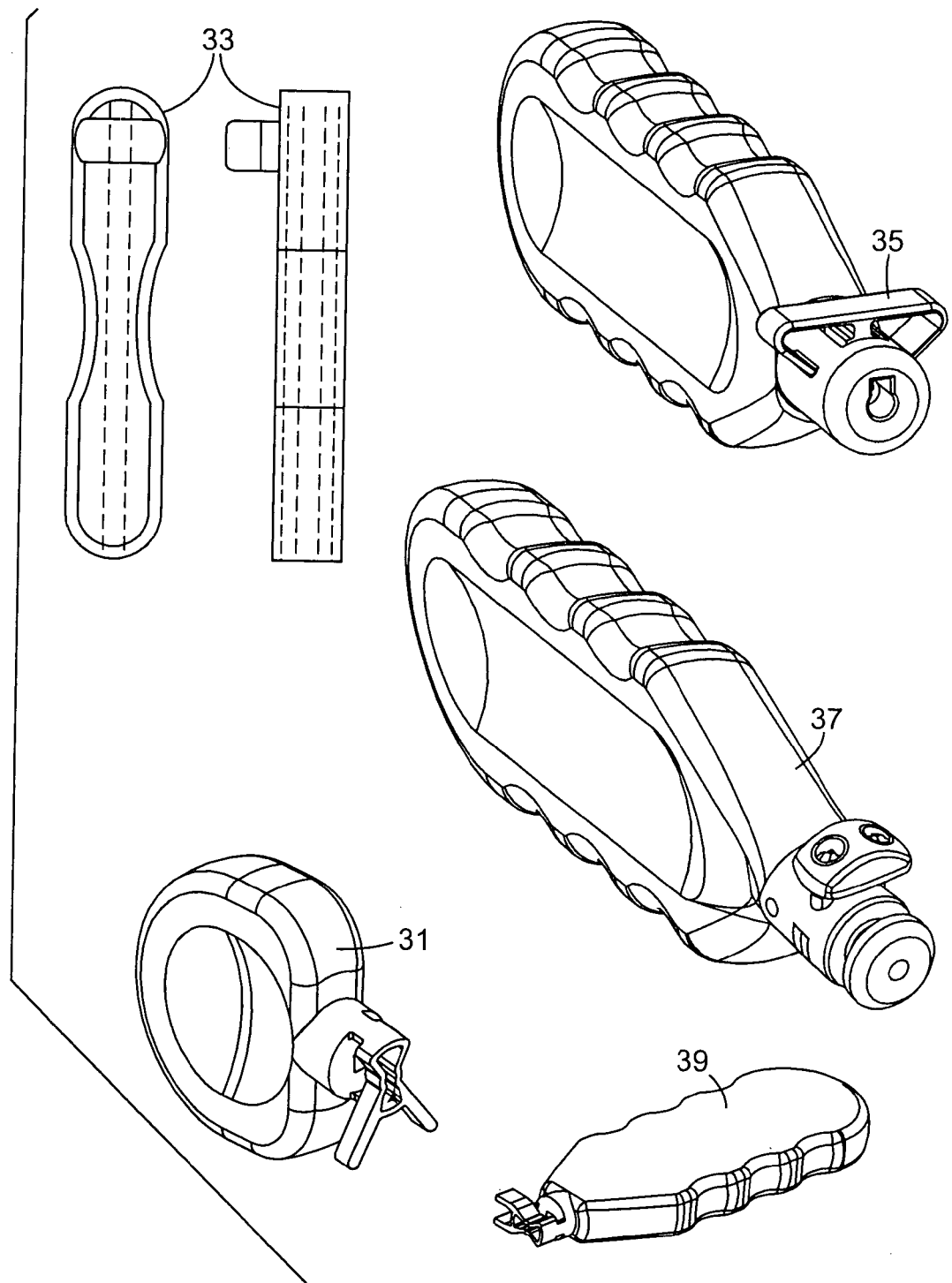
FIG. 19 includes perspective views of various optional handles for optional use according to the present invention.

Referring now to FIGS. 1 and 19, there is shown another aspect of the present invention. In this embodiment, the present invention comprises a surgical kit for treating incontinence. The kit comprises an implantable material (e.g. 10), and a needle 60. The needle 60 has surfaces for engaging a handle. The kit also includes at least one of a first type of handle 64 having surfaces for attaching the handle to the needle 60, and at least one of a second type of handle (e.g. see FIG. 19) having surfaces for attaching the handle to the needle 60.

As used in this application, when it is said that one handle is a different type than another handle, it is meant that the handles substantially differ in a feature that can potentially affect a surgical procedure for treating a urological disorder. Features that can be different according to the present invention include the size of the handles, the shape of the handles, the materials used to construct the handles, the presence, absence or location of finger indents, whether the handle is movable, whether the handles are repositionable, whether the handles are releasable, whether the handle can be indexed between a plurality of positions, and the location of operable elements. The handles may have any of the structure and features described in U.S. patent application Ser. No. 09/917,443 filed Jul. 27, 2001 (the entire contents of which are herein incorporated by reference).

FIG. 19 illustrates a plurality of different types of handles. Handle 22 comprises a slim, elongate structure with a button near the proximal end. Handles 31, 35, 37 and 39 have an operable member (e.g. button) near the distal end of the handle. Handle 31 is rounded, while handles 33, 35, 37 and 39 are elongate. The handles may be movable relative to a needle (e.g. slidable or rotatable), repositionable on a needle (e.g. it may be indexed between different positions) and/or replaceable on a needle (e.g. moved from one end to the other end of the needle).

Figure 5:
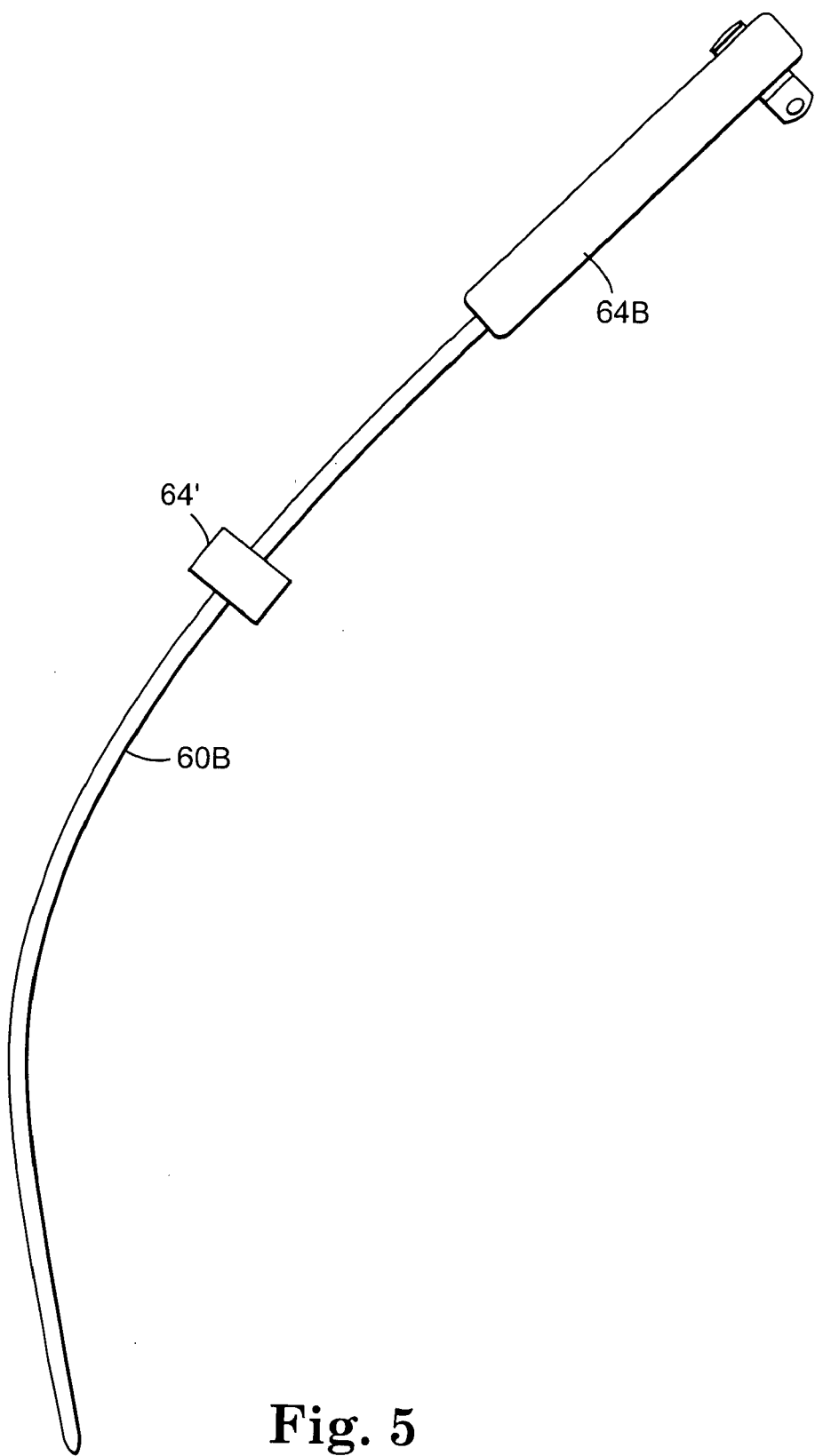
FIG. 5 is a side view of a needle with first and second handles for optional use in a kit according to the present invention.

FIGS. 15-16 show needles 202 and 204 with integral handles. FIG. 5 illustrates a first handle 64B and a second handle 64' that may be placed on the same needle 60B.

Figure 20:
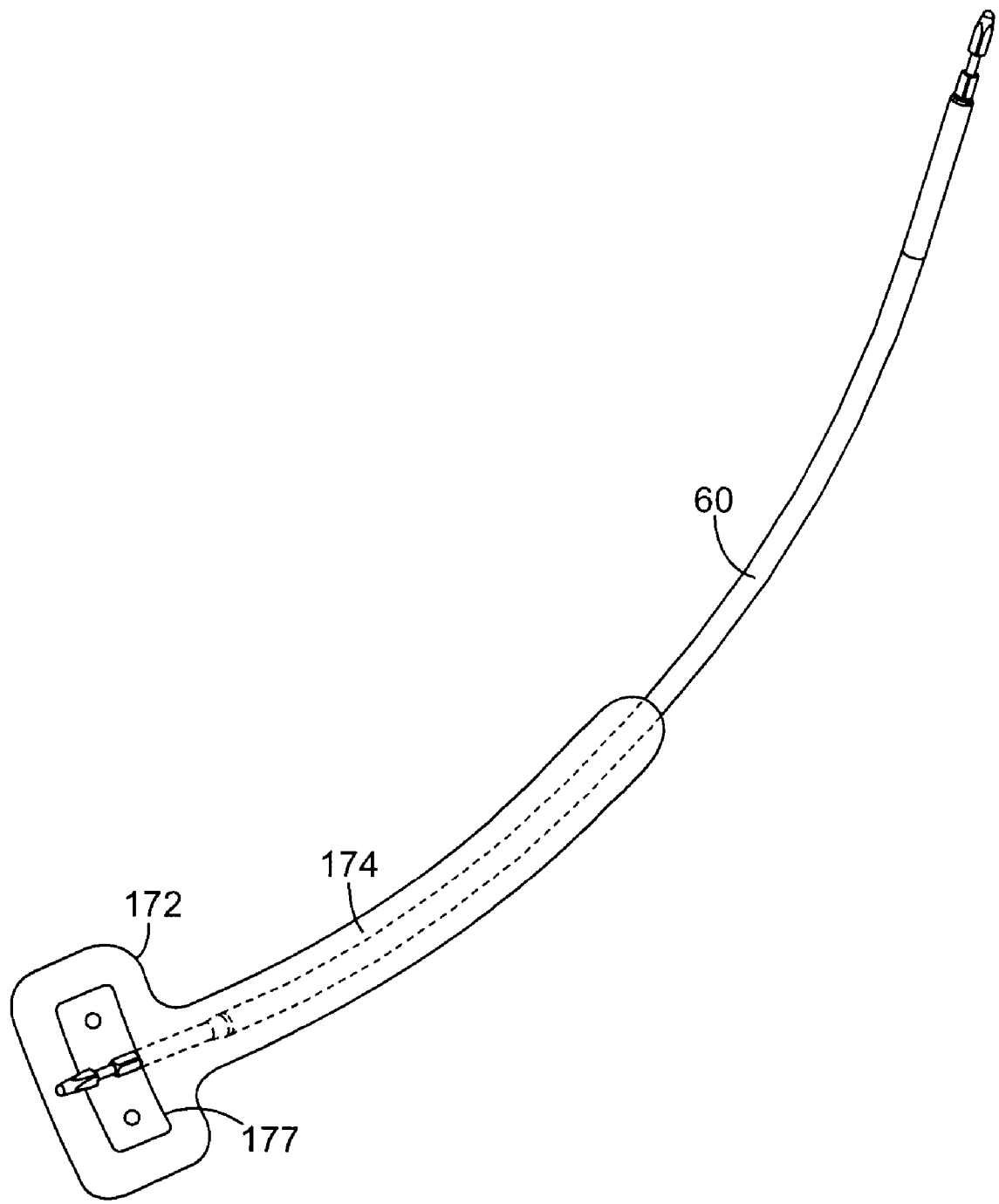
FIG. 20 is a side view of a needle with an optional strengthening handle for use in an aspect of the present invention.

FIG. 20 illustrates a handle 172 that may be attached to a needle 60. The handle 172 includes a strengthening portion 174 designed to strengthen the needle 174. The handle 172 optionally includes releasable attachment means 177 for releasably attaching the handle 172 to the needle 60. The handle 172 is particularly useful when the needle 60 includes a relatively small cross sectional area or is relatively susceptible to bending during an anticipated procedure. A kit with the handle 172 enables the surgeon to place the handle 172 on the needle 60 to avoid bending, twisting or other deformation of the needle 60 during the surgical procedure.

Figure 41:
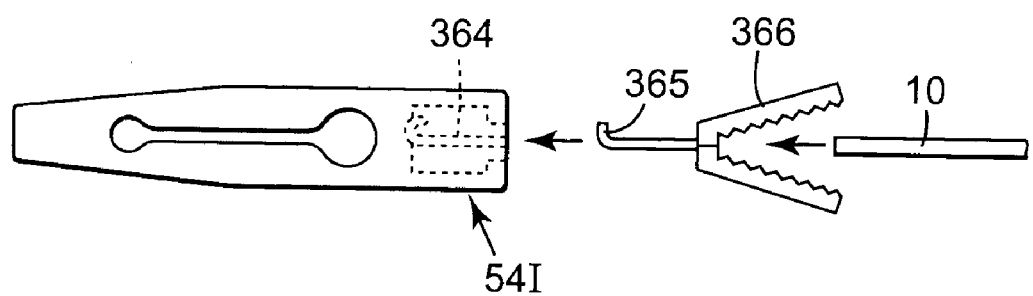
FIG. 41 is a side view of another embodiment of adapter and sling material according to the present invention; with the elements shown in a disassembled condition.
Figure 43:
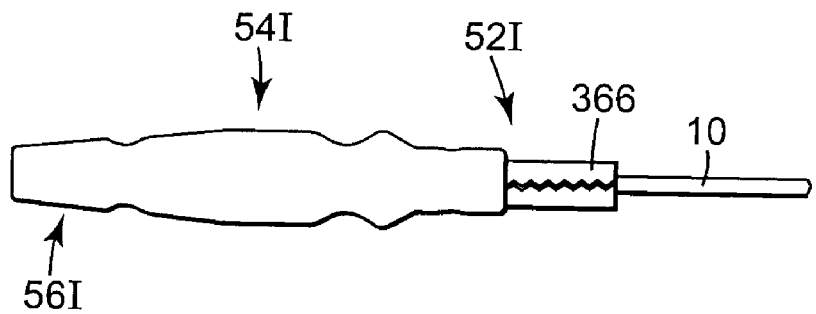
FIG. 43 is a side view of the elements of FIG. 41 with the elements shown in an assembled condition.

Instead of a hole 90 in the dilator 54, another mechanism may be utilized to connect a dilator 54 to a surgical sling material, sheath or sling assembly. FIGS. 41 and 43 illustrate an adapter 54I. One end of the adapter includes a mechanism for attaching to a needle 60. The other end of the adapter 54I includes a means for attaching to a sling 10. The means for attaching to a sling includes jaws 366 movable between an open position (FIG. 41) for receiving the sling 10 and a closed position (see FIG. 43) for firmly holding the sling 10 and resisting separation of the sling 10 from the adapter 54I.

A fastening arm 365 with securement flange may fit in a hook shaped receiving slot 364 within adapter 54I. Optionally, a spring (not shown) may be utilized to bias the securement flange to the end of the hook to resist separation of the jaws 366 from the remaining portion of the adapter 54I. When the fastening arm 364 is fully inserted in the slot 364, inner surfaces of the adapter 54I engage outer surfaces of the jaws 366 to retain the jaws 366 in the closed position and to block movement of the jaws toward the open position. Secure association between the jaws 366 resists undesirable separation of the sling 10 and the adapter 54I within the body of the patient.

Figure 42:
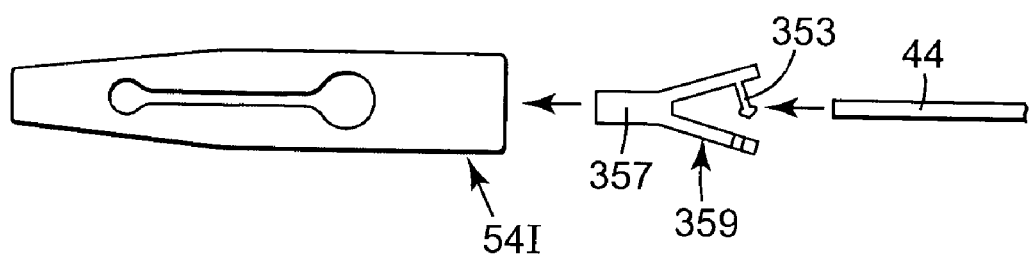
FIG. 42 is a side view of another embodiment of adapter and a sling material according to another aspect of the present invention.

FIG. 42 illustrates another portion of an adapter. The element shown in FIG. 42 includes jaws 359, and threads 357 that can be screwed into complementary threads in an adapter. The jaws 359 include a piercing member 353 that can penetrate through sling or insertion sheath 44. Preferably the piercing member 359 includes an enlarged end portion that can retain the jaws 359 in a closed position and can block separation of the sling material. The piercing member is a positive barrier to separation between the jaws 359 and the sling or insertion sheath 44.

Operating theatres often stock specialized surgical needles that are commonly used by urologists. Such needles include Stamey, Raz, and Pereyra needles. FIGS. 27 and 27A illustrate a needle converter 712 that can exploit a surgeon's comfort in using a stock needle.

FIG. 27A shows a sling assembly comprising a sling mesh material 42 and a dilator 54. An optional sheath 44 is also shown. The sheath 44 is threaded through hole 90 and attached to itself (e.g. by ultrasonic welding). The dilator 54 has an end portion (opposite the end near hole 90) with a passageway. The passageway in the dilator (best seen in FIG. 26) includes surfaces for receiving a first type of needle (e.g. 60).

Preferably, the surgical kit that includes needle converter 712 would also include a needle 60. Needle 60 has an end portion that is sized and shaped to engage complementary surfaces in the passageway of the dilator 54 to associate the needle with the sling assembly. However, for a variety of reasons, a particular surgeon may eschew the use of a first type of needle (e.g. 60) and instead opt to use a commonly available, standard needle (e.g. a Stamey needle 204 having a hole). Such a surgeon may utilize the needle converter 712.

The needle converter 712 includes a first end portion having surfaces 126D and 130D that are sized and shaped to engage complementary surfaces in the passageway of the dilator to associate the needle converter 712 with the dilator 54. Surfaces 126D and 130D are substantially the same shape as surfaces 126 and 130 of needle 60 (see FIG. 4). The needle converter 712 has a second end portion that is opposite the first end portion. The second end portion has a means for attaching the needle converter 712 to a second type of needle (e.g. Stamey needle 204) that is different than the first type of needle 60.

The connection to the second type of needle can take a variety of shapes. A plurality of needle converters can be supplied in the same surgical kit. FIG. 27 shows the needle converter 712 in an unassembled condition. The needle converter includes a leaf spring 710 with a locking pin, a locking sleeve 720 and a slot 718 for receiving the end of the second type of needle 204.

The locking pin of leaf spring 710 is preferably movable between a needle accept position (FIG. 27) that allows the needle 204 to be inserted in the needle converter, and a needle engaged position (FIG. 27A) with the locking pin firmly and securely attached to the needle 204. The locking sleeve 720 is moveable between a needle accept position (FIG. 27) and a blocking position (FIG. 27A) that retains the locking pin of leaf spring 710 in the needle engaged position. Preferably, a leading end of the locking pin of leaf spring 710 is angled to cam the leaf spring to the needle accept position when the end of needle 204 is slid into slot 718. An inherent bias of the leaf spring 710 preferably causes the locking pin to move to the needle engaged position and fully seat in the hole in needle 204 when the needle 204 is fully inserted in the converter 712.

FIG. 27A shows the needle converter 712 in an assembled condition. The locking pin of the leaf spring 710 is seated in a hole in the second type of needle 204. The locking sleeve 720 has been slid in the direction of the arrow in FIG. 27 to encompass the leaf spring 710 and to prevent the locking pin from moving out of engagement with the hole in needle 204. Sleeve 720 is preferably blunt with rounded surfaces to resist damage to the patient while it is pulled through the body. Notably, resistance by the body while the sling assembly 42, 44 is pulled through the body will tend to urge the locking sleeve 720 toward the blocking position to resist separation of needle 204 and needle converter 712.

Figure 39:
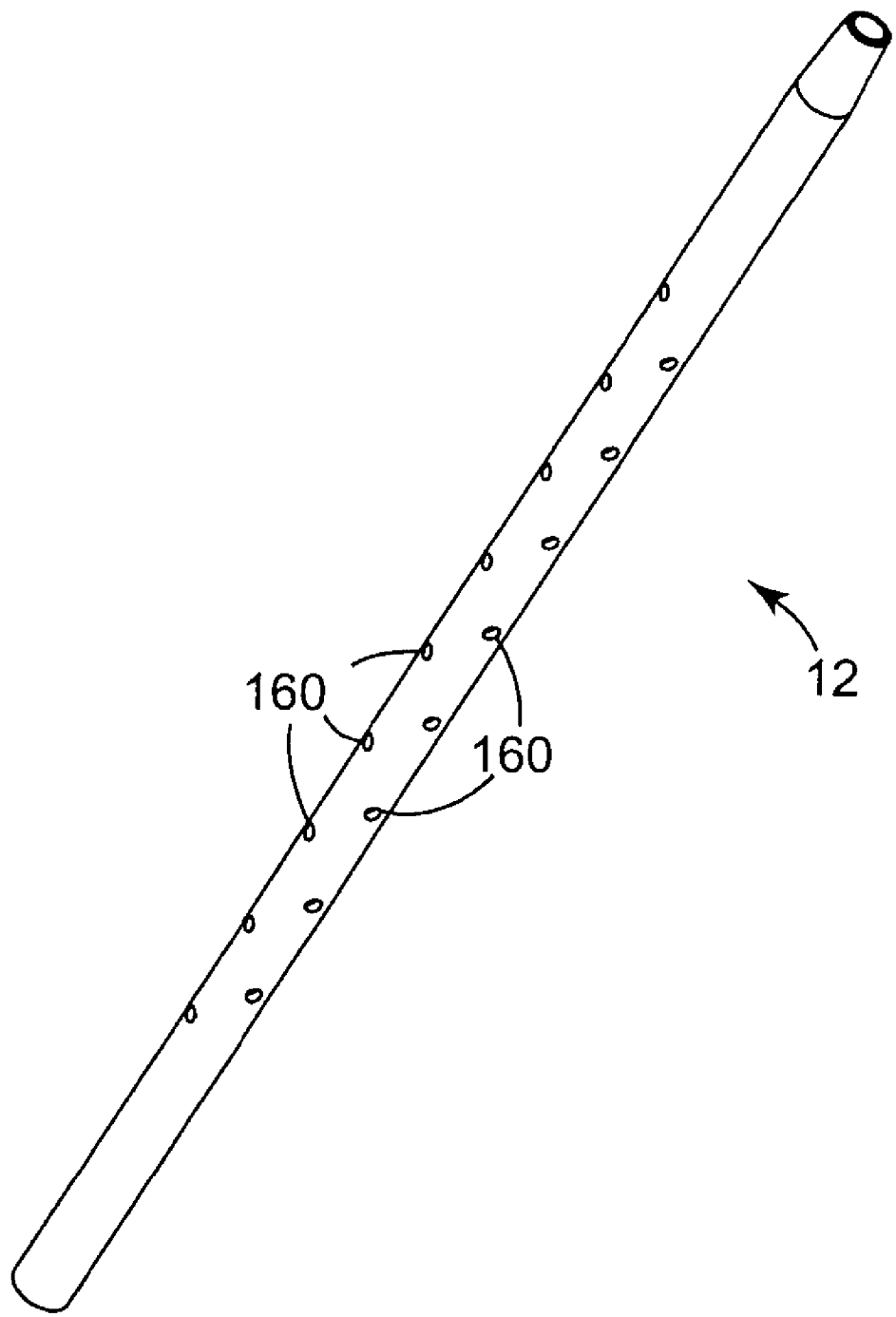
FIG. 39 is a perspective view of an accessory for use in a kit according to the present invention.

A surgical kit according to the present invention may optionally include additional accessories. FIG. 39 illustrates a cystoscopy aid 12. The cystoscopy aid 12 may be inserted over a thin needle 60. The cystoscopy aid includes one or more apertures or perforations 160, that function to facilitate verification of bladder and urethra integrity, are disposed along the length of the cystoscopy aid 12. For example, during use, after the needles 60 have been inserted within the patient, the cystoscopy aid 12 may be pushed along the exterior surface of each needle 60. If the bladder has been punctured during needle insertion causing urine leakage or drainage within the patient, the urine or bladder fluid will enter the apertures 160 of the cystoscopy aid 12 and flow along the surface and out from the needle 60. This allows the practitioner to quickly and easily confirm urethra and bladder integrity.

Other accessories may also optionally be included in a kit according to the present invention. For example, a surgical drape specifically designed for urological procedures such as a sling procedure may be included in a kit of the present invention. Such a drape is disclosed in U.S. patent application Ser. No. 09/749,254, filed Dec. 27, 2001 (the entire contents incorporated herein by reference). Alternatively, an article for objectively setting tension of the device, such as those described in U.S. patent application Ser. No. 09/968,239, filed Oct. 1, 2001 (the entire contents of which are incorporated by reference) may be included in the kit.

Other accessories may also be included for convenience. For example, if a needle includes an optical feature, then a optical elements may be included. If a needle includes a resistance detector, then the kit may include a means for detecting a bladder perforation due to the change in resistance encountered by a needle due to a bladder puncture.

The kits according to the present invention preferably include at least two needles. Two or more needles reduce the need to reuse a needle at a different location with a patient, thereby eliminating cross contamination issues. Additional needles, handles, dilators and other elements may also be included for surgical convenience, for avoidance of contamination from one portion of the body to another, for ease of manufacturing or sterilization or for surgical requirements.

The individual elements of the kits of the present invention may be packaged together, separately or in subassemblies depending on a variety of factors such as shelf life and sterilization requirements. They may be assembled at the manufacturing location or at the healthcare location. Any suitable sterilization procedure may be utilized to sterilize the contents of a kit. Suitable sterilization techniques include, but are not limited to steam, ethylene oxide, electron beam, vapor (e.g. hydrogen peroxide or peracetic acid), or plasma procedures.

Examples of Surgical Procedures

Several methods are contemplated herein. Although the methods of use as disclosed herein generally relate to female incontinence conditions and treatments/procedures, male incontinence conditions and treatments/procedures are also included within the scope of the present invention. Procedures that address problems other than incontinence (e.g. cystocele, enterocele or prolapse) are also contemplated alone or in conjunction with the present invention. Further, the term "urethra," with respect to sling positioning, is used for brevity and reader convenience. It should be noted that the present invention is particularly suitable for placing a sling in a therapeutically effective position. The method may be utilized to support a variety of structures at different anatomical locations. As such, the terms "target site," "bladder", "urethro-vesical juncture", "vaginal vault", "U-V juncture" and "bladder neck" are also included within the scope of the present invention.

The present invention includes surgical procedures that utilize the novel surgical instruments, articles and kits described above. The present invention also includes improved surgical sling procedures.

Figure 28:
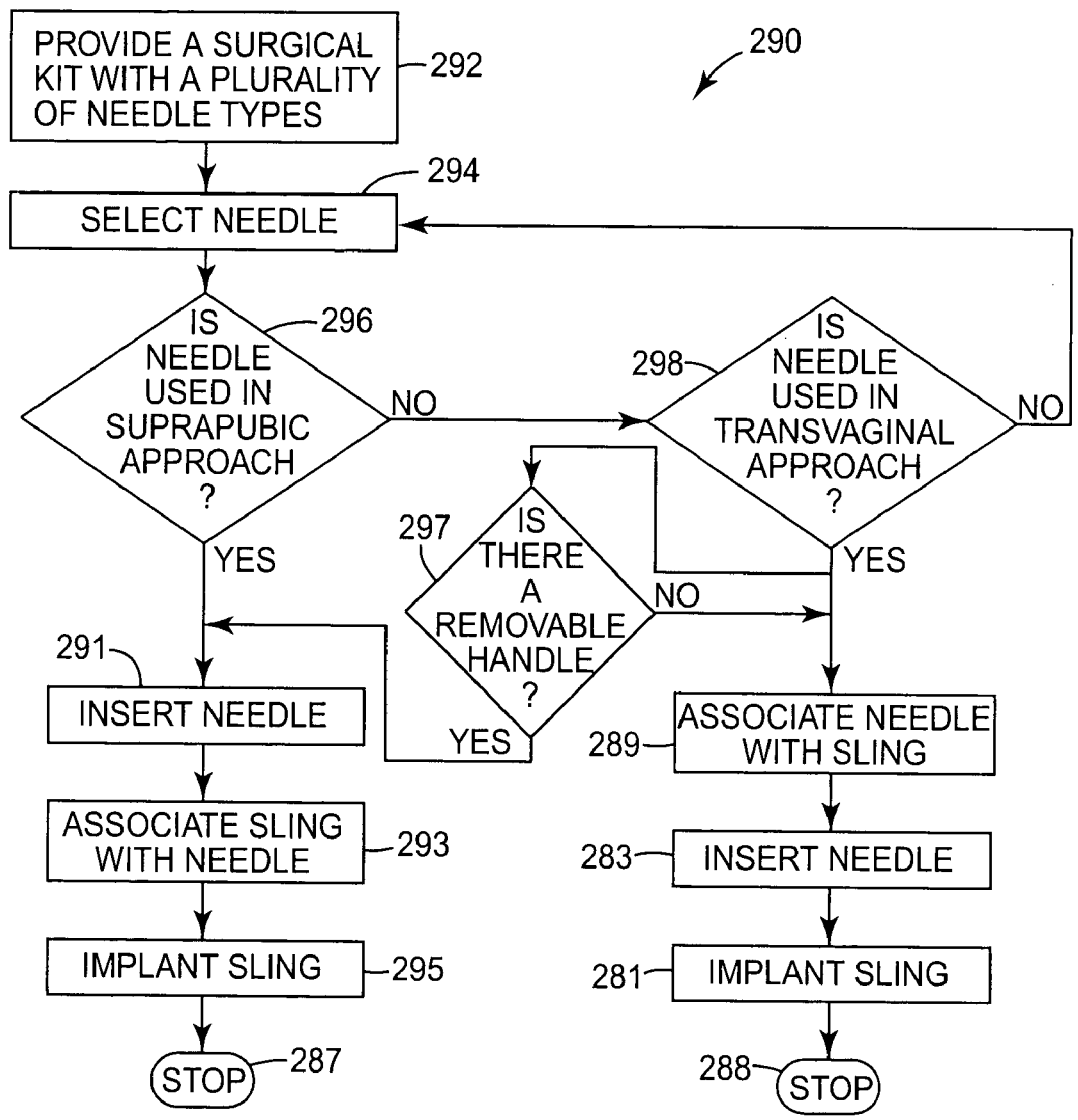
FIG. 28 is a flow chart showing a process according to an aspect of the present invention.

Referring now to FIGS. 1A and 28, there is shown a first embodiment of method according to the present invention. The method includes step 292 of providing a surgical kit with an implantable material (e.g. a sling mesh from sling assembly 46), at least one of a first type of needle (e.g. needle with curved portion 60), and at least one of a second type of needle (e.g. straight needle 60A).

The method also includes step 294 of selecting the first 60 or the second 60A type of needle. Next, in step 296, a decision is made as to whether the needle is initially placed through an abdominal incision and then through a vaginal decision (e.g. a suprapubic approach). If the suprapubic approach is utilized, the needle is inserted in the body in step 291, a sling is then associated with a portion of the needle extending through a vaginal incision in step 293. The sling is implanted in step 295. After the sling is implanted, the incisions are closed at the end of the procedure (step 287).

Alternatively, step 298 may decide that the needle will be initially inserted in a vaginal incision and then passed through an abdominal incision (a suprapubic approach). If an optional removable handle is used, in step 297, it may be desirable to initially associate the handle with the needle and then insert the needle in step 291. If no removable handle is used or once it is removed, the sling may then be associated with the needle (e.g. step 289) used in the transvaginal approach. The needle is inserted (e.g. step 283), the sling is implanted (step 281), incisions are closed and the procedure ends 288.

The present invention preferably utilizes a suprapubic approach. A suprapubic approach affords greater control over the end of a needle to avoid areas with sensitive vascular structures and the obturator nerves. Further the heightened control associated with a caudad passage is believed to avoid injury to bowel tissue.

Figure 29:
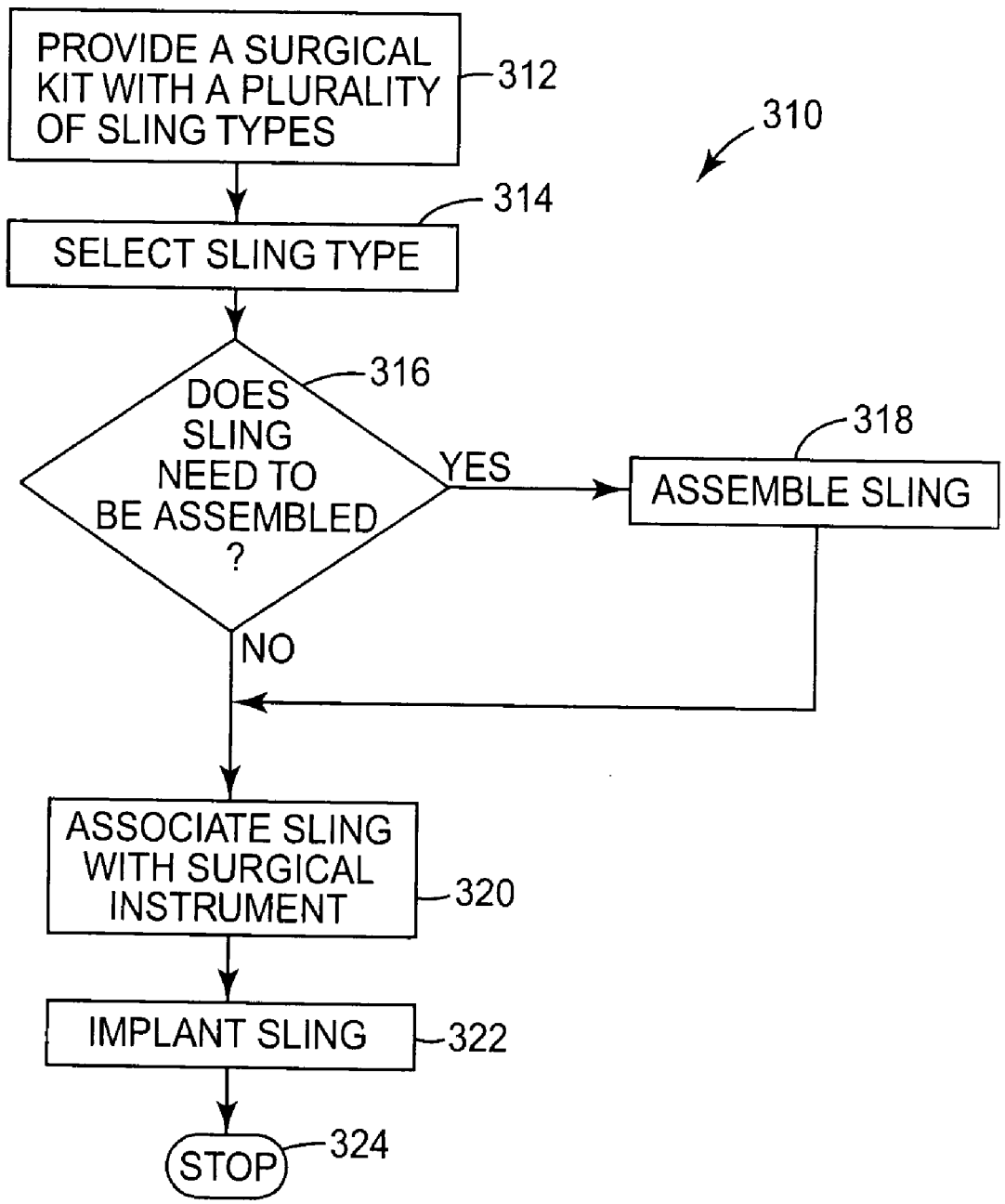
FIG. 29 is a flow chart showing another process according to another aspect of the present invention.

Additional methods according to the present invention are shown in FIGS. 1, 2, 21 and 29. Referring to FIGS. 1 and 29, another method according to the present invention comprises the steps providing a surgical kit 312 having a first type of sling material (e.g. a synthetic material associated with sling assembly 46), a second type of sling material (e.g. a different type of synthetic sling material or a non-synthetic sling 10), and a surgical instrument (e.g. needle 60) for implanting a sling material. The method includes step 314 of selecting the first type of sling material or the second type of sling material, step 320 of associating the sling with the needle 60, and step 322 of implanting the sling material with the needle 60.

The method may optionally include the steps of constructing or assembling the sling from the plurality of sling material types. Step 316 decides whether a sling should be constructed or whether a pre-existing sling may be used. If it is decided that a hybrid sling need not be assembled (i.e. that synthetic sling assembly 46 could be used alone), then sutures 6 and the mechanical fastener (e.g. grommet 8) may be used to attach a sling assembly 46 to dilator 54.

Notably, non-synthetic sling materials typically include storage and sterilization requirements quite different than synthetic slings. As a result, non-synthetic slings are preferably not packaged with synthetic slings due to considerations such as shelf life. Referring to FIG. 2, a mechanical fastener (e.g. grommet 8) may be included in a surgical kit to enable a bulk non-synthetic sling material 14 to be cut and assembled to a synthetic sling material 42. As a result, a surgeon has the option of constructing a hybrid sling according to an aspect of the present invention.

A surgeon may desire to assemble a hybrid sling for a variety of reasons. For example, some sling materials may be believed to be less likely to erode sensitive tissue such as the urethra. Silicone coated slings and non-synthetic slings may be believed to be less likely to erode the urethra than some synthetic slings. Additionally, some synthetic slings may be more likely to encourage tissue ingrowth. As a result, as shown in FIG. 2B, the surgeon may wish to assemble a sling with a mid portion made of one type of sling material and another portion made of another type of sling material. Other factors may also influence the surgeon's decision, such as previous failure of a particular type of sling material, the existence of scarring or other anatomical characteristics of a patient, and the influence of concomitant procedures.

Referring now to FIGS. 21 and 30 through 37, a preferred embodiment of surgical procedure is disclosed. Initially, the patient is placed under local, spinal or general anesthesia. A small transverse incision 404 is made in the anterior vaginal wall 20 of a female patient followed by a transurethral dissection. Two small transverse suprapubic abdominal stab incisions 400 are also made near the back of the pubic bone (e.g. each about 1 cm from the midline, or alternatively, one large incision may be made) to allow for needle entry. Optionally, two paraurethral dissections (incisions next to the urethra) lateral to the midline may be created to allow the surgeon's finger to meet the end 58 of the needle 60 during the procedure.

Figure 30:
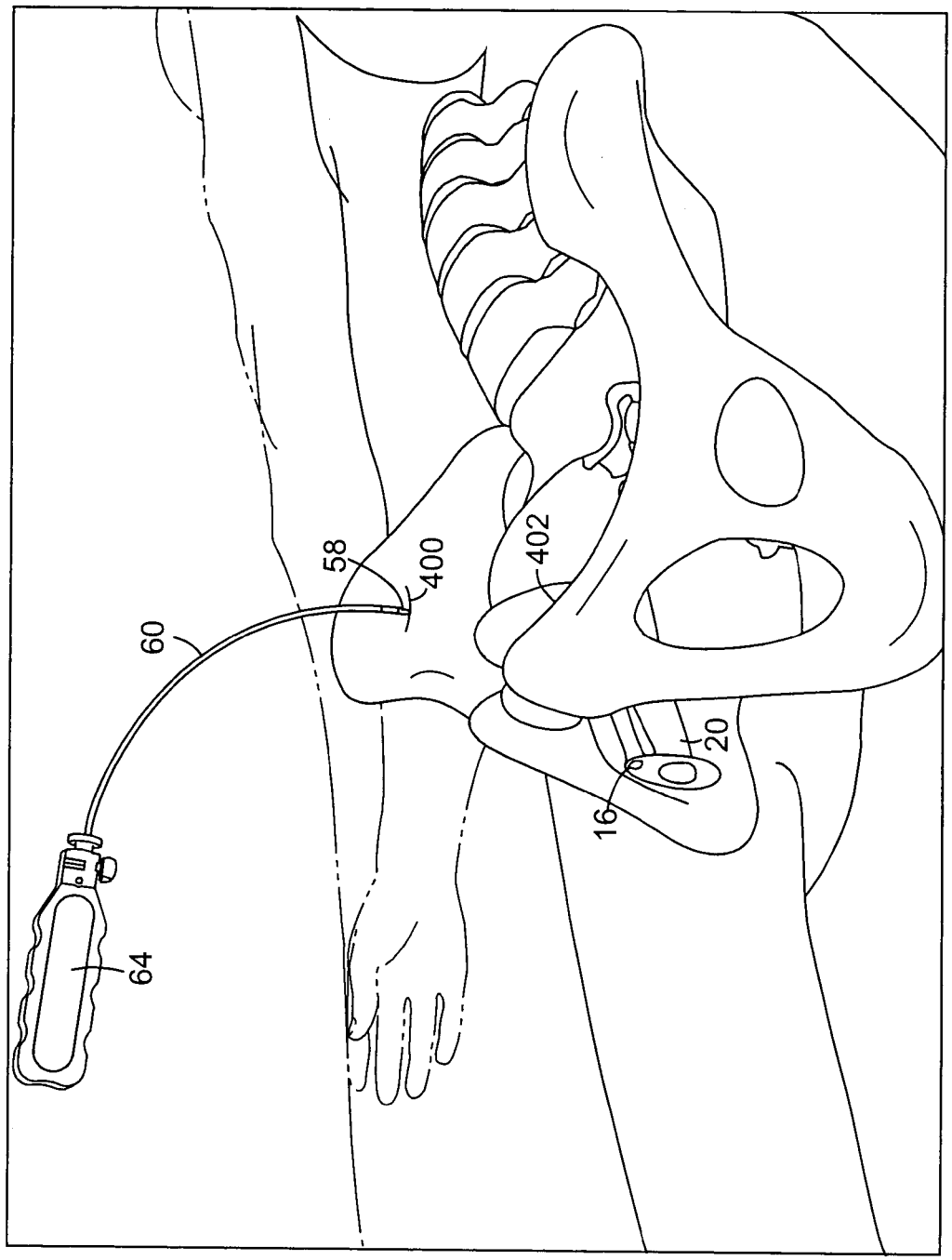

A handle 64 is optionally adjusted relative to needle 60 according to surgeon preference and securely associated with the end 62 of the needle 60. FIG. 30 shows the end 58 of needle 60 just passing an abdominal incision 400. Preferably, after the end 58 of the needle 60 passes the suprapubic abdominal incision 400, the surgeons seeks to encounter resistance associated with the posterior portion of the patient's pubic bone 402 with the end 58 of the needle 60 to controllably move the end 58 of the needle toward the vaginal incision 404 and to help avoid damaging structures such as the urethra and bladder of the patient. The end 58 of the needle 60 is used to identify the location of the pubic bone 402. The surgeon exploits the resistance provided by the pubic bone 402 to controllably pass the end of the needle 58. This approach is preferred as it helps keep the needle 60 away from major pelvic vessels, nerves and anatomical structures such as the urethra, bowels and bladder.

Figure 31:
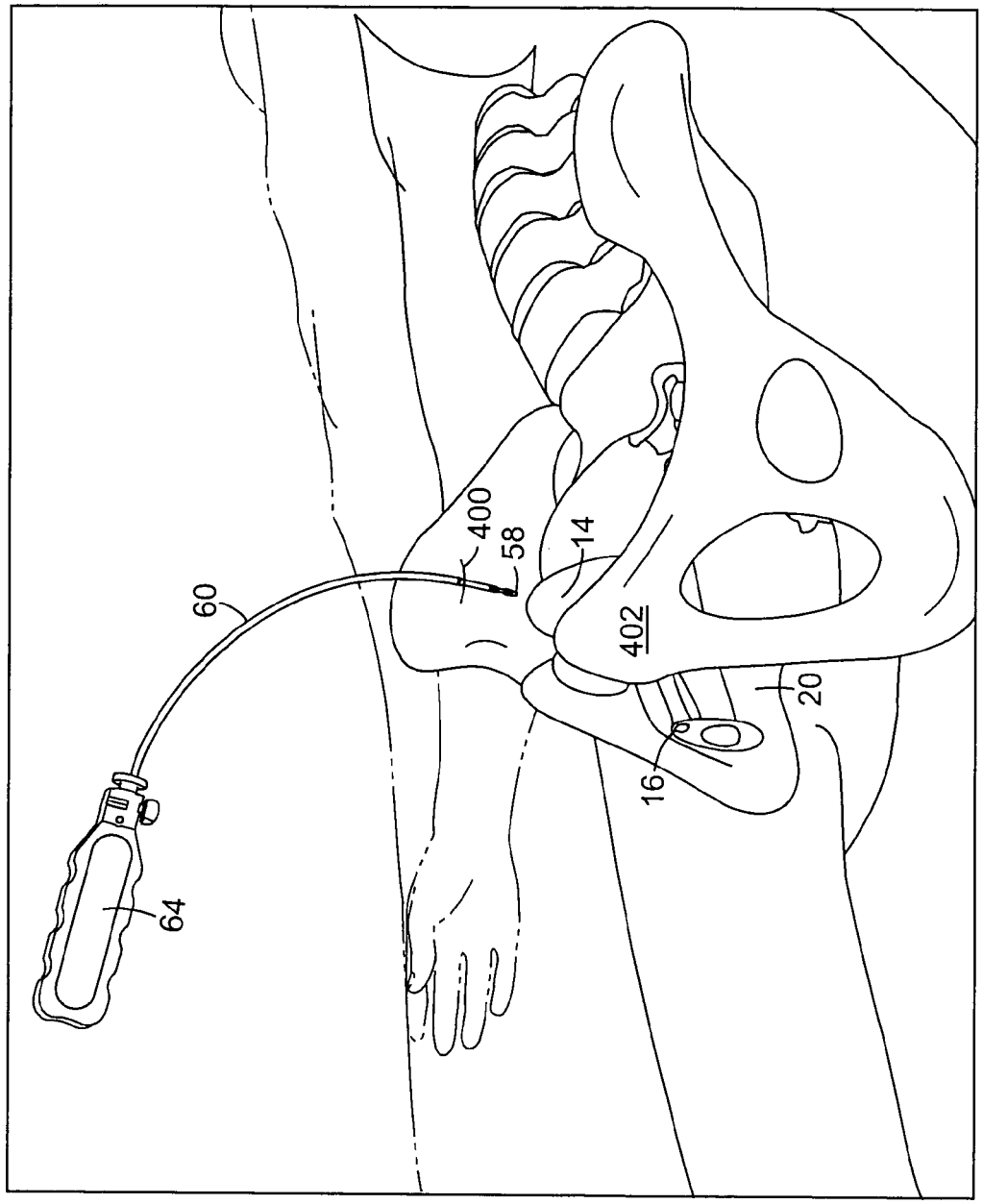
Figure 32:
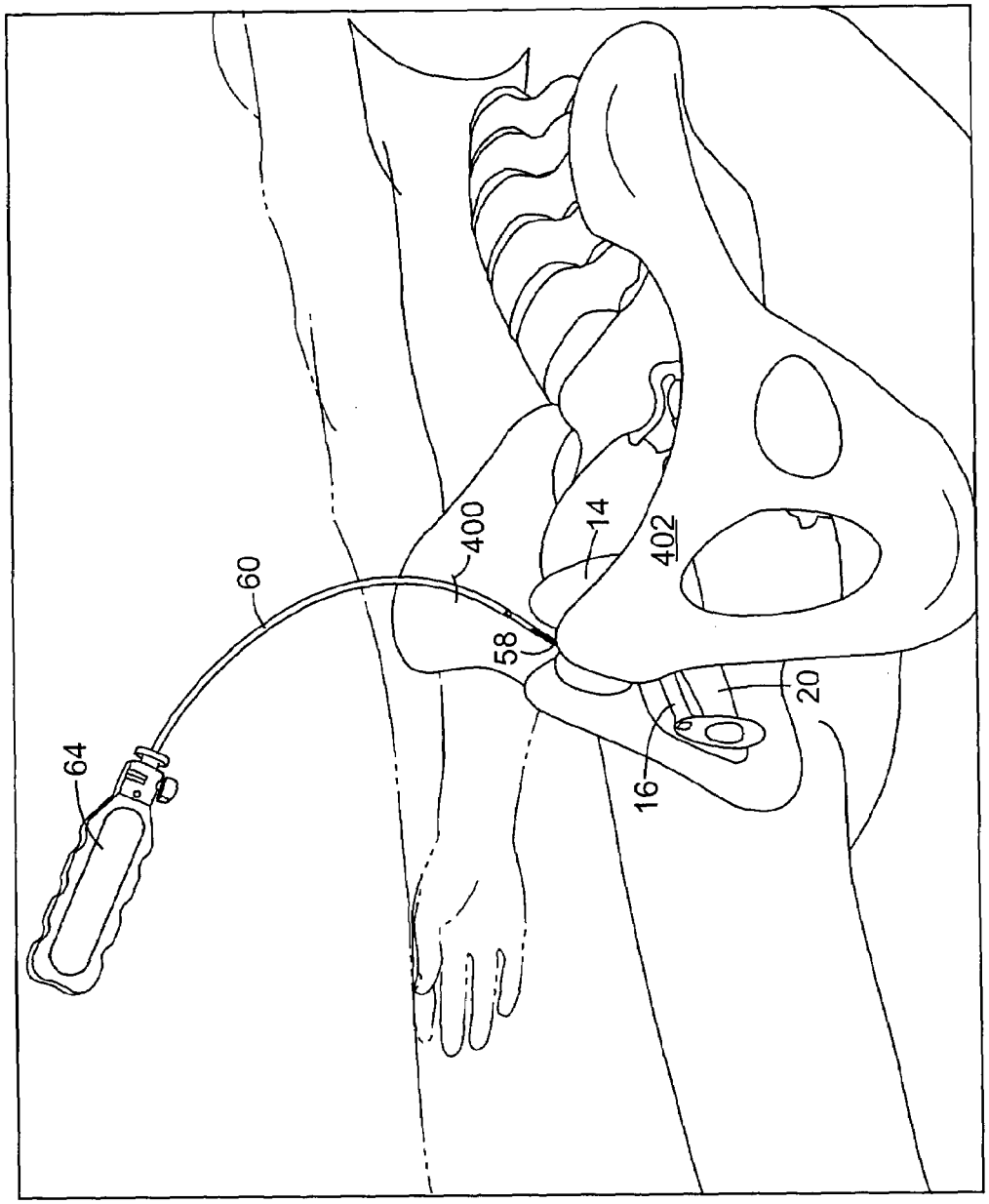

FIG. 31 illustrates the end of the needle as it just passes the suprapubic incision. FIG. 32 illustrates the needle 60 as the surgeon experiences the tactile feel of the resistance provided in part by the posterior portion of the pubic bone 402. FIG. 32 shows the needle 60 as it passes in proximity to the posterior surface of the pubic bone 402 which continues to operate as an anatomical guide for the surgeon as the needle end 58 approaches vaginal incision 404 (see FIG. 33).

Figure 33:
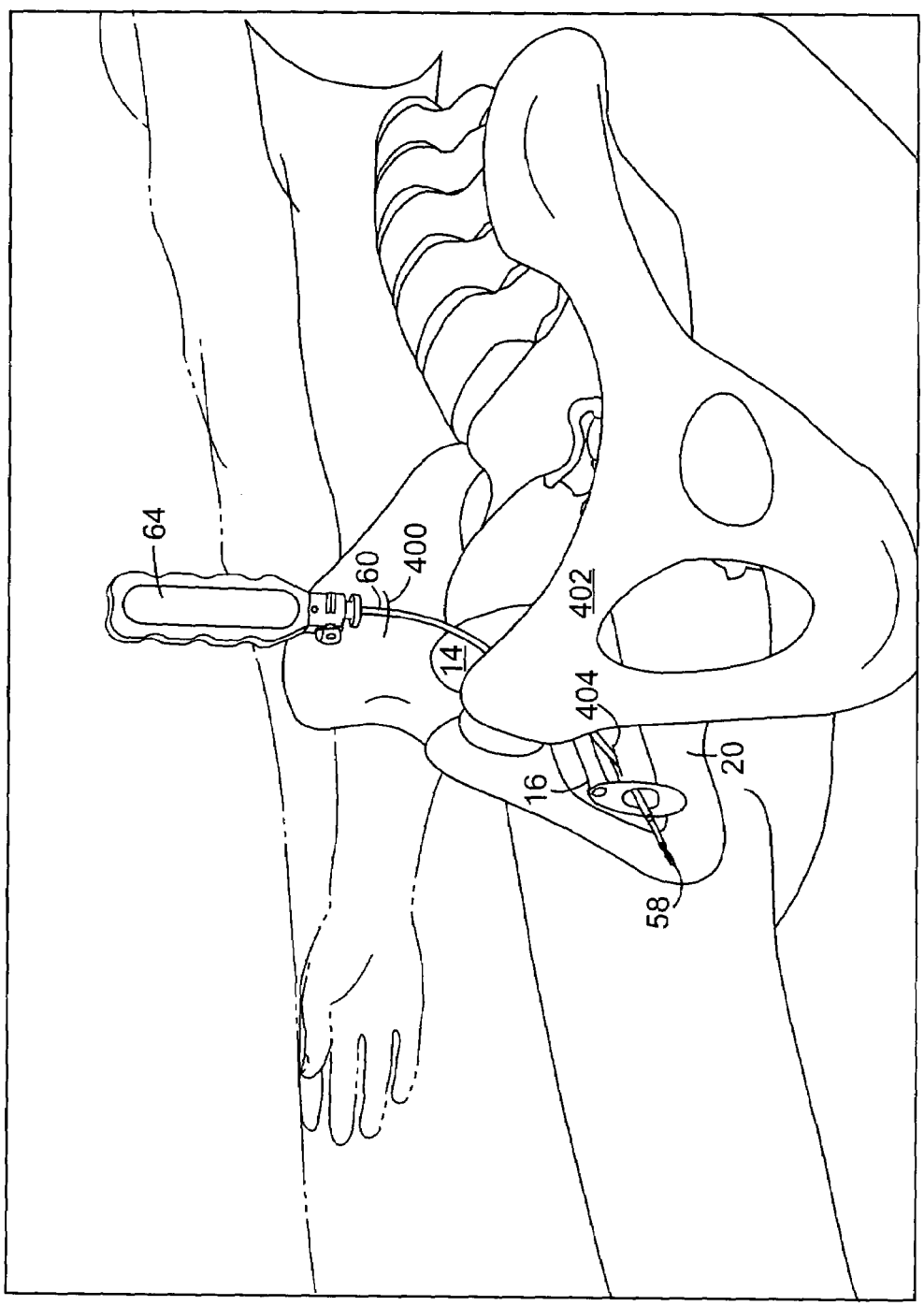

FIG. 33 illustrates the needle as it passes out of a vaginal incision 404. Optionally, with the index finger of a hand, the surgeon may meet the end 58 of the needle via the paraurethral dissection. The surgeon's finger may be delicately placed adjacent endopelvic fascia of the patient and used to guide the needle 60 through the relatively tough endopelvic fascia and into the vaginal incision 404. This helps the surgeon keep away from structures such as the bladder, urethra and other sensitive tissue.

The small diameter and curvature of the needles 60 help to provide precise passage of the needles 60 to the vaginal incision 404. In addition, this needle configuration creates a minimally invasive pathway through tissue extending between the abdominal wall and pubic space, thereby reducing the risk of perforating the bowel and/or blood vessels and nerves located lateral to the bladder 14.

The steps described above are repeated as needed for a second needle 60 on the other side of the urethra 16. Once both needles are placed, surgeons typically perform a cystoscopy to ensure that the bladder is not punctured before implanting the sling. A cystoscopy confirms the integrity of the bladder 14 and urethra 16 or recognizes a bladder perforation. The plastic cystoscopy aid shown in FIG. 39 may optionally be used for this purpose. The cystoscopy aid may be used separately or in conjunction with cystoscopy.

FIG. 34 is a perspective view of a sling system associated with two needles 60. Optional adapters (e.g. dilators 54) are pushed onto the ends 58 of needles 60 as shown in FIG. 34. The dilators 54 are preferably snapped irreversibly into place for a secure connection. Next, if a synthetic sling assembly (such as the sling assembly of FIG. 22) is used, the plastic sheath 44A is oriented so that the optional center orientation indicia (e.g. a blue mark) is facing away from the surgical field, toward the surgeon After the dilators 54 are attached to the needles 60, the sling assembly 46A is properly oriented so that the sling assembly 46A is not twisted when attached to the dilators 54. After the dilators 54 and sling assembly 46A are properly positioned, the dilators 54 are securely attached to the sling assembly 46A by tying sutures 6 through holes 90 so that none of the assembly separates as the needles 60, dilators 54 and sling assembly 46A are pulled through the tissues of the patient. Alternatively, the sling assemblies 240 and 250 could be associated with dilators 54 by tying any of sutures 6A, 6D or 252 to the holes 90 of dilators 54. Alternatively, the sling assembly 46 (FIG. 2) may include a loop 48 that is threaded through hole 90 and secured via mechanical fastener 8. A sling assembly that includes a sheath and sling material (e.g. 42) preassembled to the dilator 54 is also within the scope of the present invention. Additionally, it is noted that the dilator 54 is completely optional and that instead, the sutures (e.g. 6, 6A, 6D or 252) could be tied directly to a needle (e.g. 80 or stock ligature carrier) without the necessity to include the adapter/dilator 54.

Once the dilators 54 are securely attached, the needles are pulled up through the suprapubic incisions, taking care to avoid contact with sensitive tissue. The sling is then clamped with surgical clamps (not shown). During this portion of the process, the attached dilators 54 and sling assembly 46A are atraumatically pulled up through the needle paths, advancing the sling assembly 46A adjacent to and looped beneath the urethra 16 or target site. A portion of each end of the sling assembly 46A extending beyond the suprapubic incisions 400 is clamped and then cut to release the needles 60 and attached dilators 54.

The sling is placed in a therapeutically effective position. The precise anatomical position will depend upon a variety of factors including the type and degree of anatomical damage or insufficiency, whether the sling procedure is combined with other procedures and other surgeon decisions. Typically, the sling is placed midurethra, without tension, but in position to support the midurethra. Alternatively, the sling could be placed to support the bladder neck and/or UV junction.

Once the sling assembly 46A is carefully positioned under the midurethra or target site to provide sufficient support to the target site, the overlapping portion of the sheath 44A located near the center of the sling assembly 46A and optional member 66 (i.e. tensioning filament) may then be used to center and properly position the sling assembly 46A under the midurethra. The sheath 44A is then removed.

Figure 35:
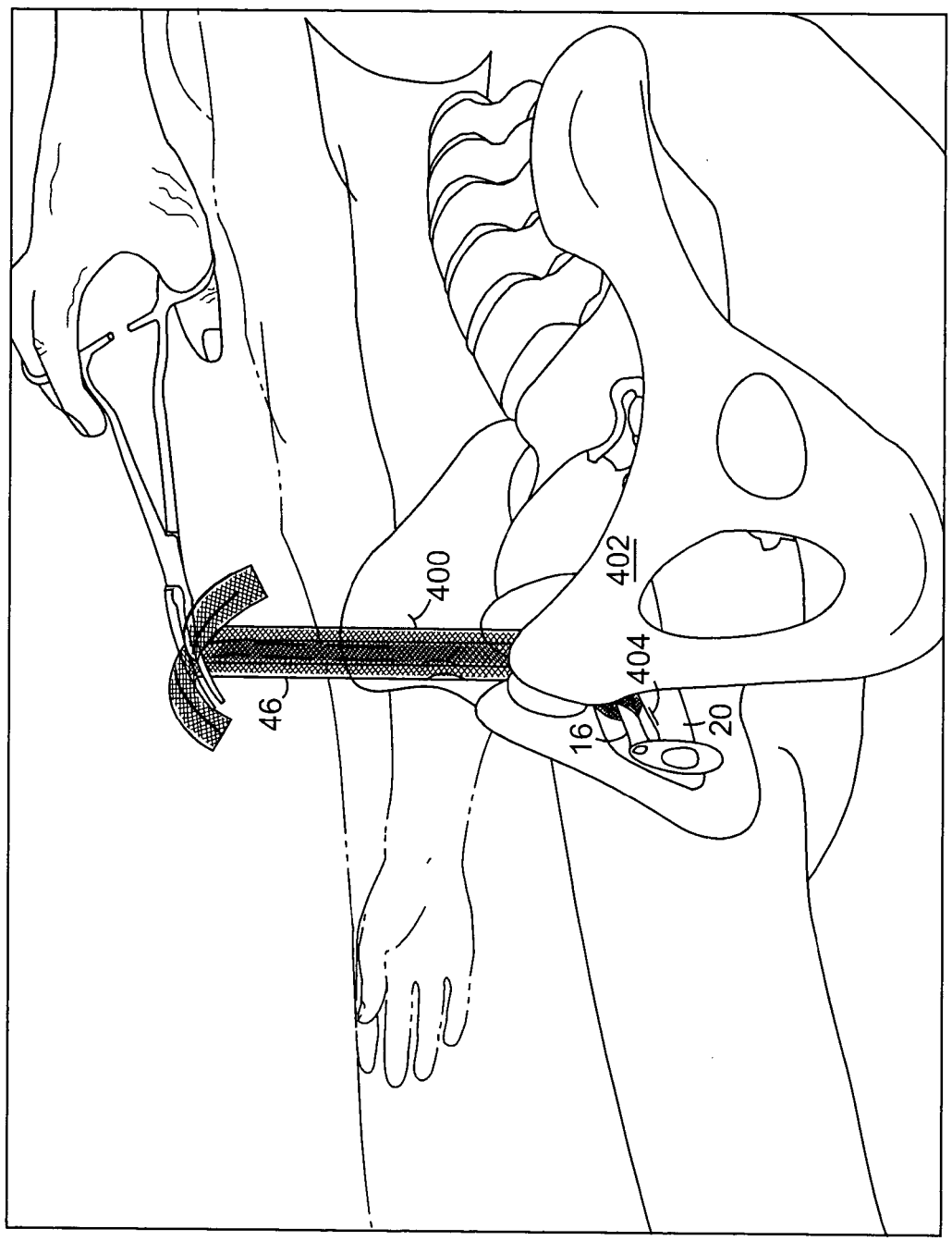
FIG. 35 is a perspective view of a sling assembly being pulled upward by a needle in accordance with the present invention.
Figure 36:
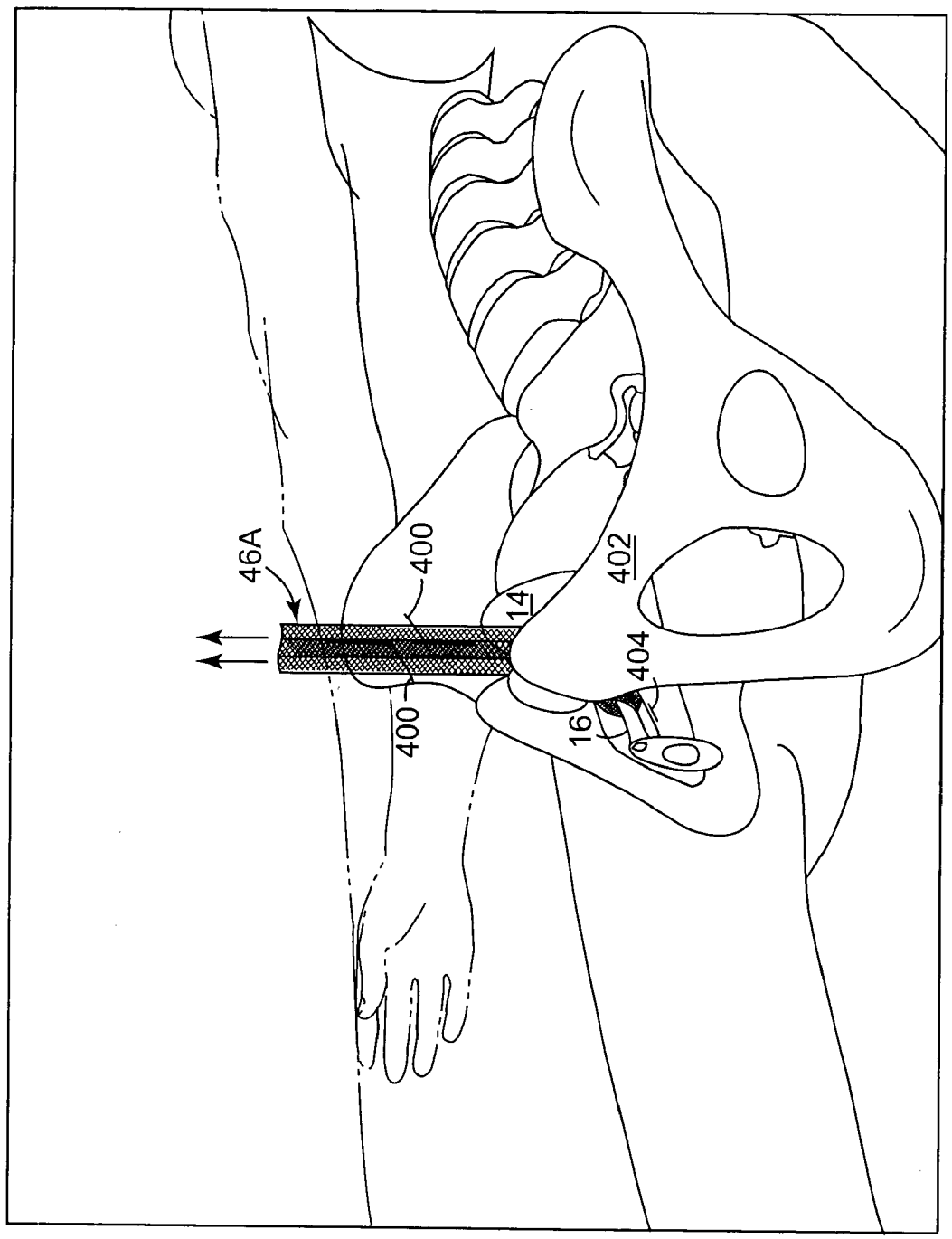
FIG. 36 is a perspective view of the sling according to the present invention after the adapters have been separated from the rest of the assembly, but prior to final trimming.
Figure 37:
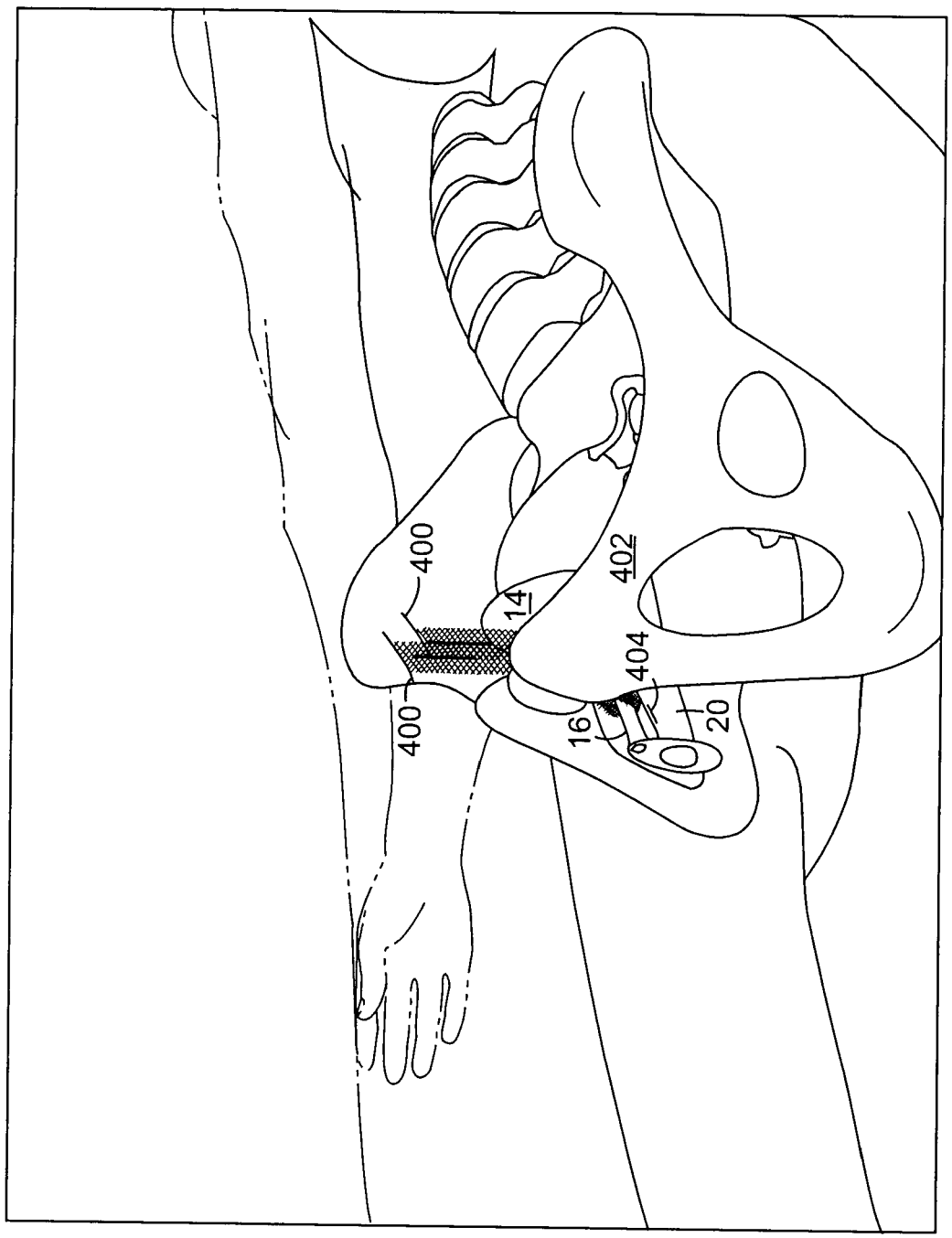
FIG. 37 is a perspective view of the sling according to the present invention after the sheath has been removed and the sling has been trimmed.

FIG. 35 shows the sling being tightened during the surgical procedure. Sling tension may be tightened by placing a device, such as a clamp, across one or both ends of the sling 42, suprapubically. Generally, the surgeon grasps the mesh and tensioning filament together adjacent the suprapubic incision 400 and pulls to increase the degree of tightness of the mesh. FIG. 35 shows the sling after the dilators have been cut off, but prior to final trimming.

After the dilators 54 are trimmed off, the plastic sheath 44A is removed from the sling mesh 42A by pulling up on both sides of the sheath 44A, preferably one at a time. Optionally, to avoid overtightening the sling mesh 42A while removing the sheath 44A, a forceps or other blunt instrument may be placed between the sling and the urethra.

In another embodiment of the invention, shown with reference to FIG. 38, a method includes the steps of: providing a surgical kit comprising at least one guide needle 602 with a relatively small diameter (e.g. less than 4 mm), and at least one sling transport needle 604 with a sharp tip, a sling 610 attached to the sling transport needle 604, and an adapter (e.g. dilator 54) having tip receiving surfaces (e.g. an end of innerpassageway 96 near end of the dilator having hole 90) for receiving the sharp tip of the sling transport needle 604. For example, the sling transport needle 604 and sling 610 may comprise a TVT needle and sling available from Ethicon of New Jersey.

The method includes the steps of creating at least one vaginal incision 404, creating at least one suprapubic incision 400, and initially passing the guide needle 602 through the suprapubic incision 400 and then through the vaginal incision 404, and associating or attaching the adapter 54 to the needle 602 (preferably after but optionally before passage of the needle 602 from the suprapubic incision to the vaginal incision 404).

Needles 604 are initially passed through a vaginal incision 404 and toward one of the suprapubic incisions 400. While inserting the needles 604 initially through the vagina is not preferred, it is within the scope of the present invention as some surgeons may prefer this approach due to previous surgical training, custom or personal preference. The method includes the step of placing the sharp tip of the sling transport needle 604 in the tip receiving surfaces of the adapter 54, and then guiding the sling transport needle 604 from the vaginal incision 404 to the suprapubic incision 400 with the guide needle 602 to implant the sling 610. Handle 620 may be connected to sling attachment end of needle 604 for this purpose. Guiding the sharp tip of the large sling transport needle 604 in this fashion is believed to help avoid contact between the sharp tip of needle 604 and sensitive structures such as obturator nerves, and vascular structures such as the superficial epigastric vessel, the inferior epigastric vessel, the external iliac artery and the obturator. Optionally the adapter with receiving surfaces may be integrally formed in the needle 602 to avoid the need to separately attach the adapter to the needle 602. Also optionally, the adapter and sling transport needle 604 may include complementary engagement surfaces for securely attaching the needle 602 to the needle 604.

In another aspect of the present invention, a needle dilator or adapter may not be needed in a surgical procedure. For example, the procedure may utilize a sling assembly that includes a suture extending from the end of the sling assembly (e.g. a sling as described in conjunction with FIG. 22 or 22A). The method includes the steps of: i) providing the sling, ii) creating at least one vaginal incision, ii) creating at least one suprapubic incision, iii) passing a leading end of a needle initially through a suprapubic incision and then through the vaginal incision on one side of the patient's urethra, iv) passing a leading end of a needle initially through a suprapubic incision and then through the vaginal incision on the other side of the patient's urethra, v) attaching the first suture to the leading end of a needle, vi) attaching the second suture to the leading end of a needle, vii) implanting the sling by moving the leading end of a needle from the vaginal incision toward a suprapubic incision, and viii) then removing the synthetic insertion sheath. In one embodiment, the needle may comprise a needle or ligature carrier (e.g. such as needle 80 shown in FIGS. 9, 9A and 10) that includes a retractable suture holder for securely holding the suture to the needle while the needle and sling assembly are drawn up through the body. A single needle (e.g. the same needle 80 used on both sides of the urethra) or two needles could be used in this embodiment of surgical procedure.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical kit for treating incontinence comprising:
   an implantable material suitable for a sling procedure,
   at least one of a first type of needle suitable for a sling procedure, and
   at least one of a second type of needle suitable for a sling procedure, and
   a dilator for associating said implantable material suitable for a sling procedure with at least one of said first or second types of needles,
   wherein the first type of needle comprises a substantially straight needle and the second type of needle comprises a needle with a curved portion.

2. A surgical kit according to claim 1 further including a synthetic insertion sheath associated with the implantable material to form a sling assembly.

3. A surgical kit according to claim 2 wherein said dilator is adapted for associating the sling assembly with a surgical needle.

4. A surgical kit according to claim 1 wherein the first type of needle comprises a needle with at least two handles.

5. A surgical kit according to claim 1 wherein the first type of needle includes an end portion with a passageway for receiving a suture.

6. A surgical kit according to claim 5 wherein the passageway for receiving a suture comprises a hole.

7. A surgical kit according to claim 1 wherein the first type of needle includes at least two straight portions situated at a predetermined angle.

8. A surgical kit according to claim 1 further comprising a first type of handle and a second type of handle wherein the first type of handle is different than the second type of handle.

9. A surgical kit according to claim 1 wherein the first type of needle is larger than the second type of needle.

10. A surgical kit according to claim 1 wherein the first type of needle includes a bladder perforation detector.

11. A surgical kit for treating incontinence comprising:
an implantable material suitable for a sling procedure,
at least one of a first type of needle suitable for a sling procedure, and
at least one of a second type of needle suitable for a sling procedure, wherein the first type of needle is different than the second type of needle, and
a dilator adapted to associate said implantable material suitable for a sling procedure with at least one of said first or second types of needles,
wherein the first type of needle comprises a movable inner member with a blunt end portion having a suture passageway and an outer sheath member with a sheath end, and
means for moving the blunt end portion between i) an extended position with the suture passageway extending beyond the outer sheath member, and ii) a retracted position with the blunt end portion spaced closer to the end of the outer sheath member than in the extended position.

12. A surgical kit according to claim 11 wherein the sheath end comprises a substantially sharp surface for cutting tissue, and the first type of needle includes a means for locking the blunt end portion in the extended position.

13. A method of implanting a sling to treat urinary incontinence in a patient comprising the steps of:
providing a surgical kit comprising at least one guide needle, and at least one sling transport needle with a tip, a sling attached to the sling transport needle, and an adapter having two ends with a gentle taper near one end, said adaptor further having tip receiving surfaces for receiving the tip of the sling transport needle, wherein said adapter comprises a snap mechanism configured to securely attach said guide needle and said adapter,
creating at least one vaginal incision,
creating at least one suprapubic incision,
initially passing the guide needle through the suprapubic incision and then through the vaginal incision,
attaching the adapter to the guide needle,
placing the tip of the sling transport needle in the tip receiving surfaces of the adapter, and
guiding the sling transport needle from the vaginal incision to the suprapubic incision with the guide needle to implant the sling.

14. A surgical kit for treating incontinence comprising:
at least one guide needle,
at least one sling transport needle with a tip, and a sling attached to the sling transport needle, and
an adapter having:
two ends with a gentle taper near one end,
tip receiving surfaces for receiving the tip of the sling transport needle, and
a snap mechanism configured to securely attach said guide needle and said adapter.

15. A surgical kit according to claim 14 wherein the adapter is integral with the guide needle.

16. A surgical kit for treating incontinence comprising:
an implantable material suitable for a sling procedure,
a needle that is sized and shaped for inserting a sling, the needle having surfaces for engaging a handle,
a dilator for associating said implantable material suitable for a sling procedure with said needle,
at least one of a first type of handle having surfaces for attaching the handle to the needle, and
at least one of a second type of handle having surfaces for attaching the handle to the needle, wherein the first type of handle is different than the second type of handle.

17. A surgical kit for treating incontinence comprising:
an implantable material suitable for a sling procedure,
at least one of a first type of needle suitable for a sling procedure, and
at least one of a second type of needle suitable for a sling procedure, wherein the first type of needle is different than the second type of needle,
a dilator for associating said implantable material suitable for a sling procedure with at least one of the first and second type of needle,
wherein at least one of said first and second type of needle comprises means for transporting said implantable sling material and dilator in a body of a patient.

* * * * *

UNITED STATES PATENT AND TRADEMARK OFFICE
CERTIFICATE OF CORRECTION

| | | |
|---|---|---|
| PATENT NO. | : 7,291,104 B2 | Page 1 of 1 |
| APPLICATION NO. | : 10/675816 | |
| DATED | : November 6, 2007 | |
| INVENTOR(S) | : Johann J. Neisz et al. | |

It is certified that error appears in the above-identified patent and that said Letters Patent is hereby corrected as shown below:

Column 10, line 43, "Oust adjacent retaining lip 520)" should be --(just adjacent retaining lip 520)--.

Signed and Sealed this

Twenty-sixth Day of August, 2008

JON W. DUDAS
*Director of the United States Patent and Trademark Office*